United States Patent [19]

Fujii

[11] Patent Number: 5,155,113
[45] Date of Patent: Oct. 13, 1992

[54] COMPOSITION FOR INCREASING THE ANTI-CANCER ACTIVITY OF AN ANTI-CANCER COMPOUND

[75] Inventor: Setsuro Fujii, Kyoto, Japan

[73] Assignee: Otsuka Pharmaceutical Co., Ltd., Tokyo, Japan

[21] Appl. No.: 437,315

[22] Filed: Nov. 17, 1989

Related U.S. Application Data

[63] Continuation of Ser. No. 793,054, Oct. 30, 1985, abandoned.

[30] Foreign Application Priority Data

| Oct. 30, 1984 | [JP] | Japan | 59-229938 |
| Oct. 31, 1984 | [JP] | Japan | 59-230684 |
| Nov. 30, 1984 | [JP] | Japan | 59-254587 |
| Jan. 17, 1985 | [JP] | Japan | 60-7190 |
| Mar. 25, 1985 | [JP] | Japan | 60-59788 |
| Aug. 30, 1985 | [JP] | Japan | 60-192582 |
| Sep. 19, 1985 | [JP] | Japan | 60-207892 |

[51] Int. Cl.$^5$ .............. A61K 31/44; C07D 213/69; C07D 405/04
[52] U.S. Cl. .................. 514/274; 514/344
[58] Field of Search .................. 514/274, 344

[56] References Cited

FOREIGN PATENT DOCUMENTS 2118176 10/1988 United Kingdom .

OTHER PUBLICATIONS

Fujii et al. (Gann 69, 763-772; Dec., 1978).
Fujii et al. (Gann 70, 209-214; Apr. 1979).
Fujii et al. (Gann 71, 100-106; Feb. 1980).
Kimura et al. Gastroenterologia Japnonica, vol. 15, No. 4, 324-329, Aug. 1980.
Chemical Abstracts 105: 97331f (1986).

Primary Examiner—Nathan M. Nutter
Attorney, Agent, or Firm—Armstrong & Kubovcik

[57] ABSTRACT

A composition for increasing the anti-cancer activity of an anti-cancer compound selected from among 5-fluorouracil and a compound capable of producing 5-fluorouracil in vivo, the composition comprising an effective amount of a pyridine derivative represented by the formula $$\underset{R^1 \quad N \quad R^5}{\overset{R^2 \quad \overset{R^3}{|} \quad R^4}{\bigcirc}} \quad (1)$$

wherein $R^1$ is hydroxy or acyloxy, $R^2$ and $R^4$ are each hydrogen, halogen, amino, carboxyl, carbamoyl, cyano, nitro, lower alkyl, lower alkenyl or lower alkoxycarbonyl, $R^3$ and $R^5$ are each hydrogen, hydroxy or acyloxy; when at least one or $R^1$, $R^3$ and $R^5$ is hydroxy, the structure of 1-position on the pyridine ring can be $$\underset{H}{\overset{\diagdown \quad \diagup}{\underset{|}{N}}}$$

due to the keto-enol tautomerism, said hydrogen attached to nitrogen being optionally substituted with a substituent selected from the group consisting of lower alkyl, tetrahydrofuranyl, tetrahydropyranyl, lower alkoxy-lower alkyl, phthalidyl, carbamoyl, lower alkoxycarbonyl-lower alkylcarbamoyl, phenyl-lower alkoxy-lower alkyl, phenylcarbamoyl which may have a substituent on the phenyl ring, lower alkylcarbamoyl, carboxy-lower alkylcarbamoyl, lower alkylthio-lower alkyl and lower alkenyl, provided that the compound having the following formula is excluded, $$\underset{O \quad N \quad}{\overset{OH}{\bigcirc}}$$
$$\quad \quad \alpha$$

wherein $\alpha$ is hydrogen, lower alkyl, tetrahydrofuranyl, tetrahydropyranyl, lower alkoxy-lower alkyl, lower alkylcarbamoyl, lower alkylthio-lower alkyl or lower alkenyl.

61 Claims, No Drawings

COMPOSITION FOR INCREASING THE ANTI-CANCER ACTIVITY OF AN ANTI-CANCER COMPOUND

This application is a continuation of application Ser. No. 06/793,054 filed Oct. 30, 1985 now abandoned.

This invention relates to a composition capable of increasing the anti-cancer activity of anti-cancer compounds.

The compounds used in this invention are unknown as capable of increasing the activity of anti-cancer compounds.

We conducted extensive research to increase the effect of anti-cancer compounds and to render the compounds less toxic and found that when incorporated in an anti-cancer compound such as 5-fluorouracil (hereinafter referred to as "5-FU") or a compound capable of producing 5-FU in vivo, a specific pyridine derivative can potentiate the anti-cancer activity of the 5-FU or the compound in a remarkable degree. The present invention has been accomplished based on this novel finding.

This invention provides a composition for increasing the anti-cancer activity of anti-cancer compounds which comprises an effective amount of pyridine derivative represented by the formula

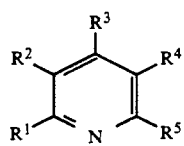 (1)

wherein $R^1$ is hydroxy or acyloxy, $R^2$ and $R^4$ are each hydrogen, halogen, amino, carboxyl, carbamoyl, cyano, nitro, lower alkyl, lower alkenyl or lower alkoxycarbonyl; $R^3$ and $R^5$ are each hydrogen, hydroxy or acyloxy; when at least one of $R^1$, $R^3$ and $R^5$ is hydroxy, the structure of 1-position on the pyridine ring can be

due to the keto-enol tautomerism, said hydrogen attached to the nitrogen being optionally substituted with a substituent selected from the group consisting of lower alkyl, tetrahydrofuranyl, tetrahydropyranyl, lower alkoxy-lower alkyl, phthalidyl, carbamoyl, lower alkoxycarbonyl-lower alkylcarbamoyl, phenyl-lower alkoxy-lower alkyl, phenylcarbamoyl which may have a substituent on the phenyl ring, lower alkylcarbamoyl, carboxy-lower alkylcarbamoyl, lower alkylthio-lower alkyl and lower alkenyl provided that the compound having the following formula is excluded,

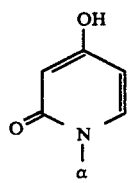

α is hydrogen, lower alkyl, tetrahydrofuranyl, tetrahydropyranyl, lower alkoxy-lower alkyl, lower alkylcarbamoyl, lower alkylthio-lower alkyl or lower alkenyl.

Preferable examples of the pyridine derivatives are 4-acetoxy-5-chloro-2-pyridone, 4-benzoyloxy-5-chloro-2-pyridone, 5-chloro-4-(2-furoyloxy)-2-pyridone, 2-acetoxy-5-chloro-4-hydroxypyridine, 2-benzoyloxy-5-chloro-4-hydroxypyridine, 5-chloro-4-hydroxy-1-(2-tetrahydrofuranyl)-2-pyridone, 4-benzoyloxy-3-chloro-1-(2-tetrahydrofuranyl)-2-pyridone, 4-benzoyloxy-2-pyridone, 5-chloro-2,4-diacetoxypyridine,6-benzoyloxy-3-cyano-2-hydroxypyridine, 3-cyano-6-(2-furoyloxy)-2-hydroxypyridine, 3-cyano-2-hydroxy-6-(2-thenoyloxy)pyridine, 6-benzoyloxy-3-chloro-2-hydroxypyridine and the like. More preferable are 6-benzoyloxy-3-cyano-2-hydroxypyridine, 6-benzoyloxy-3-chloro-2-hydroxypyridine, 4-acetoxy-5-chloro-2-pyridone, 4-benzoyloxy-5-chloro-2-pyridone and the like.

When conjointly used with 5-FU and compounds capable of producing 5-FU in vivo, known anti-cancer compounds represented by the following formulas (2-a) and (2-b), the pyridine derivatives of the formula (1) according to this invention are able to increase the anti-cancer activity of the compound of the formulas (2-a) and (2-b). The known anti-cancer compounds to be used are:

a) 5-fluorouracil compound having the formula

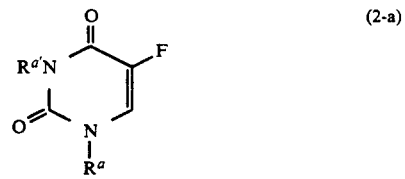 (2-a)

wherein Ra and Ra' are each the same Or different and represent hydrogen, phthalidyl, tetrahydrofuranyl, tetrahydropyranyl, lower alkylcarbamoyl, lower alkoxy lower alkyl, phenyl-lower alkoxy-lower alkyl, acyl or a group

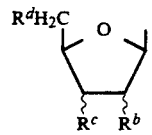

wherein $R^b$, $R^c$ and $R^d$ are each the same or different and represent hydrogen, hydroxy, phenyl-lower alkoxy, phenyl-lower alkoxy-lower alkyloxy, lower alkanoyloxy, aroyloxy or aryloxycarbonyloxy which may have on the phenyl ring 1 to 3 substituents selected from among lower alkyl, lower alkoxy, nitro and halogen; when $R^b$ and $R^c$ are hydroxy group at the same time, they may be combined together through alkylidene or arylidene group to form alkylidenedioxy or arylidenedioxy group; when $R^b$ is hydrogen, $R^c$ and $R^d$ must not be such that one of them is phenyl-lower alkoxy while the other is lower alkanoyloxy or aroyloxy; and (b) A compound of the formula

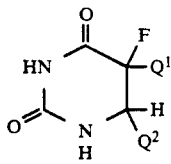

wherein $Q^1$ is lower alkoxycarbonyl and $Q^2$ is lower alkoxy or group

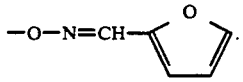

Preferred examples of the above compounds represented by the formulas (2-a) and (2-b) are 5-fluorouracil (5-FU), 1-(2-tetrahydrofuranyl)-5-fluorouracil (FT-207), 1-hexylcarbamoyl-5-fluorouracil (HCFU), 1-ethoxymethyl-5-fluorouracil (OFU), 5-fluorouridine (FUR), 5'-deoxy-5-fluorouridine (5'DFUR), 2'-deoxy-5-fluoro-3-(3,4-methylenedioxybenzoyl)uridine (TK-117), 2'-deoxy-5-fluoro-3',5'-bis-O-(4-methoxyphenoxycarbonyl)-3-(n-propoxybenzoyl)uridine (FF-707), ethyl(±)-6-t-butoxy-5-fluoro-2,4-dioxohexahydropyrimidine-γ-5-carboxylate (TAC-278), 1-phthalidyl-5-fluorouracil, 2'-deoxy-5-fluorouridine (FUDR), ethyl 5-fluoro-6-(e)-(2-furfurylidene-aminoxy)-1,2,3,4,5,6-hexahydro-2,4-dioxopyrimidine-5-carboxylate, ethyl 5-fluoro-6-(z)-(2-furfurylidene-aminoxy)-1,2,3,4,5,6-hexahydro-2,4-dioxopyrimidine-5-carboxylate and the like. Particularly preferable are 5-FU, 1-(2-tetrahydrofuranyl)-5-fluorouracil, 1-phthalidyl-5-fluorouracil, 5'-deoxy-5-fluorouracil, 5-fluorouridine, 2'-deoxy-5-fluorouridine, 1-n-hexylcarbamoyl-5-fluorouracil and the like.

When admixed with a 2'-deoxy-5-fluorouridine compound of the following formula (3) already developed by us and capable of producing 5-FU in vivo to exert an excellent anti-cancer activity, the pyridine derivatives of the formula (1) according to this invention can also increase the anti-cancer activity of the compound of the formula (3).

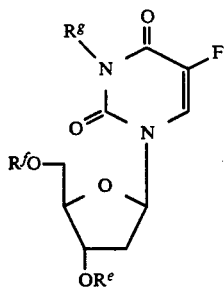

wherein one of $R^e$ and $R^f$ represents phenyl-lower alkyl optionally having a substituent selected from the group consisting of lower alkyl, lower alkoxy, halogen, carboxyl, lower alkoxycarbonyl and di(lower alkyl)amino on the phenyl ring, phenyl-lower alkyl group substituted with lower alkylenedioxy or phenyl on the phenyl ring, phenyl-lower alkenyl group or naphthyl-lower alkyl group, and the other of $R^e$ and $R^f$ represents hydrogen or acyl; $R^g$ represents hydrogen, acyl or tetrahydrofuranyl. Preferable examples of the above 2'-deoxy-5-fluorouridine compounds are 3'-O-benzyl-2'-deoxy-5-fluorouridine, 3-benzoyl-3'-O-benzyl-2'-deoxy-5-fluorouridine, 5'-O-acetyl-3'-O-benzyl-2'-deoxy-5-fluorouridine, 2'-deoxy-3'-O-(4-chlorobenzyl)-5-fluorouridine and the like.

Throughout the specification and claims lower alkyl, lower alkoxy, lower alkenyl and halogen are defined as follows:

a) Lower alkyl groups are $C_{1-6}$ alkyl groups such as methyl, ethyl, propyl, isopropyl, butyl, tert-butyl, pentyl, hexyl and the like.

b) Lower alkoxyl groups are $C_{1-6}$ alkoxyl groups such as methoxy, ethoxy, propoxy, isopropoxy, butoxy, tert-butoxy, pentyloxy, hexyloxy and the like.

c) Lower alkenyl groups are $C_{2-6}$ alkenyl groups such as vinyl, allyl, 2-butenyl, 3-butenyl, 1-methylallyl, 2-pentenyl, 2-hexenyl and the like.

d) Halogen atom is fluorine, chlorine, bromine, or iodine.

The substitutents in the formulas (1), (2-a), (2-b) and (3) are exemplified as follows:

1) Lower alkylcarbamoyl groups are alkylcarbamoyl groups having one or two $C_{1-6}$ alkyl groups such as N-methylcarbamoyl, N-ethylcarbamoyl, N-propylcarbamoyl, N-isopropylcarbamoyl, N-butylcarbamoyl, N-tert-butylcarbamoyl, N-pentylcarbamoyl, N-hexylcarbamoyl, N,N-dimethylcarbamoyl, N,N-diethylcarbamoyl, N,N-dipropylcarbamoyl, N-isopropyl-N-methylcarbamoyl, N-ethyl-N-methylcarbamoyl, N-methyl-N-pentyl-carbamoyl, N-propyl-N-pentylcarbamoyl, N,N-dipentylcarbamoyl, N-ethyl-N-hexylcarbamoyl, N-hexyl-N-pentylcarbamoyl, N,N-dihexylcarbamoyl and the like.

2) Phenylcarbamoyl groups optionally having a substituent on the phenyl ring are carbamoyl groups having one or two phenyl groups which may optionally have 1 to 3 substituents selected from the group consisting of halogen, lower alkoxyl and lower alkyl on the phenyl ring such as N-(2-chlorophenyl)carbamoyl, N-(3,5-dichlorophenyl)carbamoyl, N-(3-methoxyphenyl)-carbamoyl, N-(4-propoxyphenyl)carbamoyl, N-(2-methylphenyl)-carbamoyl, N-(4-ethylphenyl)-carbamoyl, N-(3-isopropylphenyl)carbamoyl, N-(4-hexylphenyl)carbamoyl, N-phenylcarbamoyl, N,N-diphenylcarbamoyl and the like.

3) Lower alkoxycarbonyl groups are carbonyl groups having $C_{1-6}$ alkoxyl group such as methoxycarbonyl, ethoxycarbonyl, propoxycarbonyl, isopropoxycarbonyl, tert-butoxycarbonyl, butoxycarbonyl, pentyloxycarbonyl, hexyloxycarbonyl and the like.

4) Lower alkoxy-lower alkyl groups are alkoxyalkyl groups in which the alkoxy moiety and alkyl moiety each have 1 to 6 carbon atoms, such as methoxymethyl, ethoxymethyl, propoxymethyl, butoxymethyl, tert-butoxymethyl, pentyloxymethyl, hexyloxymethyl, 2-methoxyethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl,2-pentyloxyethyl, 2-hexyloxyethyl and the like.

5) Lower alkoxycarbonyl-lower alkylcarbamoyl groups include carbamoyl groups substituted with one alkoxycarbonylalkyl group in which the alkoxy moiety and the alkyl moiety each have 1 to 6 carbon atoms, such as methoxycarbonylmethylcarbamoyl, ethoxycarbonylmethylcarbamoyl, propoxycarbonylmethylcarbamoyl, butoxycarbonylmethylcarbamoyl, tert-butoxycarbonylmethylcarbamoyl, pentyloxycarbonylmethylcarbamoyl, hexyloxycarbonylmethylcarbamoyl, 1-(methoxycarbonyl)ethylcarbamoyl, 2-(methoxycarbonyl)ethylcarbamoyl, 3-methoxycarbonylpropylcarbamoyl, 4-ethoxycarbonylbutylcarbamoyl, 6-propoxycarbonylhexylcarbamoyl, 5-isopropoxycarbonylpentylcarbamoyl, 1,1-dimethyl-2-butoxycarbonylethylcarbamoyl, 2-methyl-3-tert-butoxycarbonylpropylcarbamoyl, 2-pentyloxycarbonylethylcarbamoyl, 2-hexyloxycarbonylethylcarbamoyl and the like.

6) Lower alkylthio-lower alkyl groups include, for example, methylthiomethyl, ethylthiomethyl, propylthiomethyl, butylthiomethyl, tert-butylthiomethyl, pentylthiomethyl, hexylthiomethyl, methylthioethyl, methylthiopropyl, methylthiobutyl, methylthiopentyl, methylthiohexyl, ethylthioethyl, ethylthiobutyl, propylthiohexyl and the like.

7) Phenyl-lower alkoxy-lower alkyl groups are phenylalkoxyalkyl groups in which the alkyl moiety and alkoxy moiety each have 1 to 6 carbon atoms, such as benzyloxymethyl, 1-benzyloxyethyl, 2-benzyloxyethyl, 3-benzyloxypropyl, 4-benzyloxybutyl, 5-benzyloxypentyl, 6-benzyloxyhexyl, α-phenethyloxymethyl, β-phenethyloxymethyl, 3-phenylpropoxymethyl, 4-phenylbutyloxymethyl, 5-phenylpentyloxymethyl, 6-phenylhexylmethyl, 2-(β-phenethyloxy)ethyl, etc.

8) Tetrahydrofuranyl groups include, for example, 2-tetrahydrofuranyl, 3-tetrahydrofuranyl and the like.

9) Tetrahydropyranyl groups include, for example, 2-tetrahydropyranyl, 3-tetrahydropyranyl, 4-tetrahydropyranyl and the like.

10) Carboxy-lower alkylcarbamoyl groups are N-(carboxymethyl)carbamoyl, N-(2-carboxyethyl)carbamoyl, N-(3-carboxypropyl)carbamoyl, N-(2-methyl-2-carboxyethyl)carbamoyl, N-(4-carboxybutyl)carbamoyl, N-(2-methyl-3-carboxypropyl)carbamoyl, N-(2,2-dimethyl-2-carboxyethyl)carbamoyl, N-(5-carboxypentyl)carbamoyl, N-(6-carboxyhexyl)carbamoyl and the like.

11) Naphthyl-lower alkyl groups include, for example, α-naphthylmethyl, β-naphthylmethyl, 2-(α-naphthyl)ethyl, 3-(β-naphthyl)propyl, 4-(α-naphthyl)butyl, 5-(β-naphthyl)pentyl, 6-(α-naphthyl)hexyl, 30(α-naphthyl)2-methylpropyl, 1-(α-naphthyl)ethyl and the like.

12) Acyl group represented by $R^a$ or $R^{a'}$ of the compounds of formula (2-a) and acyl moiety of acyloxy group represented by $R^1$, $R^3$ or $R^5$ of the compounds of formula (1) are alkanoyl group having 1 to 20 carbon atoms and optionally substituted with phenyl-lower alkoxycarbonyl, lower alkylcarbamoyl, phenyl or phenoxy; arylcarbonyl group which may be optionally substituted with lower alkylenedioxy or with 1 to 3 substituents selected from the group consisting of halogen, lower alkyl, lower alkoxyl, nitro, phenyl-lower alkoxycarbonyl, carboxyl, hydroxy, guanidyl, phenyl-lower alkoxy and amino optionally substituted with lower alkyl; lower alkoxycarbonyl group; phenoxycarbonyl group; pyridylcarbonyl group; thienylcarbonyl group; furanylcarbonyl group and the like. More concrete examples of the alkanoyl and arylcarbonyl groups included in the above acyl group 12) are as follows:

i) Examples of alkanoyl group having 1 to 20 carbon atoms and optionally substituted with phenyl-lower alkoxycarbonyl, lower alkylcarbamoyl, phenyl or phenoxy are unsubstituted $C_{1-20}$ alkanoyl group such as formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, eicosanoyl and the like, and substituted $C_{1-20}$ alkanoyl group such as α-benzyloxycarbonylacetyl, 2-benzyloxycarbonylpropionyl, 3-benzyloxycarbonylpropionyl, 4-benzyloxycarbonylbutyryl, 5-benzyloxycarbonylpentanoyl, 6-benzyloxycarbonylhexanoyl, 3-(α-phenethyloxycarbonyl)propionyl, 3-(β-phenethyloxycarbonyl)propionyl, 5-(benzyloxycarbonyl)hexanoyl, 7-(benzyloxycarbonyl)heptanoyl, 8-(α-phenethyloxycarbonyl)octanoyl, 9-(β-phenethyloxycarbonyl)nonanoyl, 10-(benzyloxycarbonyl)decanoyl, 11-(β-phenethyloxycarbonyl)tridecanoyl, 15-(benzyloxycarbonyl)pentadecanoyl, 17-(benzyloxycarbonyl)heptadecanoyl, 20-(benzyloxycarbonyl)eicosanoyl, methylcarbamoylacetyl, ethylcarbamoylacetyl, propylcarbamoylacetyl, butylcarbamoylacetyl, tert-butylcarbamoylacetyl, pentylcarbamoylacetyl, hexylcarbamoylacetyl, methylcarbamoylpropionyl, ethylcarbamoylbutyryl, propylcarbamoylpentanoyl, ethylcarbamoylhexanoyl, ethylcarbamoylheptanoyl, methylcarbamoyloctanoyl, ethylcarbamoylnonanoyl, methylcarbamoyldecanoyl, methylcarbamoyltridecanoyl, ethylcarbamoylpentadecanoyl, methylcarbamoylheptadecanoyl, methylcarbamoyleicosanoyl, etc;

ii) Examples of arylcarbonyl group optionally having substituents selected from the group consisting of halogen atom, lower alkyl group, lower alkoxyl group, nitro group, phenyl-lower alkoxycarbonyl group, carboxyl group, lower-alkylenedioxy group, hydroxy group, guanidyl group and amino group optionally substituted with lower alkyl group are benzoyl, 2-chlorobenzoyl, 3-chlorobenzoyl, 4-chlorobenzoyl, 2-fluorobenzoyl, 4-fluorobenzoyl, 2-bromobenzoyl, 2,3-dichlorobenzoyl, 3,4-dichlorobenzoyl, 2,5-dichlorobenzoyl, 3,4,5-trichlorobenzoyl, 3,4-dibromobenzoyl, 3-bromobenzoyl, 2-methylbenzoyl, 3-methylbenzoyl, 2,3-dimethylbenzoyl, 4-methylbenzoyl, 3,4-dimethylbenzoyl, 2-ethylbenzoyl, 4-ethylbenzoyl, 3,4,5-trimethylbenzoyl, 3-propylbenzoyl, 2-butylbenzoyl, 4-pentylbenzoyl, 3-hexylbenzoyl, 2-methoxybenzoyl, 3-methoxybenzoyl, 3,5-dimethoxybenzoyl, 3,4-dimethoxybenzoyl, 3,4,5-trimethoxybenzoyl, 2,3-dimethoxybenzoyl, 4-methoxybenzoyl, 2-ethoxybenzoyl, 3-ethoxybenzoyl, 4-ethoxybenzoyl, 3-propoxybenzoyl, 4-butoxybenzoyl, 2-pentyloxybenzoyl, 3-hexyloxybenzoyl, 2-nitrobenzoyl, 2,4-dinitrobenzoyl, 4-nitrobenzoyl, 2-benzyloxycarbonylbenzoyl, 3-benzyloxycarbonylbenzoyl, 4-benzyloxycarbonylbenzoyl, 3-(α-phenethyloxycarbonyl)benzoyl, 4-(β-phenethyloxycarbonyl)benzoyl, 4-(3-phenylpropoxycarbonyl)benzoyl, 4-(6-phenylhexyloxycarbonyl)benzoyl, 2-carboxybenzoyl, 3-carboxybenzoyl, 4-carboxybenzoyl, 2,3-methylenedioxybenzoyl, 3,4-methylenedioxybenzoyl, 2,3-ethylenedioxybenzoyl, 3,4-ethylenedioxybenzoyl, 2-hydroxybenzoyl, 3-hydroxybenzoyl, 2,3-dihydroxybenzoyl, 3,4-dihydroxybenzoyl, 3,4,5-trihydroxybenzoyl, 4-hydroxybenzoyl, 2-guanidylbenzoyl, 3-guanidylbenzoyl, 4-guanidylbenzoyl, 2-aminobenzoyl, 3-aminobenzoyl, 4-aminobenzoyl, 2-methylaminobenzoyl, 3-methylaminobenzoyl, 4-methylaminobenzoyl, 2-ethylaminobenzoyl, 3-propylaminobenzoyl, 4-butylaminobenzoyl, 3-pentylaminobenzoyl, 4-hexylaminobenzoyl, 2-(N,N-dimethylamino)benzoyl, 3-(N,N-dimethylamino)benzoyl, 4-(N,N-dimethylamino)benzoyl, 3-(N-methyl-N-ethylamino)benzoyl, 4-(N,N-diethylamino)benzoyl, 3-(N,N-dipropylamino)benzoyl, 4-(N,N-dibutylamino)benzoyl, 4-(N,N-dipentylamino)benzoyl, 4-(N,N-dihexylamino)benzoyl, 2-(benzyloxy)benzoyl, 3-(benzyloxy)benzoyl, 4-(benzyloxy)benzoyl, 2-(α-phenethyloxy)- benzoyl, 3-(α-phenethyloxy)benzoyl, 4-(α-phenethyloxy)benzoyl, 2-(β-phenethyloxy)benzoyl, 3-(β-phenethyloxy)benzoyl, 4-(β-phenethyloxy)benzoyl, 4-(3-phenylpropoxy)benzoyl, 4-(4-phenylbutoxy)benzoyl, 4-(5-phenylpentyloxy)benzoyl, 4-(6-phenylhexyloxy)benzoyl, α-naphthylcarbonyl, β-naphthylcarbonyl, 2-chloro-1-naphthylcarbonyl, 4-chloro-1-naphthylcarbonyl, 6-chloro-1-naphthylcarbonyl, 8-chloro-1-naphthylcarbonyl, 5-fluoro-1-naphthylcarbonyl, 4-bromo-1-naphthylcarbonyl, 1-chloro-2-naphthylcarbonyl, 4-bromo-2-naphthylcarbonyl, 6-fluoro-2-naphthylcarbonyl, 4-methyl-1-naphthylcarbonyl, 5-ethyl-1-naphthylcarbonyl, 1-methyl-2-naphthylcarbonyl, 5-methyl-2-naphthylcarbonyl, 8-ethyl-2-naphthylcarbonyl, 4-methoxy-1-naphthylcarbonyl, 5-ethoxy-2-naphthylcarbonyl, 3-nitro-1-naphthylcarbonyl, 6-nitro-1-naphthylcarbonyl, 4-nitro-2-naphthylcarbonyl, 5-nitro-2-naphthylcarbonyl, 3-benzyloxycarbonyl-1-naphthylcarbonyl, 6-(α-phenethyloxycarbonyl)-1-naphthylcarbonyl, 4-benzyloxycarbonyl-2-naphthylcarbonyl, 5-(α-phenethyloxycarbonyl)-2-naphthylcarbonyl, 3-carboxy-1-naphthylcarbonyl, 6-carboxy-1-naphthylcarbonyl, 4-carboxy-2-naphthylcarbonyl, 5-carboxy-2-naphthylcarbonyl, 2,3-methylenedioxy-1-naphthylcarbonyl, 3,4-methylenedioxy-1-naphthylcarbonyl, 5,6-methylenedioxy-1-naphthylcarbonyl, 6,7-methylenedioxy-1-naphthylcarbonyl, 7,8-methylenedioxy-1-naphthylcarbonyl, 3,4-methylenedioxy-2-naphthylcarbonyl, 5,6-methylenedioxy-2-naphthylcarbonyl, 6,7-methylenedioxy-2-naphthylcarbonyl, 7,8-methylenedioxy-2-naphthylcarbonyl, 3,4-ethylenedioxy-1-naphthylcarbonyl, 5,6-ethylenedioxy-2-naphthylcarbonyl, 2-hydroxy-1-naphthylcarbonyl, 3-hydroxy-1-naphthylcarbonyl, 4-hydroxy-1-naphthylcarbonyl, 5-hydroxy-1-naphthylcarbonyl, 6-hydroxy-1-naphthylcarbonyl, 7-hydroxy-1-naphthylcarbonyl, 8-hydroxy-1-naphthylcarbonyl, 1-hydroxy-2-naphthylcarbonyl, 4-hydroxy-2-naphthylcarbonyl, 5-hydroxy-2-naphthylcarbonyl, 7-hydroxy-2-naphthylcarbonyl, 2-guanidyl-1-naphthylcarbonyl, 3-guanidyl-1-naphthylcarbonyl, 5-guanidyl-1-naphthylcarbonyl, 6-guanidyl-1-naphthylcarbonyl, 8-guanidyl-1-naphthylcarbonyl, 1-guanidyl-2-naphthylcarbonyl, 4-guanidyl-2-naphthylcarbonyl, 6-guanidyl-2-naphthylcarbonyl, 8-guanidyl-2-naphthylcarbonyl, 2-amino-1-naphthylcarbonyl, 3-amino-1-naphthylcarbonyl, 4-amino-1-naphthylcarbonyl, 6-amino-1-naphthylcarbonyl, 4-amino-2-naphthylcarbonyl, 5-amino-1-naphthylcarbonyl, 7-amino-2-naphthylcarbonyl, 8-amino-2-naphthylcarbonyl, 3-(N,N-dimethylamino)-2-naphthylcarbonyl, 4-(N-methyl-N-ethylamino)-1-naphthylcarbonyl, 6-(N,N-dimethylamino)-1-naphthylcarbonyl, 7-(N-methyl-N-ethylamino)-2-naphthylcarbonyl, 8-(N-methyl-N-ethylamino)-1-naphthylcarbonyl, 2-pyridylcarbonyl, 3-pyridylcarbonyl, 4-pyridylcarbonyl, 2-thienylcarbonyl, 3-thienylcarbonyl, 2-furanylcarbonyl, 3-furanylcarbonyl, and the like.

13) Lower alkanoyloxy groups include, for example, formyloxy, acetyloxy, propionyloxy, butyryloxy, isobutyryloxy, pentanoyloxy, hexanoyloxy and the like.

14) Phenyl-lower alkoxyl groups include, for example, phenylmethoxy, 1-phenylethoxy, 2-phenylethoxy, 1-phenypropoxy, 2-phenylpropoxy, 3-phenylpropoxy, 3-phenylbutoxy, 4-phenylbutoxy, 5-phenylpentyloxy, 6-phenylhexyloxy and the like.

15) Phenyl-lower alkyl groups represented by $R^e$ and $R^f$ of the compounds of the formula (3) and optionally having substituents selected from the group consisting of lower alkyl, lower alkoxyl, halogen and carboxyl on the phenyl ring include, for example, benzyl, 2-methylbenzyl, 3-methylbenzyl, 4-methylbenzyl, 2-ethylbenzyl, 3-ethylbenzyl, 4-ethylbenzyl, 2-propylbenzyl, 3-propylbenzyl, 4-propylbenzyl, 2-butylbenzyl, 3-butylbenzyl, 4-butylbenzyl, 2-tert-butylbenzyl, 3-tert-butylbenzyl, 4-tert-butylbenzyl, 2-pentylbenzyl, 3-pentylbenzyl, 4-pentylbenzyl, 2-hexylbenzyl, 3-hexylbenzyl, 4-hexylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2,3,4-trimethylbenzyl, 2,4,5-trimethylbenzyl, 2,3,5-trimethylbenzyl, 2,4,6-trimethylbenzyl, 3,4,5-trimethylbenzyl, 2,3-diethylbenzyl, 2,4-diethylbenzyl, 2,5-diethylbenzyl, 2,6-diethylbenzyl, 2,4,6-triethylbenzyl, 2,4-dipropylbenzyl, 3,4,5-triethylbenzyl, 3-methyl-4-ethylbenzyl, 1-phenylethyl, 2-phenylethyl, 2-phenyl-1-methylethyl, 1-(2-methylphenyl)ethyl, 2-(2-methylphenyl)ethyl, 2-(3methylphenyl)ethyl, 2-(4-methylphenyl)ethyl, 1-(2,4-dimethylphenyl)ethyl, 2-(2,4-dimethylphenyl)ethyl, 1-(2,4,6-trimethylphenyl)ethyl, 2-(2,4,6-trimethylphenyl)ethyl, 3-phenylpropyl, 3-(4-methylphenyl)propyl, 4-phenylbutyl, 4-(2-methylphenyl)butyl, 5-phenylpentyl, 5-(3-methylphenyl)phenyl, 6-phenylhexyl, 6-(4-methylphenyl)hexyl, 2-methoxybenzyl, 3-methoxybenzyl, 4-methoxybenzyl, 2,3-dimethoxybenzyl, 2,4-dimethoxybenzyl, 2,5-dimethoxybenzyl, 3-methoxy-4-ethoxybenzyl, 2,6-dimethoxybenzyl, 3,4-dimethoxybenzyl, 3,5-dimethoxybenzyl, 2,3,4-trimethoxybenzyl, 2,4,5-trimethoxybenzyl, 2,3,5-trimethoxybenzyl, 2,4,6-trimethoxybenzyl, 3,4,5-trimethoxybenzyl, 2-ethoxybenzyl, 4-propoxybenzyl, 3-butoxybenzyl, 2-tert-butoxybenzyl, 3-pentyloxybenzyl, 4-hexyloxybenzyl, 2,3-diethoxybenzyl, 1-(4-methoxyphenyl)ethyl, 2-(3,4-dimethoxyphenyl)ethyl, 3-(4-methoxyphenyl)propyl, 4-(2-methoxyphenyl)butyl, 5-(4-methoxyphenyl)pentyl, 6-(4-methoxyphenyl)hexyl, 6-(3,4,5-tripentyloxyphenyl)hexyl, 2-fluorobenzyl, 3-fluorobenzyl, 4-fluorobenzyl, 2,3-difluorobenzyl, 2,4-difluorobenzyl, 2,5-difluorobenzyl, 2-fluoro-3-chlorobenzyl, 2-fluoro-3-bromobenzyl, 2,6-difluorobenzyl, 2,3,4-trifluorobenzyl, 2,4,5-trifluorobenzyl, 2,3,5-trifluorobenzyl, 2,4,6-trifluorobenzyl, 3,4,5-trifluorobenzyl, 1-(2-fluorophenyl)ethyl, 2-(2-fluorophenyl)ethyl, 3-(3-fluorophenyl)propyl, 4-(2-fluorophenyl)butyl, 5-(2-fluorophenyl)pentyl, 6-(3-fluorophenyl)hexyl, 2-bromobenzyl, 3-bromobenzyl, 4-bromobenzyl, 2,3-dibromobenzyl, 2-bromo-3-fluorobenzyl, 2-fluoro-4-bromobenzyl, 2,4-dibromobenzyl, 2,5-dibromobenzyl, 2,6-dibromobenzyl, 2,3,4-tribromobenzyl, 2,4,5-tribromobenzyl, 2,3,5-tribromobenzyl, 2,4,6-tribromobenzyl, 3,4,5-tribromobenzyl, 1-(2-bromophenyl)ethyl, 2-(2-bromophenyl)ethyl, 3-(2-bromophenyl)propyl, 4-(3-bromophenyl)-butyl, 5-(2-bromophenyl)pentyl, 6-(4-bromophenyl)hexyl, 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 2-bromo-4-chlorobenzyl, 2-fluoro-4-chlorobenzyl, 2,3,4-trichlorobenzyl, 2,4,5-trichlorobenzyl, 2,3,5-trichlorobenzyl, 2,4,6-trichlorobenzyl, 3,4,5-trichlorobenzyl, 1-(4-chlorophenyl)ethyl, 2-(4-chlorophenyl)ethyl, 3-(2-chlorophenyl)propyl, 4-(4-chlorophenyl)butyl, 5-(3-chlorophenyl)pentyl, 6-(4-chlorophenyl)hexyl, 2-(3,4-dichlorophenyl)ethyl, 2-iodobenzyl, 3-iodobenzyl, 4-iodobenzyl, 3,4-diiodobenzyl, 3,4,5-triiodobenzyl, 2-(3-iodophenyl)ethyl, 6-(2-iodophenyl)hexyl, 2-carboxybenzyl, 3-carboxybenzyl, 4-carboxybenzyl, 2,4-dicarboxybenzyl, 3,5-dicarboxybenzyl, 2,6-dicarboxybenzyl, 2,4,6-tricarboxybenzyl, 3,4,5-tricarboxybenzyl, 2-(2-carboxyphenyl)ethyl, 2-(3- carboxyphenyl)ethyl, 2-(4-carboxyphenyl)ethyl, 2-(2,4-dicarboxyphenyl)ethyl, 2-(2,4,6-tricarboxyphenyl)ethyl, 1-(4-carboxyphenyl)ethyl, 1-(2,4,6-tricarboxyphenyl)ethyl, 3-(2-carboxyphenyl)propyl, 3-(3-carboxyphenyl)propyl, 3-(4-carboxyphenyl)propyl, 3-(2,4-dicarboxyphenyl)propyl, 3-(3,4,5-tricarboxyphenyl)propyl, 3-(2,4,6-tricarboxyphenyl)propyl, 2-(4-carboxyphenyl)propyl, 4-(2-carboxyphenyl)butyl, 4-(3-carboxyphenyl)butyl, 4-(4-carboxyphenyl)butyl, 4-(2,4-dicarboxyphenyl)butyl, 4-(2,4,6-tricarboxyphenyl)butyl, 5-(4-carboxyphenyl)pentyl, 5-(3,4-dicarboxyphenyl)pentyl, 5-(3,4,5-tricarboxyphenyl)pentyl, 6-(3-carboxyphenyl)hexyl, 6-(2,4-dicarboxyphenyl)hexyl, 6-(2,4,6-tricarboxyphenyl)hexyl, etc.

16) Phenyl lower alkyl groups having lower alkylenedioxy groups or phenyl groups as the substituents are, for example, phenyl-lower alkyl groups in which phenyl group substituted with $C_1C_4$ alkylenedioxy or with phenyl group is linked with $C_1C_6$ alkylene groups, such as 2,3-methylenedioxybenzyl, 3,4-methylenedioxybenzyl, 2,3-ethylenedioxybenzyl, 3,4-ethylenedioxybenzyl, 3,4-trimethylenedioxybenzyl, 3,4-tetramethylenedioxybenzyl, 1-(3,4-methylenedioxyphenyl)ethyl, 2-(3,4-methylenedioxyphenyl)ethyl, 3-(3,4-methylenedioxyphenyl)propyl, 4-(3,4-methylenedioxyphenyl)butyl, 5-(3,4-methylenedioxyphenyl)pentyl, 6-(3,4-methylenedioxyphenyl)hexyl, 3-(3,4-trimethylenedioxyphenyl)propyl, 2-phenylbenzyl, 3-phenylbenzyl, 4-phenylbenzyl, 2-(3-phenylphenyl)-ethyl, 1-(4-phenylphenyl)ethyl, 2-(4-phenylphenyl)-ethyl, 3-(4-phenylphenyl)propyl, 4-(4-phenylphenyl)-butyl, 5-(4-phenylphenyl)pentyl, 6-(4-phenylphenyl)-hexyl, and the like.

17) Acyl groups represented by $R^e$, $R^f$ and $R^g$ of the compound of formula (3) include the following:

(i) $C_1$-$C_{20}$ alkanoyl groups optionally substituted with the substituents selected from the group consisting of halogen, hydroxy, lower alkoxy, aryloxy, and substituted or unsubstituted aryl. Examples thereof are $C_1$-$C_{20}$ unsubstituted alkanoyl groups such as formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, eicosanoyl, etc; $C_2$-$C_6$ alkanoyl groups substituted with 1 to 3 halogen atoms such as monochloroacetyl, monobromoacetyl, dichloroacetyl, trichloroacetyl, 3-chloropropionyl, 4-chlorobutyryl, 5-chloropentanoyl, 6-chloropentanoyl, etc; $C_2$-$C_6$ alkanoyl groups substituted with hydroxy group such as hydroxyacetyl, 3-hydroxypropionyl, 5-hydroxypentanoyl, 4-hydroxybutanoyl, 6-hydroxyhexanoyl, etc; $C_2$-$C_6$ alkanoyl groups substituted with lower alkoxy group such as methoxyacetyl, ethoxyacetyl, 3-propoxypropionyl, 6-hexyloxyhexanoyl, 3-methoxypropionyl, etc; $C_2$-$C_6$ alkanoyl groups substituted with phenoxy or naphthyloxy group such as phenoxyacetyl, 2-phenoxypropionyl, 3-phenoxypropionyl, 4-phenoxybutyryl, 5-phenoxypentanoyl, 6-phenoxyhexanoyl, α-naphthyloxyacetyl, etc; $C_2$-$C_6$ alkanoyl groups substituted with aryl group optionally substituted with 1 to 3 substituents selected from the group consisting of halogen atom, lower alkyl group, lower alkoxyl group, carboxyl group, lower alkoxycarbonyl group, nitro group and cyano group on the aryl ring (phenyl ring, naphthyl ring, etc.), such as α-phenylacetyl, 2-phenylpropionyl, 3-phenylpropionyl, 4-phenylbutyryl, 5-phenylpentanoyl, 6-phenylhexanoyl, α-(2-chlorophenyl)acetyl, α-(4-methylphenyl)acetyl, α-(3,4,5-trimethoxyphenyl)-acetyl, α-(3,4-dimethoxyphenyl)acetyl, 6-(4-carboxyphenyl)hexanoyl, 4-(4-ethoxycarbonylphenyl)pentanoyl, α-(4-nitrophenyl)acetyl, α-(4-cyanophenyl)acetyl, α-naphthylacetyl, β-naphthylacetyl, etc;

(ii) Aryl-carbonyl groups optionally having lower alkylenedioxy group or 1 to 3 substituents selected from the group consisting of halogen atom, lower alkyl group, lower alkoxyl group, carboxyl, group, lower alkoxycarbonyl group, nitro group and cyano group on the aryl ring. Examples thereof are aryl-carbonyl groups such as phenylcarbonyl, naphthylcarbonyl, etc. optionally having lower alkylenedioxy group or 1 to 3 substituents selected from the group consisting of halogen atom, lower alkyl group, lower alkoxyl group, carboxyl group, nitro group, cyano group, and lower alkoxycarbonyl groups, such as benzoyl, α-naphthylcarbonyl, β-naphthylcarbonyl, 2-methylbenzoyl, 3-methylbenzoyl, 4-methylbenzoyl, 2,4-dimethylbenzoyl, 3,4,5-trimethylbenzoyl, 4-ethylbenzoyl, 2-methoxybenzoyl, 3-methoxybenzoyl, 4-methoxybenzoyl, 2,4-dimethoxybenzoyl, 3,4,5-trimethoxybenzoyl, 4-ethoxybenzoyl, 2-methoxy-4-ethoxybenzoyl, 2-propoxybenzoyl, 3-propoxybenzoyl, 4-propoxybenzoyl, 2,4-dipropoxybenzoyl, 3,4,5-tripropoxybenzoyl, 2-carboxybenzoyl, 3-carboxybenzoyl, 4-carboxybenzoyl, 2-chlorobenzoyl, 3-chlorobenzoyl, 4-chlorobenzoyl, 2,3-dichlorobenzoyl, 2,4,6-trichlorobenzoyl, 2-bromobenzoyl, 4-fluorobenzoyl, 2-methoxycarbonylbenzoyl, 3-methoxycarbonylbenzoyl, 4-methoxycarbonylbenzoyl, 2-ethoxycarbonylbenzoyl, 3-ethoxycarbonylbenzoyl, 4-ethoxycarbonylbenzoyl, 2-propoxycarbonylbenzoyl, 3-propoxycarbonylbenzoyl, 4-propoxycarbonylbenzoyl, 2-isopropoxycarbonylbenzoyl, 3-isopropoxycarbonylbenzoyl, 4-isopropoxycarbonylbenzoyl, 2-butoxycarbonylbenzoyl, 3-butoxycarbonylbenzoyl, 4-butoxycarbonylbenzoyl, 2-tert-butoxycarbonylbenzoyl, 3-tert-butoxycarbonylbenzoyl, 4-tert-butoxycarbonylbenzoyl, 2-pentyloxycarbonylbenzoyl, 3-pentyloxycarbonylbenzoyl, 4-pentyloxycarbonylbenzoyl, 2-hexyloxycarbonylbenzoyl, 3-hexyloxycarbonylbenzoyl, 4-hexyloxycarbonylbenzoyl, 3,5-dimethoxycarbonylbenzoyl, 3,4,5-trimethoxycarbonylbenzoyl, β-methyl-α-naphthylcarbonyl, α-methoxy-β-naphthylcarbonyl, β-chloro-α-naphthylcarbonyl, 2-cyanobenzoyl, 4-cyanobenzoyl, 2-nitrobenzoyl, 4-nitrobenzoyl, 3,4-methylenedioxybenzoyl, 3,4-ethylenedioxybenzoyl, 2,3-methylenedioxybenzoyl, etc.

(iii) 5- or 6- Membered unsaturated hetero ring-carbonyl groups having nitrogen atom, sulfur atom or oxygen atom as the hetero atom.

Examples thereof are thienylcarbonyl, furanylcarbonyl, thiazolylcarbonyl, quinolylcarbonyl, pyrazinylcarbonyl, pyridylcarbonyl, etc., such as 2-thienylcarbonyl, 3-thientylcarbonyl, 2-furanylcarbonyl, 3-furanylcarbonyl, 4-thiazolylcarbonyl, 2-quinolylcarbonyl, 2-pyrazinylcarbonyl, 2-pyridylcarbonyl, 3-pyridylcarbonyl, 4-pyridylcarbonyl, etc.

(iv) Carbonic acid ester residue such as aryloxycarbonyl groups, straight or branched-chain or cyclic alkoxycarbonyl groups.

Examples thereof are aryloxycarbonyl groups optionally substituted with 1 to 3 substituents selected from the group consisting of halogen atom, lower alkyl group and lower alkoxyl group on the aryl ring (phenyl ring, naphthyl ring, etc.), such as phenoxycarbonyl, α-naphthyloxycarbonyl, β-naphthyloxycarbonyl, 2-methylphenoxycarbonyl, 3-methylphenoxycarbonyl, 4-methylphenoxycarbonyl, 2,4-dimethylphenoxycarbonyl, 3,4,5-trimethylphenoxycarbonyl, 4-ethylphenoxycarbonyl, 2-methoxyphenoxycarbonyl, 3-methoxyphenoxycarbonyl, 4-methoxyphenoxycarbonyl, 2,4-dimethoxyphenoxycarbonyl, 3,4,5-trimethoxyphenoxycarbonyl, 4-ethoxyphenoxycarbonyl, 2-propoxyphenoxycarbonyl, 3-propoxyphenoxycarbonyl, 4-propoxyphenoxycarbonyl, 2,4-dipropoxyphenoxycarbonyl, 3,4,5-tripropoxyphenoxycarbonyl, 2-chlorophenoxycarbonyl, 3-chlorophenoxycarbonyl, 4-chlorophenoxycarbonyl, 2,3-dichlorophenoxycarbonyl, 2,4,6-trichlorophenoxycarbonyl, 2-bromophenoxycarbonyl, 4-fluorophenoxycarbonyl, $\beta$-methyl-$\alpha$-naphthyloxycarbonyl, $\alpha$-methoxy-$\beta$naphthyloxycarbonyl, $\beta$-chloro-$\alpha$-naphthyloxycarbonyl etc; straight or branched-chain or cyclic alkoxycarbonyl groups having 1 to 8 carbon atoms in the alkoxy moiety, such as methoxycarbonyl, ethoxycarbonyl, propoxycarbonyl, isopropoxycarbonyl, tert-butoxycarbonyl, butoxycarbonyl, pentyloxycarbonyl, hexyloxycarbonyl, cyclopropyloxycarbonyl, cyclobutyloxycarbonyl, cyclopentyloxycarbonyl, cyclohexyloxycarbonyl, cycloheptyloxycarbonyl, cyclooctyloxycarbonyl, etc.

(v) substituted or unsubstituted cycloalkyl carbonyl groups.

Examples thereof are cycloalkylcarbonyl groups optionally substituted with halogen atom, hydroxy group, lower alkoxyl group or lower alkyl group and having 3 to 8 carbon atoms in the cycloalkyl ring, such as cyclopropylcarbonyl, cyclobutylcarbonyl, cyclopentylcarbonyl, cyclohexylcarbonyl, cycloheptylcarbonyl, cyclooctylcarbonyl, 2-chlorocyclohexylcarbonyl, 3-hydroxycyclopentylcarbonyl, 3-methylcyclohexylcarbonyl, 4-methoxycyclohexylcarbonyl, etc.

(vi) lower alkenyl (or lower alkynyl)carbonyl groups.

Examples thereof are carbonyl groups having $C_2$-$C_6$ alkenyl or alkynyl group, such as vinylcarbonyl, allylcarbonyl, 2-butenylcarbonyl, 3-butenylcarbonyl, 1-methylallylcarbonyl, 2-pentenylcarbonyl, 3-hexenylcarbonyl, ethynylcarbonyl, propynylcarbonyl, 2-butynylcarbonyl, 1-methyl-3-pentynylcarbonyl, 4-hexynylcarbonyl, etc.

18) Lower alkylenedioxy groups include, for example, $C_{1-4}$ alkylenedioxy groups such as methylenedioxy, ethylenedioxy, trimethylenedioxy, tetramethylenedioxy, etc.

19) Aryloxycarbonyloxy groups optionally having 1 to 3 substituents such as lower alkyl, lower alkoxy or halogen on the phenyl ring include 2-methylphenoxycarbonyloxy, 3-methylphenoxycarbonyloxy, 4-methylphenoxycarbonyloxy, 4-ethylphenoxycarbonyloxy, 4-t-butylphenoxycarbonyloxy, 4-hexylphenoxycarbonyloxy, 2,4-dimethylphenoxycarbonyloxy, 2,4,6-trimethylphenoxycarbonyloxy, 2-methoxyphenoxycarbonyloxy, 3-methoxyphenoxycarbonyloxy, 4-methoxyphenoxycarbonyloxy, 4-ethoxyphenoxycarbonyloxy, 4-propoxyphenoxycarbonyloxy, 4-butoxyphenoxycarbonyloxy, 4-pentyloxyphenoxycarbonyloxy, 4-hexyloxyphenoxycarbonyloxy, 2,4-dimethoxyphenoxycarbonyloxy, 2,4,6-trimethoxyphenoxycarbonyloxy, 2-fluorophenoxycarbonyloxy, 3-chlorophenoxycarbonyloxy, 4-bromophenoxycarbonyloxy, 2,4-dichlorophenoxycarbonyloxy, 2,4,6-tribromophenoxycarbonyloxy and the like.

20) Aroyloxy groups include benzoyloxy, 1-naphthoyloxy, 2-naphthoyloxy and the like.

21) Aroyloxy groups having 1 to 3 substituents such as lower alkyl, lower alkoxy, halogen or nitro on the phenyl ring include 2-chlorobenzoyloxy, 3-chlorobenzoyloxy, 4-chlorobenzoyloxy, 2,4-dichlorobenzoyloxy, 3,4,5-trichlorobenzoyloxy, 2-fluorobenzoyloxy, 4-fluorobenzoyloxy, 4-bromobenzoyloxy, 2-methylbenzoyloxy, 3-methylbenzoyloxy, 4-methylbenzoyloxy, 2,4-dimethylbenzoyloxy, 2,4,6-trimethylbenzoyloxy, 4-ethylbenzoyloxy, 4-butylbenzoyloxy, 4-methyl-1-naphthoyloxy, 2-nitrobenzoyloxy, 3-nitrobenzoyloxy, 4-nitrobenzoyloxy, 2,4-dinitrobenzoyloxy, 3,4-dinitrobenzoyloxy, 4-nitro-1-naphthoyloxy, 2-methoxybenzoyloxy, 3-methoxybenzoyloxy, 4-methoxybenzoyloxy, 3,4,5-trimethoxybenzoyloxy, 4-ethoxybenzoyloxy, 4-butoxybenzoyloxy, 4-methoxy-1-naphthoyloxy and the like.

22) Alkylidene moieties of alkylidenedioxy groups include methylene, ethylidene, propylidene, butylidene, pentylidene, hexylidene and the like.

23) Arylidene moieties of arylidenedioxy groups include bendylidene, 1-phenylethylidene, 1-naphthylmethylene, 2-naphthylmethylene and the like.

24) Lower alkoxycarbonyl groups include $C_2$-$C_7$ straight or branched chain alkoxycarbonyl groups such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc.

25) Di(lower alkyl)amino groups include dimethylamino, methylethylamino, etc.

26) Phenyl-lower alkenyl groups include phenyl $C_2$-$C_6$ alkenyl groups such as 2-phenylethylenyl, 3-phenyl-1-propenyl, 3-phenyl-2-propenyl, 4-phenyl-1-butenyl, 4-phenyl-2-butenyl, 4-phenyl-3-butenyl, 5-phenyl-4-pentenyl, 6-phenyl-5-hexenyl, etc.

27) Phenyl-lower alkoxy-lower alkoxy groups include phenylalkoxyalkoxy groups in which the alkoxy moieties have 1 to 6 carbon atoms, such as 1-benzyloxymethoxy, 1-benzyloxyethoxy, 2-benzyloxyethoxy, 3-benzyloxypropoxy, 4-benzyloxybutoxy, 5-benzyloxypentoxy, 6-benzyloxyhexyloxy, $\alpha$-phenethyloxymethoxy, $\beta$-phenethyloxymethoxy, 3-phenylpropoxymethoxy, 4-phenylbutyloxymethoxy, 5-phenylpentyloxymethoxy, 6-phenylhexylmethoxy, 2-($\beta$-phenethyloxy)ethoxy, etc.

Processes for preparing the pyridine derivatives to be used in this invention will be described below in detail.

The pyridine derivatives of this invention can be prepared, for example, by the processes as shown below in Reaction schemes-a to -h.

The pyridine compounds having the formula (1) in which at least one of $R^1$, $R^3$ and $R^5$ is acyloxy group can be prepared by acylating the corresponding compounds having hydroxy group corresponding to the acyloxy group. Preferred example thereof is shown in the reaction scheme-a below.

Reaction scheme-a

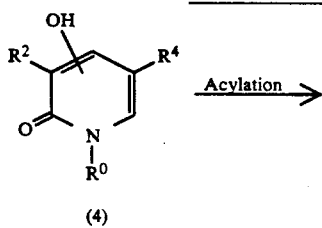

(4)

-continued
Reaction scheme-a

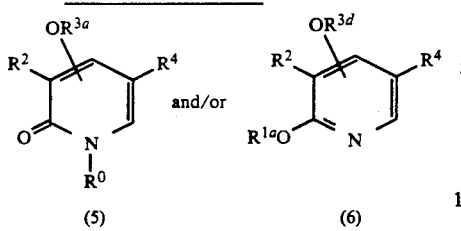

wherein $R^2$ and $R^4$ are as defined above, $R^{1a}$ and $R^{3a}$ are each acyl, $R^0$ is hydrogen atom, lower alkyl, tetrahydrofuranyl, tetrahydropyranyl, lower alkoxy-lower alkyl, phthalidyl, carbamoyl, lower alkoxy-carbonyl-lower alkyl-carbamoyl, phenyl-lower alkoxy-lower alkyl, phenyl-carbamoyl which may have substituent on the phenyl ring, lower alkyl-carbamoyl, carboxy-lower alkyl-carbamoyl, lower alkyl-thio-lower alkyl or lower alkenyl, and $R^{3d}$ is hydrogen or acyl.

According to this process the free hydroxyl group of a compound (4) is acylated. The acylation can be carried out by conventional methods usually employed for acylation. For example, any of the acid halide method, acid anhydride method, mixed acid anhydride method and N,N-dicyclohexylcarbodiimide method (DCC method) is available in this invention. Of these methods, the acid halide method, acid anhydride method and N,N-dicyclohexylcarbodiimide method (DCC method) are advantageously conducted.

According to the acid halide method, an acyl halide is reacted with the compound (4) in a suitable solvent in the presence of an acid scavenger to afford the desired compound (5) or compound (6). Acyl halides which can be used in the acylation can be any of fluoride, chloride, bromide and iodide of the acyl group to be introduced. Examples of useful acid scavengers are sodium carbonate, potassium carbonate, pyridine, trimethylamine, triethylamine, dimethylaniline, diethylaniline, etc. Solvents useful in the process can be any of those which do not adversely affect the reaction and which include, for example, aromatic hydrocarbons such as benzene, toluene, etc.; halogenated hydrocarbons such as methylene chloride, chloroform, carbon tetrachloride, etc.; ethers such as diethyl ether, dioxane, tetrahydrofuran, etc.; and other solvents such as ethyl acetate, N,N-dimethylformamide, acetone, acetonitrile, pyridine, dimethyl sulfoxide, etc. The amount of the acyl halide to be used may be at least about 0.5 mole, preferably about 0.5 to about 5 moles, per mole of the compound (4). The use of 0.5 to 1.5 moles of the acyl halide affords monoacyloxy product (5) and the use of over 1.5 moles leads to diacyloxy product (6). The reaction is carried out at a temperature of ice cooling to approximately the boiling point of the solvent, preferably room temperature to about 80° C., and is completed in about 5 minutes to about 50 hours, preferably about 3 to about 15 hours. Also usable as the starting material are the compounds in which the hydrogen atom of free hydroxyl group in the compound (4) is substituted with alkali metal.

The acid anhydride method can be performed by heating the compound (4) and an acid anhydride in a suitable solvent. Useful acid anhydrides are those which correspond with the acyl group to be introduced and which include, for example, acetic anhydride, propionic anhydride, butyric anhydride, benzoic anhydride, etc. The amount of the acid anhydride to be used is at least 0.5 mole, preferably about 1 to about 3 moles, per mole of the compound (4). The reaction can be conducted under the conditions including solvents, reaction temperature and reaction time which are similar to those in the acid halide method stated hereinbefore.

The N,N-dicyclohexylcarbodiimide method (DCC method) is effected by heating the compound (4) and a carboxylic acid in a suitable solvent in the presence of a condensing agent. Useful carboxylic acids are those which correspond with the acyl group to be introduced and which include, for example, acetic acid, propionic acid, butyric acid, benzoic acid, etc. Exemplary of the condensing agent are N,N-dialkylcarbodiimide (N,N-dicyclohexylcarbodiimide, etc.) and the like. The other reaction conditions similar to those in the acid halide method can be employed in this method.

The compound (5) obtained above can be also made into a compound (6) by repeating the foregoing acylation.

The pyridine compounds having the formula (1) in which the nitrogen atom at the 1-position on the pyridine ring has a group $-CONHR^6$ ($R^6$ is as defined below) as a substituent can be prepared by reacting an isocyanate compound ($R^6NCO$) with the corresponding compounds in which at least one of $R^1$, $R^2$ and $R^3$ is hydroxy and the nitrogen atom at 1-position has no substituent. Preferred example thereof is shown in the reaction scheme-b below.

Reaction scheme-b

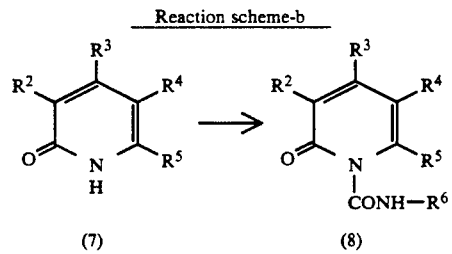

wherein $R^2$, $R^3$, $R^4$ and $R^5$ are as defined above and $R^6$ is hydrogen atom, lower alkoxycarbonyl-lower alkyl, phenyl which may have substituent on the phenyl ring, carboxy-lower alkyl or lower alkyl.

In this process, an isocyanate compound ($R^6NCO$) is caused to act on a compound (7) in a suitable solvent in the presence of a basic compound to obtain a compound (8). Preferable examples of the isocyanate compounds are lower alkyl isocyanates. Examples of the basic compound useful in this reaction are triethylamine and like amines, sodium carbonate, potassium carbonate and like alkali metal carbonates, pyridine, etc. The amount of isocyanate compound to be used is at least about 0.5 mole, preferably about 1.0 to about 2.0 moles, per mole of the compound (7). The reaction can be conducted under the conditions including solvents, reaction temperature and reaction time which are similar to those used in the acid chloride method of the Reaction scheme-a.

Of the compounds (7) used as the starting material in the reaction, those in which $R^3$ and (or) $R^5$ are acyloxy can be produced by subjecting a compound having hydroxy group as $R^3$ and (or) $R^5$ to the acylation in accordance with the reaction shown in Reaction scheme-a.

The compound (8) wherein $R^6$ is carboxy-lower alkyl can be also prepared by subjecting the corresponding compound (8) with lower alkoxycarbonyl-lower alkyl as $R^6$ to a usual hydrolysis.

Reaction scheme-c

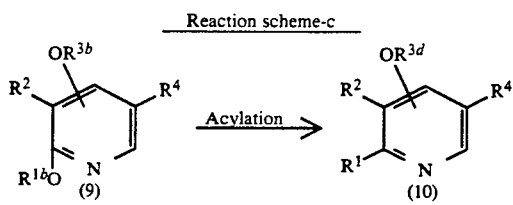

wherein $R^1$, $R^2$, $R^{3d}$ and $R^4$ are as defined above, $R^{1b}$ and $R^{3b}$ are each tri-lower alkylsilyl, and $R^1$ and $R^{3d}$ must not be hydroxy group at the same time.

In this process, an acyl halide is allowed to act on bis(tri-lower alkylsilyloxy)pyridine derivative (9) to give the desired acyloxy compound (10). Solvents useful in the reaction can be any of those which do not adversely affect the reaction and which include, for example, halogenated hydrocarbons such as methylene chloride, chloroform and carbon tetrachloride, etc.; aromatic hydrocarbons such as acetonitrile, benzene and toluene, etc.; ethers such as dioxane, tetrahydrofuran, diethyl ether, etc. Acyl halides useful in the reaction can be any of fluoride, chloride, bromide and iodide of the acyl group to be introduced. The amount of the acyl halide to be used is at least 0.5 mole per mole of the compound (9). In preparing a monoacyloxy product, it is preferred to use 0.5 to 1.5 moles of the acyl halide per mole of the compound (9). The content of acyl halide in excess of 1.5 moles affords a diacyloxy product. The reaction is usually carried out at room temperature to nearly the boiling point of the solvent and completed in about 10 minutes to about 30 hours, preferably about 1 to about 6 hours.

The reaction can be also effected in the presence of a Lewis acid, ammonia or amine in a catalytic amount. In the presence or absence of a Lewis acid, a 4-monoacyloxy product can be produced by the reaction as the main product, while in the presence of ammonia or amine, a 2-monoacyloxy product can be obtained as such. Exemplary of Lewis acids are stannic chloride, aluminum chloride, etc. and representative of amines are primary, secondary and tertiary amines such as monomethylamine, dimethylamine, trimethylamine, etc.

Reaction scheme-d

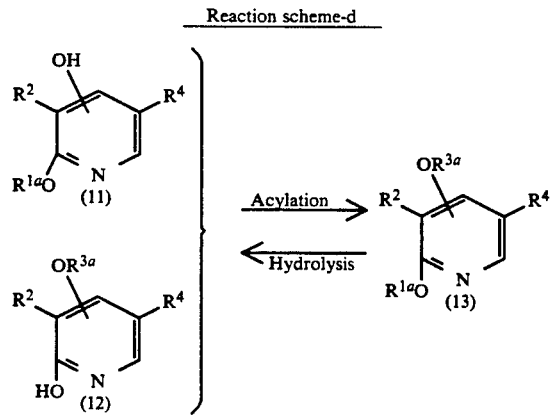

wherein $R^{1a}$, $R^2$, $R^{3a}$ and $R^4$ are as defined above. The acylation of a compound (11) or compound (12) in this process can be performed in the same manner as in the acylation in Reaction scheme-a.

The hydrolysis of a compound (13) (diacyloxy product) can be effected under acidic or basic conditions. Under acidic conditions, the hydrolysis can be performed by causing at least 0.5 mole of a protic compound to act on the compound (13), examples of the protic compound being water, alcohol, phenol and the like compounds having hydroxyl group, methyl mercaptan, ethyl mercaptan and like thiols, monomethylamine, dimethylamine, aniline and like primary and secondary amines, etc. The protic compound present in the system can be used as the solvent. It is also possible to conjointly use a solvent capable of being homogeneously mixed with the protic compound, such as acetone, acetonitrile, ethyl acetate, ethers such as diethyl ether, dioxane, tetrahydrofuran and the like, halogenated hydrocarbons such as methylene chloride, chloroform and the like, aromatic hydrocarbons such as benzene, toluene and the like, etc. The reaction can be conducted at a temperature of ice cooling to approximately the boiling point of the solvent, preferably room temperature to about 10° C., taking a period of time ranging from about 5 minutes to about 30 hours, preferably about 30 minutes to about 15 hours.

The hydrolysis under basic conditions can be effected in an alkaline solution at a temperature of ice cooling to approximately the boiling point of the solvent, preferably room temperature to about 100° C., taking a time period of about 5 minutes to about 30 hours, preferably about 1 to about 15 hours. Examples of useful alkaline solutions are solutions of hydroxide or carbonate or like salt of alkali metal such as lithium, sodium, potassium, etc. or hydroxide or carbonate or like salt of alkaline earth metal such as magnesium, calcium, etc. dissolved in water and/or an organic solvent. The alkaline substance can be used in an amount of at least equimolecular with the compound (13). Examples of useful organic solvents are acetone, acetonitrile, ethyl acetate, ethers such as diethyl ether, dioxane, tetrahydrofuran and the like, halogenated hydrocarbons such as methylene chloride, chloroform and the like, aromatic hydrocarbons such as benzene, toluene and the like, etc.

Reaction scheme-e

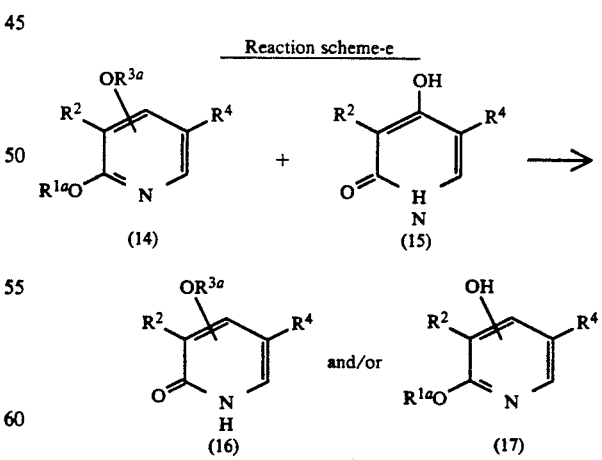

wherein $R^{1a}$, $R^2$, $R^{3a}$ and $R^4$ are as defined above.

In this process, a pyridone derivative (15) is reacted with a compound (14), i.e. diacyloxy compound in a suitable solvent to give a compound (16) and/or compound (17), i.e. monoacyloxy product. Solvents useful in this reaction can be any of those which do not adversely affect the reaction and which include, for example, acetone, acetonitrile, ethyl acetate, dioxane, tetrahydrofuran, N,N-dimethylformamide, etc. The amount of the pyridone derivative (15) to be used is at least about 0.5 mole, preferably about 1 mole, per mole of the compound (14). The reaction is carried out at room temperature to the boiling point of the solvent, taking a time period of about 10 minutes to about 50 hours, preferably about 5 to about 20 hours. Trimethylamine, triethylamine or like amine can be added to the reaction system in an amount of about 0.1 to about 10 moles per mole of the compound (14).

The pyridine compounds having the formula (1) in which the nitrogen atom at 1-position of the pyridine ring has as a substituent a group $R^7$, which is as defined below, can be prepared by silylating the corresponding compounds in which at least one of $R^1$, $R^2$ and $R^3$ is hydroxy and the nitrogen atom at 1-position has no substituent and then alkylating the silylated compound. Further, the desired compounds can also be prepared by acylation of the hydroxy group of the alkylated compounds. Preferred examples thereof are shown in reaction schemes f to h below.

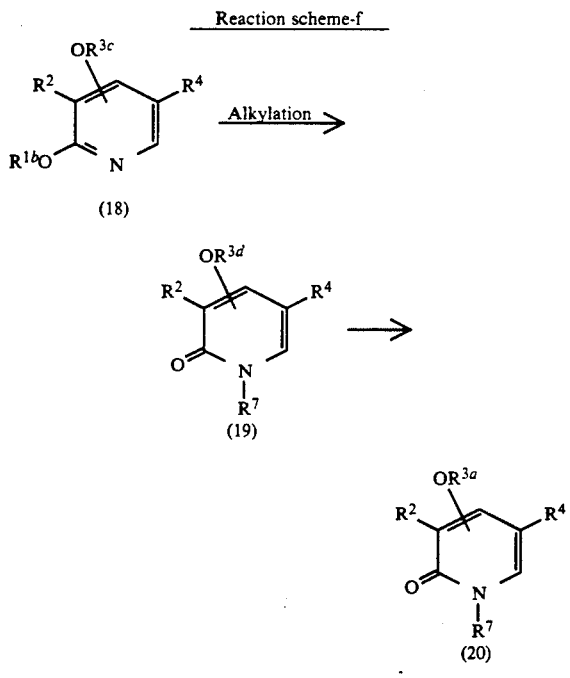

wherein $R^{1b}$, $R^2$, $R^{3d}$, $R^{3a}$ and $R^4$ are as defined above, $R^{3c}$ is trialkylsilyl or acyl, and $R^7$ is lower alkyl, tetrahydrofuranyl, tetrahydropyranyl, lower alkoxy-lower alkyl, phthalidyl, or phenyl-lower alkoxy-lower alkyl.

In the first stage of the process, an alkylating agent is reacted with a compound (18) in a suitable solvent to alkylate the compound at the N-position of the pyridine ring. Examples of solvents useful in the reaction are ethers such as diethyl ether, tetrahydrofuran and dioxane; halogenated hydrocarbons such as methylene chloride and chloroform; armatic hydrocarbons such as benzene and toluene; and other solvents such as acetonitrile, acetone, ethyl acetate; etc. Exemplary of useful alkylating agents are methyl chloride, ethyl bromide and like halogenated lower alkyl and groups $R^8$—CO—O—$R^{7a}$ wherein $R^8$ is lower alkyl, and $R^{7a}$ is tetrahydrofuranyl, lower alkoxy-lower alkyl, phthalidyl or phenyl-lower alkoxy-lower alkyl. The amount of the alkylating agent to be used is about 0.5 to about 5 moles, preferably about 1 to about 2 moles, per mole of the compound (18). The reaction is carried out at a temperature of ice cooling to approximately the boiling point of the solvent, preferably room temperature to about 60° C., taking a time period of about 10 minutes to 30 hours, preferably about 1 to about 4 hours. It is preferred to add a catalytic amount of Lewis acids to the reaction system.

In the latter stage of the process, the free hydroxyl group of a compound (19) wherein $R^3$ is hydrogen atom is acylated and the acylation is performed in the same manner as that in Reaction scheme-a.

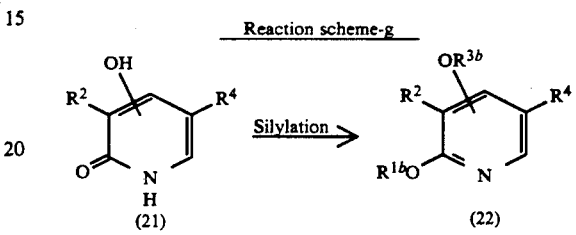

wherein $R^{1b}$, $R^2$, $R^{3b}$ and $R^4$ are as defined above.

In this process, a silylating agent is reacted with a compound (21) in a suitable solvent to silylate the compound at the 2- and 4-positions or 2- and 6-positions of the pyridine ring at the same time. Examples of silylating agents useful in the silylation are 1,1,1,3,3,3,-hexamethyldisilazane and the like bis(trialkylsilyl)amines, trimethylchlorosilane, dimethyl-t-butyl chlorosilane and like halogenated trialkylsilanes, N,O-bistrimethyl acetamide and like silylated acetamides, etc. The amount of the silylating agent to be used is at least about 2 moles per mole of the compound (21). When using the halogenated trialkylsilane as the silylating agent, it is preferred to use at least 2 moles of triethylamine, trimethylamine or like amine or pyridine per mole of the silylating agent. Solvents useful in the reaction can be any of those which do not adversely affect the reaction. When using, for example, the halogenated trialkylsilanes, silylated acetamides or like silylating agent, diethyl ether, dioxane, tetrahydrofuran or like ethers, methylene chloride, chloroform or like halogenated hydrocarbons, acetonitrile, etc. can be used as the solvent. When using bis(trialkylsilyl)amines as the silylating agent, the silylating agent per se is usable as the solvent, although the above organic solvents can also be used. The reaction is carried out at room temperature to approximately the boiling point of the solvent, preferably more or less the boiling point of the solvent, taking a time period of about 10 minutes to about 24 hours, preferably about 1 to about 15 hours.

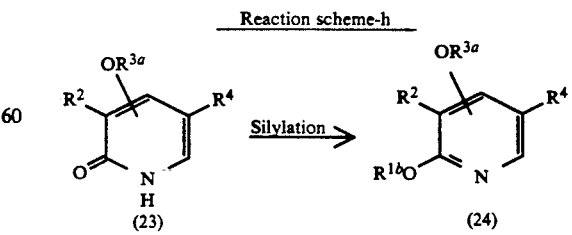

wherein $R^{1b}$, $R^2$, $R^{3a}$ and $R^4$ are as defined above.

In this process, a compound (23) is silylated. The silylation is conducted under the same conditions as in Reaction scheme-g except that the silylating agent is used in an amount at least equimolecular with the compound (23).

There will be described below in detail the process for preparing a novel active ingredient (i.e. the compound (3)) for an anti-cancer agent, the active ingredient having an antitumor activity which can be increased by the pyridine derivative of this invention.

The compound (3) can be prepared, for example, by the processes shown below in Reaction schemes-i to -m.

Reaction scheme-i

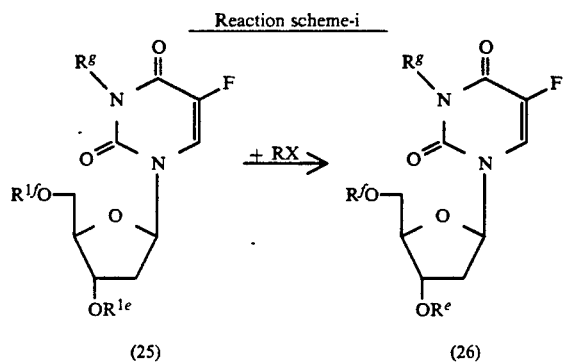

(25)            (26)

wherein $R^g$ is as defined above, at least one of $R^{1e}$ and $R^{1f}$ is hydrogen atom and the other is acyl or protective group, R is phenyl-lower alkyl which may have a substituent selected from the group consisting of lower alkyl, lower alkoxy, halogen atom and carboxyl, lower alkoxycarbonyl, di(lower alkyl)amino, phenyl-lower alkyl having lower alkylenedioxy or phenyl as a substituent, phenyl-lower alkenyl or naphthyl-lower alkyl, $R^e$ and $R^f$ are as defined above and X is halogen atom.

The protective groups represented by $R^{1e}$ or $R^{1f}$ include the following groups.

(a) Triaryl-substituted methyl groups represented by the formula

(A)

wherein Ar is aryl. Exemplary of such a group is a methyl group substituted with three aryl groups such as phenyls which may have halogen atom, nitro, lower alkyl or lower alkoxyl as the substituent.

(b) Cyclic ether residue groups represented by the formula

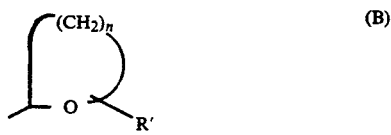

(B)

wherein R' is lower alkyl, and n is 2 or 3. Examples of such groups are 2-tetrahydrofuranyl and 2-tetrahydropyranyl.

(c) Lower alkoxymethyl groups such as methoxymethyl, ethoxymethyl and hexyloxymethyl.

(d) Tri(lower alkyl)silyl groups such as trimethylsilyl and t-butyldimethylsilyl.

The reaction is conducted by reacting a compound (25) with a phenyl-lower alkyl halide (RX) to substitute the desired group R for the hydrogen atom at the 3'- or 5'-position of the compound (25), followed by a reaction for removing the acyl group when required, to obtain a compound (26).

The reaction for introducing the group R is conducted under the usual dehydrohalogenation conditions. The hydrogen halide removing agent to be used can be any of various basic compounds which are generally used for such reactions. Examples of useful compounds are sodium hydroxide, potassium hydroxide, sodium carbonate, potassium carbonate, sodium hydrogencarbonate, potassium hydrogencarbonate, alkali metals such as sodium and potassium, alkali metal hydrides such as sodium hydride and potassium hydride, etc.

The reaction can be conducted in the presence of a solvent or in the absence thereof. Examples of useful solvents are usual inert solvents such as water, ethers such as tetrahydrofuran (THF) and dioxane, aromatic hydrocarbons such as benzene, toluene, xylene and chlorobenzene, ketones such as acetone and methyl ethyl ketone, nitriles such as acetonitrile and propionitrile, etc.

While the ratio of the phenyl-lower alkyl halide (RX) to the compound (25) is not limited specifically but is widely variable, usually at least about 1 mole, preferably about 1 to about 5 moles, of the latter is used per mole of the former. The reaction temperature is not limited specifically either but is widely variable. It is, however, usually 0° to 100° C., preferably room temperature to 80° C. The reaction is carried out usually for about 30 minutes to about 64 hours, preferably about 1 to about 5 hours.

When the compound obtained by the above reaction has a protective group at the 3'- or 5'-position, the desired compound (26) can be obtained by subsequently subjecting the product to a reaction for removing the protective group. This reaction is carried out usually in a solvent, using a suitable amount of a catalyst which is commonly used for acid hydrolysis reactions. Examples of suitable catalysts are inorganic acids such as hydrochloric acid, sulfuric acid and perchloric acid, and organic acids including lower alkanoic acids such as formic acid, acetic acid and propionic acid, benzoic acid, organosulfonic acids such as methanesulfonic acid, ethanesulfonic acid, benzenesulfonic acid and 4-methylbenzenesulfonic acid. Examples of useful solvents are usual inert solvents including water, lower alcohols such as methanol, ethanol and isopropanol, ketones such as acetone and methyl ethyl ketone, ethers such as diethyl ether, THF and dioxane, aromatic hydrocarbons such as benzene, toluene, xylene and chlorobenzene, lower alkanoic acids such as acetic acid and propionic acid, and mixtures of such solvents. The reaction temperature is not limited specifically but is suitably determined from a wide range. Usually it is 0° to 100° C., preferably room temperature to about 80° C. The reaction takes about 3 minutes to about 20 hours. The acid is usually used in a catalytic amount to an excessive amount, preferably in an excessive amount.

When the compound (26) prepared by the process of the scheme-i has acyl at least at one of the 3-, 3'- and 5'-positions, the compound is subjected to a hydrolysis reaction, whereby one or all of the acyl groups can be converted to hydrogen. The hydrolysis reaction is carried out under the usual conditions for acid or alkali hydrolysis. The catalyst to be used for this reaction can be any one of those which are commonly used for acid or alkali hydrolysis. Typical of these catalysts are basic compounds such as sodium hydroxide, potassium hydroxide and barium hydroxide, and inorganic acids such as hydrochloric acid, sulfuric acid and nitric acid. The amount of catalyst to be used is not limited specifically but is suitably variable over a wide range. Generally, the reaction proceeds advantageously in a solvent. A wide variety of usual inert solvents are usable for this purpose. Examples of useful solvents are water, lower alcohols such as methanol, ethanol and propanol, ketones such as acetone and methyl ethyl ketone, and mixtures of such solvents. The reaction temperature is not limited specifically but is suitably determined from a wide range. It is usually 0° to 100° C., preferably room temperature to about 80° C. The reaction takes about 30 minutes to about 10 hours.

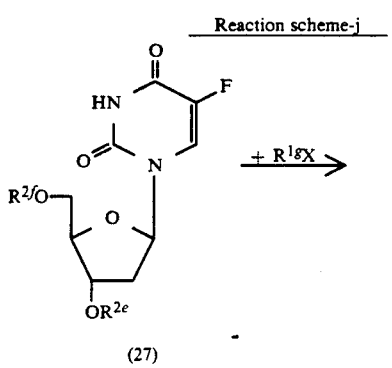

place also at such position simultaneously with acylation at the 3-position. Accordingly, it is desirable to protect the hydroxyl group at the 3'- or 5'-position before acylation and to remove the protective group after the acylation. The reaction for introducing the protective group will be described later. The reaction to remove the protective group can be carried out by the same method as already described for the reaction scheme-i.

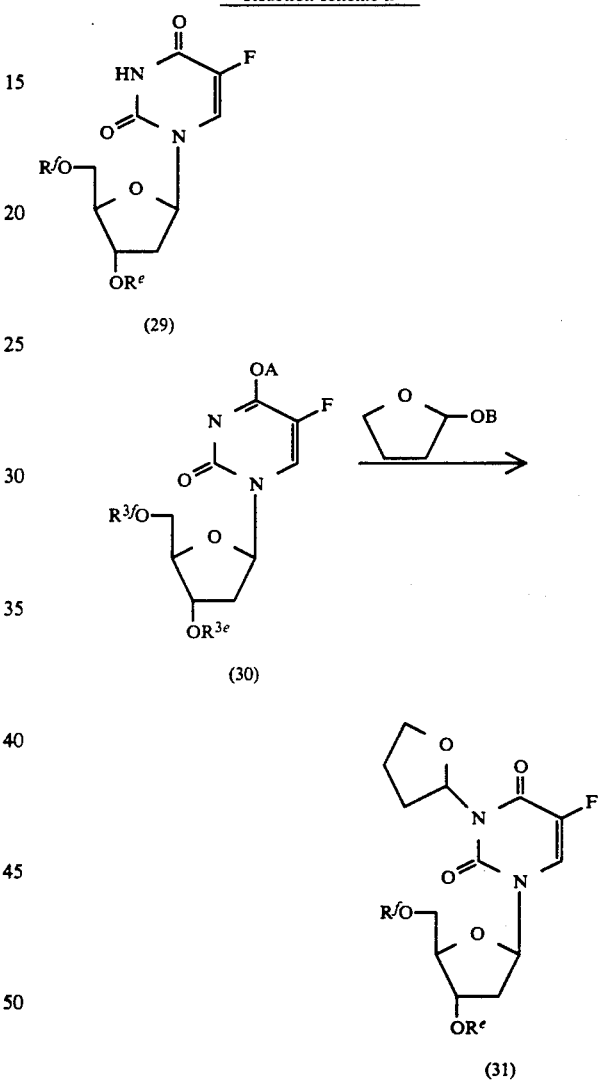

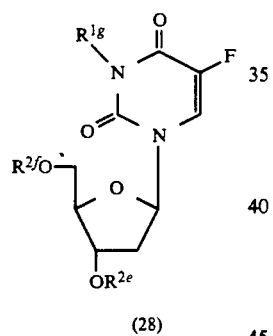

wherein one of $R^{2e}$ and $R^{2f}$ is the same as the group R defined above, the other is hydrogen atom, acyl or a protective group, $R^{1g}$ is acyl, and $R^1$ and $R^2$ are as defined above.

The acylation reaction, wherein acyl is introduced into the 3-position of the pyrimidine skeleton, can be conducted by a usual process, e.g., the acid chloride process. With the acid chloride process, an acyl halide ($R^{1g}X$) is caused to act on the compound (27) in a suitable solvent in the presence of an acid scavenger to give the desired compound (28). Examples of useful acid scavengers are sodium hydrogencarbonate, sodium carbonate, potassium carbonate, pyridine, triethylamine, etc. Examples of useful solvents are benzene, chloroform, methylene chloride, carbon tetrachloride, dioxane, tetrahydrofuran, etc. The acyl halide is used in an amount of at least about one mole, preferably about 1 to about 3 moles, per mole of the compound (27). The reaction temperature is usually −30° to 100° C., preferably room temperature to about 80° C. The reaction takes about 20 minutes to about 20 hours.

When the compound (27) to be reacted has a free hydroxyl group at its 3'- or 5'-position, acylation takes wherein $R^e$ and $R^f$ are as defined above, A is tri(lower alkyl)silyl, B is lower alkanoyl, one of $R^{3e}$ and $R^{3f}$ is the same as the group R defined above and the other is the same as the group A or acyl.

According to the above trialkylsilylation reaction, bis-N,O-tri(lower alkyl)silylacetamide is reacted with a compound (29) to obtain a compound (30), which is then reacted with 2-lower alkanoyloxytetrahydrofuran to give a compound (31) (tetrahydrofuranylation).

The trialkylsilylation reaction is conducted in a suitable inert solvent at about 0° to about 100° C., preferably at room temperature to about 50° C. for 30 minutes to 6 hours. Examples of suitable solvents are ethers such as dioxane, tetrahydrofuran, etc., aromatic hydrocarbons such as benzene, toluene etc., dimethylformamide, dimethylsulfoxide, acetonitrile, etc. The bis-N,O-tri(-lower alkyl)silylacetamide may be used in an amount of at least one equivalent, preferably 1 to 2 equivalents, per functional group to be reacted therewith.

The subsuquent tetrahydrofuranylation reaction is carried out in a solvent as exemplified above at about 0° to about 100° C., preferably at room temperature to about 50° C. for 30 minutes to 6 hours. 2-Lower alkanoyloxytetrahydrofuran is used in an amount of at least one mole, preferably 1 to 2 moles, per mole of the compound (30). This reaction proceeds advantageously when the reaction system contains a Lewis acid, such as stannic chloride (SnCl$_4$), aluminum chloride or zinc chloride, usually in an amount of at least 0.1 mole based on the compound (30). When the compound (30) used for the tetrahydrofuranylation reaction contains tri(-lower alkyl)silyl as R$^{3e}$ or R$^{3f}$, the product is subsequently subjected to a reaction to remove this group, whereby the desired compound (31) is obtained. This reaction is carried out in the same manner as the reaction already stated for the reaction scheme-i for the removal of the protective group.

The compound having the protective group in Reaction scheme-i can be prepared, for example, by the processes as shown below in Reaction schemes-l and -m.

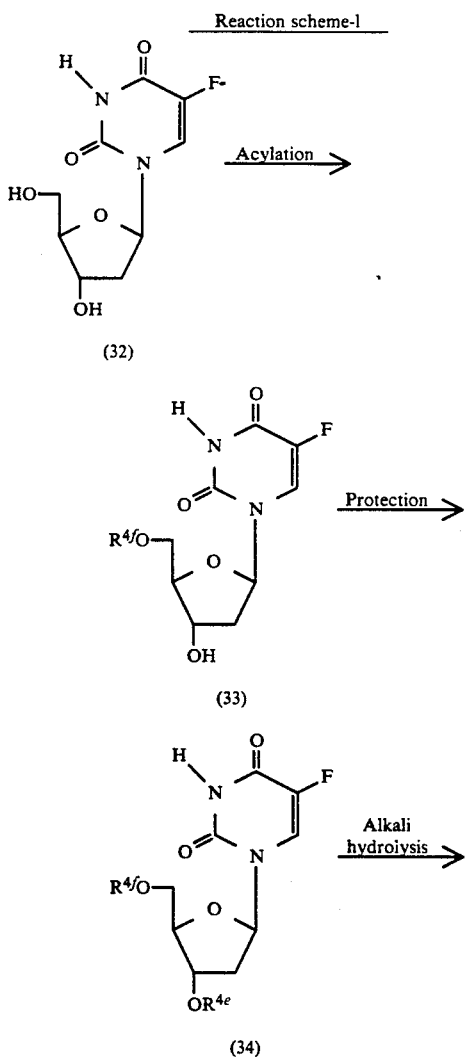

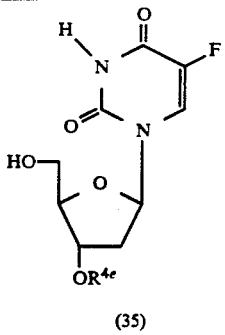

wherein R$^{4f}$ is acyl and R$^{4e}$ is a protective group.

For the acylation of a compound (32), any of usual acylation processes are usable, such as the acid halide process, acid anhydride process, mixed acid anhydride process, N,N-dicyclohexylcarbodiimide process (DCC process), etc., among which the acid anhydride process is advantageous.

The acid anhydride process is conducted by heating the compound (32) with an acid anhydride in a suitable solvent. The acid anhydride to be used is the anhydride of an acid corresponding to the acyl group to be introduced into the 5'-position of the compound (32). Examples of such anhydrides are acetic anhydride, propionic anhydride, butyric anhydride, benzoic anhydride, etc. These acid anhydrides are preferably used in an amount of about 1 to about 1.5 moles, per mole of the compound (32). Examples of useful solvents are various inert solvents including pyridine, halogenated hydrocarbons such as chloroform and dichloromethane, ethers such as dioxane and THF, aromatic hydrocarbons such as benzene and toluene, dimethylformamide (DMF), dimethyl sulfoxide (DMSO), acetonitrile, etc. The reaction temperature is usually about −30° C. to about 80° C. The reaction takes about 1 to about 6 hours. The reaction can be carried out advantageously in the presence of a basic compound. Examples of useful basic compounds are organic bases such as pyridine, triethylamine, N,N-dimethylaniline and like tertiary amines, sodium acetate, etc. and inorganic basic compounds such as sodium hydrogencarbonate, potassium carbonate, sodium acetate, etc.

The above reaction gives as the main product a compound (33) wherein the 5'-position is acylated and also as a minor product a compound wherein the 3'- position is acylated.

The compound (33) resulting from the reaction is then subjected to a reaction to protect the hydroxyl group at the 3'-position. By this reaction, the protective group mentioned with respect to Reaction scheme-i is introduced into the 3'- position of the compound (33). Useful reagents for introducing the protective group are triaryl-substituted methyl halides for giving a protective group represented by the formula (A), unsaturated cyclic ethers for giving a protective group in the formula (B), which are represented by the formula

wherein R' and n are the same as those in the formula (B), lower alkoxymethyl halides and tri(lower alkyl)silyl halides.

The protective group-introducing reaction wherein such a halide is used is conducted in the same manner as the hydrogen halide removing reaction shown in Reaction scheme-i. However, it is desirable that the reagent is used in an amount of 1 to 2 moles, preferably 1 to 1.5 moles, per mole of the compound (33), and that the reaction temperature is −30° C. to 80° C.

The protective group-introducing reaction wherein as unsaturated cyclic ether of the formula (B') is used is conducted in the presence of an acid catalyst in an aprotic inert solvent such as THF, dioxane or acetonitrile. Examples of useful acid catalysts are hydrohalogenic acids such as hydrogen bromide and hydrogen chloride, and Lewis acids such as aluminum chloride, boron fluoride and zinc chloride. The reaction can be preferably conducted using 1 to 1.5 moles of the reagent per mole of the compound (33) at −30° C. to 60° C. for about 2 to about 5 hours.

The reaction to remove the acyl group from the 5'-position of the resulting product (34) is conducted under the conditions of alkali hydrolysis, i.e. under the same conditions as the hydrolysis reaction for Reaction scheme-i wherein a basic compound is used as a catalyst.

Reaction scheme-m

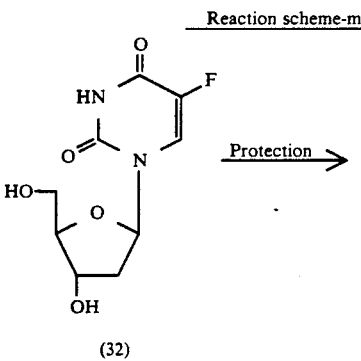

(32)

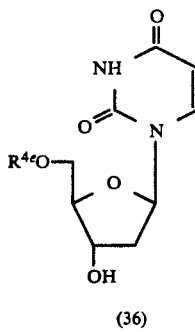

(36)

wherein $R^{4e}$ is as defined above.

This reaction introduces a protective group directly into the compound (32), giving a compound (36) having the protective group at the 5'-position. The reaction is conducted under the same conditions as in Reaction scheme-1.

The processes of the schemes-1 and -m afford starting compounds having an acyl group or protective group at the 3'- or 5'-position.

For use in increasing the anti-cancer activity of an anti-cancer compound, the pyridine derivative having the formula (1) to be used in this invention may be formulated into a preparation which is administered to cancer patients with an anti-cancer compound.

The composition of this invention for increasing the anti-cancer activity of an anti-cancer compound may comprise an effective amount of the pyridine derivative of the formula (1) and a pharmaceutically effective amount of the anti-cancer compound. In this case, the composition is formulated so that the pyridine derivative and the anti-cancer compound are administered in the form of a single preparation comprising the pyridine derivative and the anti-cancer compound, or in the form of two preparations for separate doses, namely one comprising the pyridine derivative and the other comprising the anti-cancer compound. In either case, the derivative of this invention is used in an amount of about 0.1 to about 10 moles, preferably about 0.5 to about 1.5 moles, per mole of the anticancer compound.

Pharmaceutical preparations for increasing anti-cancer activity of an anti-cancer compound according to this invention can be formulated into a usual form by using diluents and excipients commonly used, such as fillers, extenders, binders, wetting agents, disintegrating agents, surfactants, lubricants and the like. Administration unit forms of the pharmaceutical compositions of the present invention can be varied and selected so as to meet various therapeutical purposes. Typical forms of the pharmaceutical compositions can be exemplified such as tablets, pills, powders, liquids, suspensions, emulsions, granules, capsules, suppositories, injections (liquids, suspensions and others), ointments and the like. In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, a glucose solution, starch solution, gelatin solution, carboxymethyl cellulose, shellac, methyl cellulose, potassium phaphate, polyvinylpyrrolidone and others; disintegrating agents such as dried starch, sodium alginate, agar-agar powder, laminaran powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearing cacao butter, hydrogenated oils and others; absorption accelerators such as quaternary ammonium base, sodium laurylsulfate and others; wetting agents such as glycerin, starch and others; adsorption accelerators such as starch, lactose, kaolin, bentonite, colloidal silicic acid and others; and lubricants such as purified talc powder, stearic acid salts, boric acid powder, polyethylene glycol and others can be exemplified. If necessary, the tablets can further be coated with usual coating film to make them into coated tablets, for example sugar-coated tablets, gelatin film-coated tablets, enteric film-coated tablets, film-coated tablets, or double-layered tablets, multiple-layered tablets and others. In shaping into the form of pills, those known as the carriers in this field can widely be applied for example, excipients such as glucose, lactose, starch, cacao butter, hydrogenated vegetable oils, kaolin, talc and others; binders such as powdered gum arabic, powdered tragacanth gum, gelatin, ethanol and others; disintegrating agent such as laminaran, agar-agar powder and others. In shaping into the form of suppositories, those known in this field can widely be applied for example, polyethylene glycol, cacao butter, a higher alcohol, an ester of a higher alcohol, gelatin, semi-synthesized glyceride and others. Capsules are prepared in a conventional manner by admixing the compound of the invention with the foregoing various carrier and encapsulating the mixture into hard-gelatin capsules, soft-gelatin capsules, etc. In case of preparing injections, solutions, emulsions and suspensions being prepared are sterilized, and they are preferably isotonic to the blood. In preparing into the form of solutions, emulsions and suspensions, those known as the diluents in this field can widely be applied, for example water, ethyl alcohol, macrogol, propylene glycol, ethoxylated isostearyl alcohol, polyoxylated isostearyl alcohol, a polyoxyethylene sorbitan fatty acid ester and others. In case of preparing isotonic solutions, sufficient amount of sodium chloride, glucose or glycerin may be added to make the solution to be isotonic to the blood. The pharmaceutical compositions for injection preparation may further contain usual dissolving agents, buffer solutions, analgesic agents or the like if necessary. The pharmaceutical composition of the present invention may also contain coloring agents, preservatives, perfumes, seasoning agents, sweetening agents and others, as well as contain other medicines, if necessary. In shaping into the form of pastes, creams and gels, diluents such as white vaseline, paraffins, glycerine, cellulose derivatives, polyethylene glycols, silicones, bentonite and the like can be used.

The amount of the desired product according to the present invention to be contained as the active ingredient in the pharmaceutical composition is not specifically restricted and can be selected from a wide range, generally 1 to 70% by weight, may be used.

Administration method of the above-mentioned pharmaceutical composition is not specifically restricted and the composition can be administered through a suitable method for the respective types of administration forms, depending upon age of the patient, distinction of the sex and other conditions, conditions of the patient and others. For example, tablets, pills, liquids, suspensions, emulsions, granules and capsules are administered orally; injections are administered intraveneously singly or as a mixture with usual injectable transfusions such as a glucose solution, an amino acids solutions, and others; and if necessary the injections are administered singly intramuscularly, intracutaneously, subcutaneously or intraperitoneally; and the suppositories are administered into rectum.

The dosage of the desired preparations of the present invention may suitably be selected depending upon the method for administration, age of the patient, distinction of sex and other conditions, and patient's conditions or symptoms, and generally the pharmaceutical compositions of the invention can be administered in an amount of about 0.5 to about 20 mg/kg of the body weight/day, calculated as the antitumor compound (active ingredient), in 1 to 4 divided doses.

The present invention will be described in greater detail with reference to the following reference examples, examples, pharmaceutic tests and preparation examples.

In connection with the NMR data in the reference examples and examples, the numerals used as a subscript at the right of the symbol "C", "H" or "N" are used to refer to the position in the compound. Thus the term "$C_6$-H", for example, refers to the hydrogen bonded to the carbon atom at the 6-position. Similarly the term "$C_{3',4',5'}$-H", for example, denotes the hydrogens bonded to the carbon atoms at the 3'-, 4'- and 5'-positions. Also the term "$H_1$", for example, refers to the hydrogen bonded to the carbon atom at the 1-position. The term "$N_3$-H", for example, refers to the hydrogen bonded to the nitrogen atom at the 3-position.

Reference Example 1

Preparation of 5'-O-benzyl-2'-deoxy-5-fluorouridine

To a solution of 1.00 g of 5'-O-acetyl-2'-deoxy-5-fluoro-3'-O-trityluridine in 30 ml of methanol was added a 1 N aqueous solution of sodium hydroxide, and the mixture was stirred at room temperature for 4 hours. The reaction mixture was neutralized with acetic acid and concentrated. The concentrate was washed with petroleum ether, dried, and dissolved in a mixture of 20 ml of benzene and 20 ml of dioxane. To the solution were added 0.27 ml of benzyl bromide and 0.15 g of potassium hydroxide powder, and the mixture was refluxed overnight. The solvent was distilled off and the residue was dissolved in 50 ml of 80% acetic acid, and the solution was left to stand at 80° C. for 4 hours. The solvent was distilled off, and the residue was placed on a silica gel column to conduct a gradient elution using chloroform and mixtures of methanol (up to 2%) and chloroform. The fractions corresponding to 5'-O-benzyl-2'-deoxy-5-fluorouridine were collected and concentrated. The concentrate was recrystallized from ethanol, giving 0.33 g of the title compound in a yield of 52%.

M.p. 129°–130° C.

Elementary Analysis: for $C_{16}H_{17}FN_2O_5$ Calcd. (%): C 57.14; H 5.09; N 8.33 Found (%): C 57.14; H 5.35; N 8.34

NMR(DMSO-$d_6$)δ: 11.76 (1H, bs, —NH—, disappeared by addition of $D_2O$) 7 95 (1H, d, J=7 Hz, $C_6$—H) 7.34 (5H, s, phenyl-H) 6.15 (1H, t, J=7 Hz, $C_1'$—H) 5.33 (1H, bs, 3'—OH, disappeared by addition of $D_2O$)

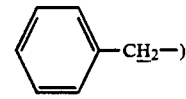

4.34–4.16 (1H, m, $C_{3'}$—H) 4.00–3.89 (1H, m, $C_{4'}$—H) 3.69–3.63 (2H, m, $C_{5'}$—H) 2.14 (2H, t, J=6 Hz, $C_{2'}$—H).

Reference Example 2

Preparation of 3'-O-benzyl-2'-deoxy-5-fluorouridine

To a mixture of 50 ml of benzene and 50 ml of dioxane were added 1.00 g of 2'-deoxy-5-fluoro-5'-O-trityluridine, 0.30 ml of benzyl bromide and 0.23 g of potassium hydroxide powder, and the mixture was refluxed for 25 hours. The insolubles were removed by filtration and the filtrate was concentrated and the concentrate was dissolved in 5 ml of 80% acetic acid. The solution was left to stand at 80° C. for 2 hours. The solvent was distilled off and the residue was placed on a silica gel column to conduct a gradient elution using chloroform and mixtures of methanol (up to 2%) and chloroform. The fractions corresponding to 3'-O-benzyl-2'-deoxy-5-fluorouridine were collected and concentrated. The concentrate was recrystallized from ethanol, giving 0.14 g of the title compound in a yield of 20%.

M.p. 138°–139° C.

Elementary Analysis: for $C_{16}H_{17}FN_2O_5$ Calcd. (%): C 57.14; H 5.09; N 8.33 Found (%): C 57.16; H 5.30; N 8.13

NMR(DMSO-$d_6$)δ: 11.82 (1H, bs, —NH—, disappeared by addition of $D_2O$) 8.21 (1H, d, J=7 Hz, $C_6$—H) 7.35 (5H, s, phenyl-H) 6.16 (1H, t, J=6 Hz, $C_{1'}$—H) 5.22 (1H, bs, 5'—OH, disappeared by addition of $D_2O$)

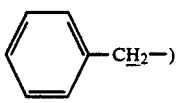

4.24–4.19 (1H, m, $C_{3'}$—H) 4.09–4.06 (1H, m, $C_{4'}$—H) 3.65—3.53 (2H, m, $C_{5'}$—H) 2.51–2.16 (2H, m, $C_{2'}$—H)

Reference Example 3

Preparation of 2'-deoxy-5-fluoro-3'-O-(3,4-methylenedioxybenzyl)uridine

The title compound was prepared in a yield of 23% in the same manner as in Reference Example 2 except that acetonitrile was used as the reaction solvent in place of the dioxane.

M.p. 186°–188° C.

Elementary Analysis: for $C_{17}H_{17}FN_2O_7 \cdot 0.5\ H_2O$ Calcd. (%): C 52.44; H 4.66; N 7.19 Found (%): C 52.60; H 4.62; N 7.03

NMR(CDCl$_3$)δ: 11.80 (1H, d, J=5 Hz, —NH—, disappeared by addition of $D_2O$) 8.18 (1H, d, J=7 Hz, $C_6$—H) 6.90–6.85 (3H, m, phenyl-H) 6.11 (1H, t, J=6 Hz, $C_{1'}$—H) 5.99 (2H, s, —O—CH$_2$—O—) 5.17 (1H, t, J=5 Hz, 5'—OH, disappeared by addition of $D_2O$) 4.42 (2H, s,

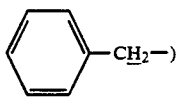

4.18–4.00 (2H, m, $C_{3'} \cdot C_{4'}$—H) 3.64–3.61 (2H, m, $C_{5'}$—H) 2.30–2.20 (2H, m, $C_{2'}$—H)

Reference Examples 4 and 5

Preparation of 3'-O-benzyl-2'-deoxy-5-fluorouridine (Reference Example 4) and 5'-O-benzyl-2'-deoxy-5-fluorouridine (Reference Example 5)

A 11.4 g quantity of potassium hydroxide was dissolved in a mixture of 350 ml of water and 100 ml of dioxane. To the mixture were added 10.0 g of 2'-deoxy-5-fluorouridine and 3.0 ml of benzyl bromide at room temperature with stirring. Then, every 24 hours, 100 ml of 5% aqueous solution of potassium hydroxide and 3.0 ml of benzyl bromide were added three times to the mixture. Then, the resulting mixture was stirred overnight. The reaction mixture was washed twice with 200 ml of ether, and the aqueous layer was neutralized with 6N-HCl and concentrated to about 200 ml. The concentrate was adjusted to a pH of about 3 to 4 with 6N-HCl and extracted twice with 100 ml of ethyl acetate. The ethyl acetate layer was separated, dried over anhydrous sodium sulfate and concentrated. The oily residue was placed on a silica gel column to conduct a gradient elution using chloroform and mixtures of methanol (up to 2%) and chloroform. The fractions corresponding to 3'-O-benzyl-2'-deoxy-5-fluorouridine were collected and concentrated. The concentrate was recrystallized from ethanol, giving 3.57 g of the desired compound in a yield of 26.1%.

M.p. 138°–139° C.

Elementary Analysis: for $C_{16}H_{17}FN_2O_5$ Calcd. (%): C 57.14; H 5.09; N 8.33 Found (%): C 57.12; H 5.28; N 8.24

Then the fractions corresponding to 5'-O-benzyl-2'-deoxy-5-fluorouridine were collected and concentrated. The concentrate was recrystallized from ethanol, giving 0.40 g of the desired compound in a yield of 2.9%.

M.p. 129°–130° C.

Elementary Analysis: for $C_{16}H_{17}FN_2O_5$ Calcd. (%): C 57.14; H 5.09; N 8.33 Found (%): C 57.29; H 5.30; N 8.26

Reference Examples 6–17

The general procedures of Reference Examples 4 and 5 were followed, thereby giving the following compounds.

Reference Example 6

3'-O-(2-fluorobenzyl)-2'-deoxy-5-fluoro uridine

Yield 34%

M.p. 121°–123° C.

NMR(DMSO-$d_6$)δ: 11.82 (1H, bs, —NH—, disappeared by addition of $D_2O$) 8.21 (1H, d, J=7 Hz, $C_6$—H) 7.67–7.19 (4H, m, phenyl-H) 6.15 (1H, t, J=6 Hz, $C_{1'}$—H) 5.26 (1H, bs, 5'—OH, disappeared by addition of $D_2O$) 4.60 (2H, s

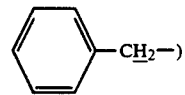

4.28–4.05 (2H, m, $C_{3'} \cdot C_{4'}$—H) 3.77–3.67 (2H, m, $C_{5'}$—H) 2.41–2.18 (2H, m, $C_{2'}$—H)

Reference Example 7

5'-O-(2-fluorobenzyl)-2'-deoxy-5-fluorouridine

Yield 5.2%

M.p.-(oily)

NMR(DMSO-$d_6$)δ: 11.7 (1H, bs, —NH—, disappeared by addition of $D_2O$) 7.92 (1H, d, J=7 Hz, $C_6$—H) 7.52–7.07 (4H, m, phenyl-H) 6.20 (1H, t, J=6 Hz, $C_{1'}$—H) 4.62 (2H, s,

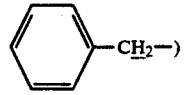

4.44–3.97 (2H, m, $C_{3'} \cdot C_{4'}$—H) 3.84–3.57 (2H, m, $C_{5'}$—H) 2.21–2.08 (2H, m, $C_{2'}$—H)

Reference Example 8

3'-O-(3-fluorobenzyl)-2'-deoxy-5-fluorouridine

Yield 27%

M.p. 113°–115° C.

NMR(DMSO-$d_6$)δ: 11.81 (1H, bs, —NH—, disappeared by addition of $D_2O$) 8.21 (1H, d, J=7 Hz, $C_6$—H) 7.46–7.01 (4H, m, phenyl-H) 6.17 (1H, t, J=6

Hz, $C_{1'}$—H) 5.22 (1H, bt, J=5 Hz, 5'—OH, disappeared by addition of $D_2O$) 4.58 (2H, s,

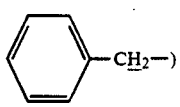

4.31–4.06 (2H, m, $C_{3'.4'}$—H) 3.74–3.59 (2H, m, $C_{5'}$—H) 2.38–2.03 (2H, m, $C_{2'}$—H)

Reference Example 9

5'-O-(3-fluorobenzyl)-2'-deoxy-5-fluorouridine

Yield 5.9%
M.p.-(oily)
NMR($CDCl_3$)δ: 10.4 (1H, bs, —NH—, disappeared by addition of $D_2O$) 7.92 (1H, d, J=7 Hz, $C_6$—H) 7.41–6.77 (4H, m, phenyl-H) 6.28 (1H, bs, $C_{1'}$—H) 4.63–3.51 (6H, m, $C_{3'.4'.5'}$—H,

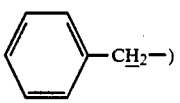

2.49–1.93 (2H, m, $C_{2'}$—H)

Reference Example 10

3'-O-(2-bromobenzyl)-2'-deoxy-5-fluorouridine

Yield 33%
M.p. 122°–124° C.
NMR(DMSO-$d_6$)δ: 11.81 (1H, bs, —NH—, disappeared by addition of $D_2O$) 8.20 (1H, d, J=7 Hz, $C_6$—H) 7.67–7.32 (4H, m, phenyl-H) 6.15 (1H, t, J=6 Hz, $C_{1'}$—H) 5.21 (1H, t, J=5 Hz, 5'—OH, disappeared by addition of $D_2O$) 4.57 (2H, s,

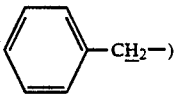

4.25–4.05 (2H, m, $C_{3'.4'}$—H) 3.70–3.52 (2H, m, $C_{5'}$—H) 2.40–1.94 (2H, m, $C_{2'}$—H)

Reference Example 11

5'-O-(2-bromobenzyl)-2'-deoxy-5-fluorouridine

Yield 5%
M.p.-(oily)
NMR(DMSO-$d_6$)δ: 11.78 (1H, bs, —NH—, disappeared by addition of $D_2O$) 7.91 (1H, d, J=7 Hz, $C_6$—H) 7.69–7.32 (4H, m, phenyl-H) 6.15 (1H, t, J=6 Hz, $C_{1'}$—H) 5.35 (1H, t, J=7 Hz, 5'—OH, disappeared by addition of $D_2O$) 4.60 (2H, s,

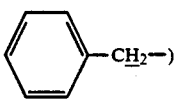

4.31–3.42 (4H, m, $C_{3'.4'.5'}$—H) 2.20–2.09 (2H, m, $C_{2'}$—H)

Reference Example 12

3'-O-(3-bromobenzyl)-2'-deoxy-5-fluorouridine

Yield 19%
M.p. 166°–168° C.
NMR(DMSO-$d_6$)δ: 11.80 (1H, bs, —NH—, disappeared by addition of $D_2O$) 8.18 (1H, d, J=7 Hz, $C_6$—H) 7.69–7.31 (4H, m, phenyl-H) 6.15 (1H, t, J=6 Hz, $C_{1'}$—H) 5.19 (1H, t, J=5 Hz, 5'—OH, disappeared by addition of $D_2O$) 4.54 (2H, s,

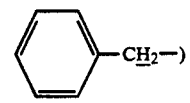

4.23–4.03 (2H, m, $C_{3'.4'}$—H) 3.71–3.57 (2H, m, $C_{5'}$—H) 2.34–2.21 (2H, m, $C_{2'}$—H)

Reference Example 13

5'-O-(3-bromobenzyl)-2'-deoxy-5-fluorouridine

Yield 3%
M.p.-(oily)
NMR(DMSO-$d_6$)δ: 11.90 (1H, bs, —NH—, disappeared by addition of $D_2O$) 8.00 (1H, d, J=7 Hz, $C_6$—H) 7.67–7.34 (4H, m, phenyl-H) 6.12 (1H, t, J=6 Hz, $C_{1'}$—H) 5.46 (1H, bs, 3'—OH, disappeared by addition of $D_2O$) 4.54 (2H, s,

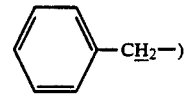

4.30–3.90 (2H, m, $C_{3'.4'}$—H) 3.74–3.68 (2H, m, $C_{5'}$—H) 2.13 (2H, t, J=6 Hz, $C_{2'}$—H)

Reference Example 14

3'-O-(4-bromobenzyl)-2'-deoxy-5-fluorouridine

Yield 12%
M.p. 214°–217° C.
NMR(DMSO-$d_6$)δ: 11.80 (1H, bs, —NH—, disappeared by addition of $D_2O$) 8.18 (1H, d, J=7 Hz, $C_6$—H) 7.55 and 7.30 (each 2H, d, J=8 Hz, phenyl-H) 6.11 (1H, t, J=6 Hz, $C_{1'}$—H) 5.19 (1H, t, J=5 Hz, 5'—OH, disappeared by addition of $D_2O$) 4.51 (2H, s,

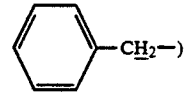

4.23–4.02 (2H, m, $C_{3'.4'}$—H) 3.73–3.60 (2H, m, $C_{5'}$—H) 2.36–2.07 (2H, m, $C_{2'}$—H)

Reference Example 15

3'-O-(4-t-butylbenzyl)-2'-deoxy-5-fluorouridine

Yield 17%
M.p.-(powder)
NMR(DMSO-$d_6$)δ: 11.80 (1H, bs, —NH—, disappeared by addition of $D_2O$) 8.18 (1H, d, J=7 Hz, $C_6$—H) 7.48 and 7.30 (each 2H, d, J=8 Hz, phenyl-H) 6.12 (1H, t, J=6 Hz, $C_{1'}$—H) 5.18 (1H, t, J=5 Hz, 5'—OH, disappeared by addition of $D_2O$) 4.48 (2H, s,

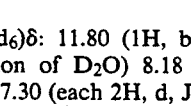

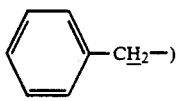

4.30–4.04 (2H, m, C$_{3'.4'}$—H) 3.76–3.60 (2H, m, C$_{5'}$—H) 2.24–2.08 (2H, m, C$_{2'}$—H) 1.27 (9H, s, CH$_3$×3)

Reference Example 16

5'-O-(4-t-butylbenzyl)-2'-deoxy-5-fluorouridine

Yield 2%

M.p.-(oily)

NMR(DMSO-d$_6$)δ: 11.80 (1H, bs, —NH—, disappeared by addition of D$_2$O) 7.94 (1H, d, J=7 Hz, C$_6$—H) 7.34 and 7.16 (each 2H, d, J=8 Hz, phenyl-H) 6.14 (1H, t, J=6 Hz, C$_{1'}$—H) 5.31 (1H, bs, 3'—OH, disappeared by addition of D$_2$O) 4 51 (2H, s,

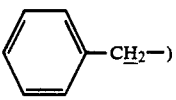

4.28–3.94 (2H, m, C$_{3'.4'}$—H) 3.74–3.64 (2H, m, C$_{5'}$—H) 2.13 (2H, t, J=6 Hz, C$_{2'}$—H) 1.27 (9H, s, CH$_3$×3)

Reference Example 17

3'-O-(4-phenylbenzyl)-2'-deoxy-5-fluorouridine

Yield 12%

M.p. 207°–209° C.

NMR (DMSO-d$_6$)δ: 11.90 (1H, bs, —NH—, disappeared by addition of D$_2$O) 8.19 (1H, d, J=7 Hz, C$_6$—H) 7.69–7.39 (9H, m, phenyl-H) 6.15 (1H, t, J=6 Hz, C$_{1'}$—H) 5.25 (1H, t, J=5 Hz, 5'—OH, disappeared by addition of D$_2$O) 4.58 (2H, s,

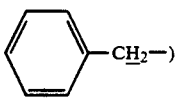

4.29–4.07 (2H, m, C$_{3'.4'}$—H) 3.83–3.63 (2H, m, C$_{5'}$—H) 2.26–2.06 (2H, m, C$_{2'}$—H)

Reference Examples 18 and 19

Preparation of 3'-O-(4-chlorobenzyl)-2'-deoxy-5-fluorouridine and 5'-O-(4-chlorobenzyl)-2'-deoxy-5-fluorouridine A 4.0 g quantity of potassium hydxoride was dissolved in a mixture of 150 ml of water and 40 ml of dioxane. To the mixture were added 2.00 g of 2'-deoxy-5-fluorouridine and 5.5 g of 4-chlorobenzyl chloride at room temperature with stirring. Two days later, the same subsequent procedure as in Examples 4 and 5 were conducted and the resulting residue was placed on a silica gel column to conduct a gradient elution using chloroform and mixtures of methanol (up to 2%) and chloroform. The fractions corresponding to 3'-O-(4-chlorobenzyl)-2'-deoxy-5-fluorouridine were collected and concentrated, giving 0.50 g of the desired compound in a yield of 17%.

M.p. 196°–198° C.

NMR(DMSO-d$_6$)δ: 11.81 (1H, bs, —NH—, disappeared by addition of D$_2$O) 8.20 (1H, d, J=7 Hz, C$_6$—H) 7.38 (4H, s, phenyl-H) 6.14 (1H, t, J=7 Hz, C$_{1'}$—H) 5.21 (1H, bt, J=5 Hz, 5'—OH, disappeared by addition of D$_2$O) 4.53 (2H, s,

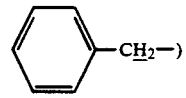

4.23–4.14 (1H, m, C$_{3'}$—H) 4.10–4.03 (1H, m, C$_{4'}$—H) 3.71–3.58 (2H, m, C$_{5'}$—H) 2.41–2.02 (2H, m, C$_{2'}$—H)

Elementary Analysis: for C$_{16}$H$_{16}$ClFN$_2$O$_5$ Calcd. (%): C 51.83; H 4.35; N 7.56 Found (%): C 51.82; H 4.60; N 7.41

Then the fractions corresponding to 5'-O-(4-chlorobenzyl)-2'-deoxy-5-fluorouridine were collected and concentrated, giving 0.12 g of the desired compound in a yield of 4.0% as a powder.

NMR(DMSO-d$_6$)δ: 11.79 (1H, bs, —NH—, disappeared by addition of D$_2$O) 7.91 (1H, d, J=7 Hz, C$_6$—H) 7.38 (4H, s, phenyl-H) 6.13 (1H, t, J=6 Hz, C$_{1'}$—H) 5.33 (1H, bs, 3'—OH, disappeared by addition of D$_2$O) 4.53 (2H, s,

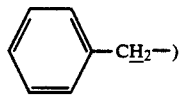

4.38–4.21 (1H, m, C$_{3'}$—H) 4.04–3.82 (1H, m, C$_{4'}$—H) 3.78–3.74 (2H, m, C$_{5'}$—H) 2.25–1.98 (2H, m, C$_{2'}$—H)

Elementary Analysis: for C$_{16}$H$_{16}$ClFN$_2$O$_5$ Calcd. (%): C 51.83; H 4.35; N 7.56 Found (%): C 51.73; H 4.80; N 7.97

Reference Examples 20–22

The general procedures of Reference Examples 18 and 19 were followed, thereby giving the following compounds.

Reference Example 20

3'-O-(2,4-dichlorobenzyl)-2'-deoxy-5-fluorouridine

Yield 14%

M.p. 88°–90° C.

NMR(DMSO-d$_6$)δ: 11.82 (1H, bs, —NH—, disappeared by addition of D$_2$O) 8.20 (1H, d, J=7 Hz, C$_6$—H) 7.60–7.37 (3H, m, phenyl-H) 6.14 (1H, t, J=6 Hz, C$_{1'}$—H) 5.21 (1H, t, J=5 Hz, 5'—OH, disappeared by addition of D$_2$O) 4.59 (2H, s,

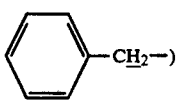

4.28–4.03 (2H, m, C$_{3'.4'}$—H) 3.69–3.60 (2H, m, C$_{5'}$—H) 2.37–2.19 (2H, m, C$_{2'}$—H)

Reference Example 21

5'-O-(2,4-dichlorobenzyl)-2'-deoxy-5-fluorouridine

Yield 3.3%

M.p. 109°–111° C.

NMR(DMSO-d$_6$)δ: 11.77 (1H, bs, —NH—, disappeared by addition of D$_2$O) 7.89 (1H, d, J=7 Hz, C$_6$—H) 7.60–7.36 (3H, m, phenyl-H) 6.14 (1H, t, J=6

Hz, $C_{1'}$—H) 5.33 (1H, bs, 3'—OH, disappeared by addition of $D_2O$) 4.61 (2H, s,

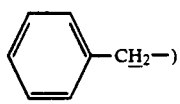

4.36–3.83 (2H, m, $C_{3'.4'}$—H) 3.74–3.60 (2H, m, $C_{5'}$—H) 2.14 (2H, t, J=6 Hz, $C_{2'}$—H)

Reference Example 22

3'-O-(4-methoxybenzyl)-2'-deoxy-5-fluorouridine

Yield 8.1%

M.p. 164°–166° C.

NMR(DMSO-$d_6$)δ: 11.81 (1H, bs, —NH—, disappeared by addition of $D_2O$) 8.19 (1H, d, J=7 Hz, $C_6$—H) 7.27 and 6.91 (each 2H, d, J=8 Hz, phenyl-H) 6.12 (1H, t, J=6 Hz, $C_{1'}$—H) 5.19 (1H, bt, J=5 Hz, 5'—OH, disappeared by addition of $D_2O$ 4.45 (2H, s

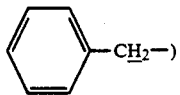

4.19–4.02 (2H, m, $C_{3'.4'}$—H) 3.70–3.50 (2H, m, $C_{5'}$—H) 2.31–2.13 (2H, m, $C_{2'}$—H)

Reference Example 23

Preparation of 2'-deoxy-5-fluoro-3'-(2-methylbenzyl) uridine

A 1.14 g quantity of potassium hydroxide was dissolved in a mixture of 33 ml of water and 16 ml of acetonitrile. To the solution were added 1.00 g of 2'-deoxy-5-fluorouridine and 1.50 g of 2-methylbenzyl bromide at room temperature with stirring. Then the same subsequent procedures as in Examples 4 and 5 were conducted, giving 0.29 g of the title compound in a yield of 20%.

M.p. 114°–116° C.

NMR(DMSO-$d_6$)δ: 11.79 (1H, bs, —NH—, disappeared by addition of $D_2O$) 8.19 (1H, d, J=7 Hz, $C_6$—H) 7.30–7.17 (4H, m, phenyl-H) 6.11 (1H, t, J=6 Hz, $C_{1'}$—H) 5.19 (1H, t, J=5 Hz, 5'—OH, disappeared by addition of $D_2O$) 4.45 (2H, s,

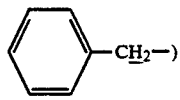

4.22–4.02 (2H, m, $C_{3'.C4'}$—H) 3.66–3.62 (2H, m, $C_{5'}$—H) 2.29–2.21 (5H, m, $C_{2'}$—H and $CH_3$)

Elementary Analysis: for $C_{17}H_{19}FN_2O_5$ Calcd. (%): C 58.28; H 5.46; N 7.99 Found (%): C 58.12; H 5.64; N 8.01

Reference Examples 24 and 25

The general procedure of Reference Example 23 Was followed, thereby giving the following compounds.

Reference Example 24

3'-O-(3-methylbenzyl)-2'-deoxy-5-fluorouridine

Yield 23%

M.p. 129°–131° C.

NMR(DMSO-$d_6$)δ: 11.80 (1H, bs, —NH—, disappeared by addition of $D_2O$) 8.19 (1H, d, J=7 Hz, $C_6$—H) 7.15 (4H, s, phenyl-H) 6.12 (1H, t, J=6 Hz, $C_{1'}$—H) 5.18 (1H, t, J=5 Hz, 5'—OH, disappeared by addition of $D_2O$) 4.49 (2H, s,

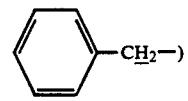

4.21–4.02 (2H, m, $C_{3'.4'}$—H) 3.66–3.61 (2H, m, $C_{5'}$—H) 2.31–2.22 (5H, m, $C_{2'}$—H and $CH_3$)

Reference Example 25

3'-O-(4-methylbenzyl)-2'-deoxy-5-fluorouridine

Yield 21%

M.p. 178°–180° C.

NMR(DMSO-$d_6$)δ: 11.81 (1H, bs, —NH—, disappeared by addition of $D_2O$) 8.18 (1H, d, J=7 Hz, $C_6$—H) 7.30–7.13 (4H, m, phenyl-H) 6.12 (1H, t, J=6 Hz, $C_{1'}$—H) 5.17 (1H, t, J=5 Hz, 5'—OH, disappeared by addition of $D_2O$)

4.20–4.01 (2H, m, $C_{3'}.C_{4'}$—H) 3.65–3.60 (2H, m, $C_{5'}$—H) 2.29–2.12 (5H, m, $C_{2'}$—H and $CH_3$)

Reference Example 26

Preparation of 3'-O-benzyl-2'-deoxy-5-fluoro-5'-O-nicotinoyluridine

A 0.21 g quantity of nicotinoyl chloride hydrochloride was added to a solution of 0.20 g of 3'-O-benzyl-2'-deoxy-5-fluorouridine in 10 ml of pyridine, and the mixture was left to stand at 80° C. for 3 hours. The solvent was distilled off and the residue was dissolved in 30 ml of ethyl acetate. The solution was washed twice with 20 ml of water. The ethyl acetate layer was dried over anhydrous sodium sulfate and concentrated. The concentrate was placed on a silica gel column and eluted with chloroform, giving 0.18 g of the title compound in a yield of 69%.

M.p. 130°–132° C.

NMR(CDCl$_3$)δ: 11.14 (1H, bs, —NH—, disappeared by addition of $D_2O$) 9.22 (1H, s,

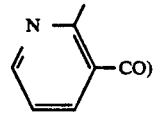

8.81 (1H, d, J=4 Hz,

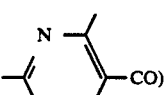

8.24 (1H, d, J=8 Hz,

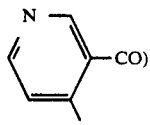

7.53–7.28 (7H, m,

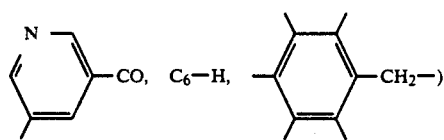

6.22 (1H, t, J=6 Hz, $C_{1'}$—H) 4.71–4.21 (6H, m,

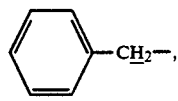

$C_{3',4',5'}$—H) 2.75–2.04 (2H, m, $C_{2'}$—H)

Elementary Analysis: for $C_{22}H_{20}FN_3O_6$ Calcd. (%): C 59.86; H 4.57; N 9.52 Found (%): C 60.01; H 4.56; N 9.58

Reference Examples 27–38

The general procedure of Reference Example 26 were followed, thereby giving the following compounds.

Reference Example 27

3'-O-benzyl-5'-O-benzoyl-2'-deoxy-5-fluorouridine

Yield 75%

M.p. 125°–127° C.

NMR(DMSO-$d_6$)δ: 11.94 (1H, bs, —NH—, disappeared by addition of $D_2O$) 8.00–7.41 (6H, m,

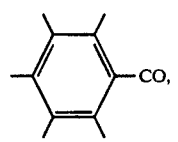

$C_6$—H) 7.33 (5H, s,

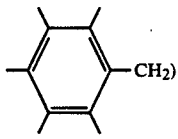

6.17 (1H, t, J=6 Hz, $C_{1'}$—H) 4.59 (6H m,

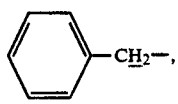

$C_{3',4',5'}$—H) 2.40–2.27 (2H, m, $C_{2'}$—H)

Reference Example 28

3'-O-benzyl-5'-O-phenoxycarbonyl-2'-deoxy-5-fluorouridine

Yield 38%

M.p.-(oily)

NMR(DMSO-$d_6$)δ: 12.00 (1H, bs, —NH—, disappeared by addition of $D_2O$) 7.95 (1H, d, J=7 Hz, $C_6$—H) 7.55–7.16 (10H, m, phenyl-H) 6.17 (1H, t, J=6 Hz, $C_{1'}$—H) 4.56–4.21 (6H, m,

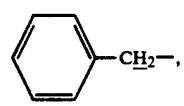

$C_{3',4',5'}$—H) 2.39–2.28 (2H, m, $C_{2'}$—H)

Reference Example 29

3'-O-benzyl-5'-O-n-hexanoyl-2'-deoxy-5-fluorouridine

Yield 51%

M.p.-(oily)

NMR(DMSO-$d_6$)δ: 11.94 (1H, bs, —NH—, disappeared by addition of $D_2O$) 7.90 (1H, d, J=7 Hz, $C_6$—H) 7.33 (5H, s, phenyl-H) 6.19 (1H, t, J=6 Hz, $C_{1'}$—H) 4.54 (2H, s,

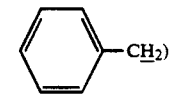

4.29–4.12 (4H, m, $C_{3',4',5'}$—H) 2.38–2.23 (4H, m, $C_{2'}$—H, —$CH_2CO$—) 1.61–1.15 (6H, m, $CH_3(CH_2)_3CH_2CO$—) 0.84 (3H, t, J=6 Hz, $CH_3CH_2$—)

Reference Example 30

3'-O-benzyl-5'-O-benzyl-carbonyl-2'-deoxy-5-fluorouridine

Yield 42%

M.p.-(oily)

NMR(CDCl$_3$)δ: 10.06 (1H, bs, —NH—, disappeared by addition of $D_2O$) 7.42–7.23 (11H, m, phenyl-H, $C_6$—H) 6.15 (1H, t, J=6 Hz, $C_{1'}$—H) 4.43 (2H, s,

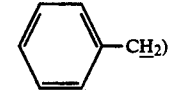

4.33–4.11 (3H, m, $C_{3',5'}$—H) 3.96–3.83 (1H, m, $C_{4'}$—H) 3.64 (2H, s,

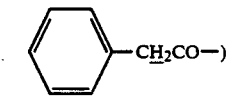

2.47–2.27, 1.65–1.49 (2H, m, $C_{2'}$—H)

Reference Example 31

3′-O-benzyl-5′-O-ethoxycarbonyl-2′-deoxy-5-fluorouridine

Yield 37%
M.p.-(oily)
NMR(CDCl$_3$)δ: 10.18 (1H, bs, —NH—, disappeared by addition of D$_2$O) 7.68 (1H, d, J=6 Hz, C$_6$—H) 7.32 (5H, s, phenyl-H) 6.31 (1H, t, J=6 Hz, C$_1'$—H) 4.40 (2H, s,

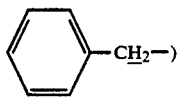

4.37–4.10 (6H, m, C$_{3',4',5'}$—H, OCH$_2$CH$_3$) 2.67–2.42, 2.23–1.92 (2H, m, C$_{2'}$—H) 1.30 (3H, t, J=7 Hz, —OCH$_2$CH$_3$)

Reference Example 32

3′-O-benzyl-5′-O-(3-methylbenzoyl)-2′-deoxy-5-fluorouridine

Yield 67%
M.p. 131°–133° C.
NMR(CDCl$_3$)δ: 9.61 (1H, bs, —NH—, disappeared by addition of D$_2$O) 7.78–7.73 (2H, m,

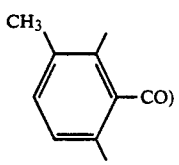

7.60 (1H, d, J=6 Hz, C$_6$—H) 7.38–7.22 (7H, m,

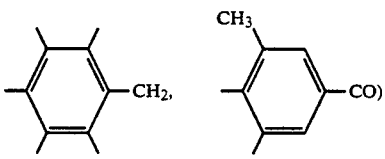

6.25 (1H, t, J=6 Hz, C$_1'$—H) 4.55–4.35 (5H, m, C$_{3',5'}$—H,

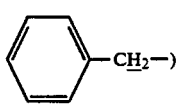

4.28–4.18 (1H, m, C$_{4'}$—H) 2.73–2.47, 2.16–1.87 (2H, m, C$_{2'}$—H) 2.38 (3H, s,

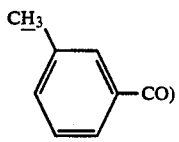

Reference Example 33

3′-O-benzyl-5′-O-(4-n-propoxybenzoyl)-2′-deoxy-5-fluorouridine

Yield 78%
M.p.-(oily)
NMR(CDCl$_3$)δ: 9.27 (1H, bs, —NH—, disappeared by addition of D$_2$O)
7.91 (2H, d, J=9 Hz, CO

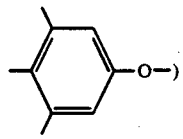

7.62 (1H, d, J=6 Hz, C$_6$—H) 7.32 (5H, s,

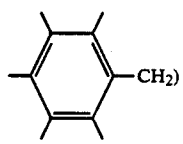

6.91 (2H, d, J=9 Hz,

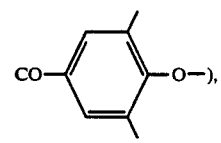

6.25 (1H, t, J=6 Hz, C$_1'$—H) 4.55–4.52 (4H, m,

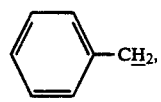

C$_{5'}$—H)
4.45–4.39 (1H, m, C$_{3'}$—H) 4.29–4.15 (1H, m, C$_{4'}$—H) 3.97 (2H, t, J=7 Hz, —CH$_2$O—) 2.74–2.52, 2.16–1.64 (4H, m, CH$_3$CH$_2$CH$_2$—O—, C$_{2'}$—H) 1.04 (3H, t, J=7 Hz, CH$_3$CH$_2$—)

Reference Example 34

3′-O-benzyl-5′-O-phenoxymethylcarbonyl-2′-deoxy-5-fluorouridine

Yield 90%
M.p.-(oily)
NMR (CDCl$_3$)δ: 10.03 (1H, bs, —NH—, disappeared by addition of D$_2$O) 7.58 (1H, d, J=6 Hz, C$_6$—H) 7.35–6.77 (10H, m, phenyl-H) 6.22 (1H, t, J=6 Hz, C$_1'$—H) 4.65 (2H, s,

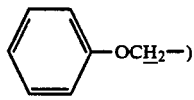

4.42–4.23 (5H, m, C$_{3',5'}$—H,

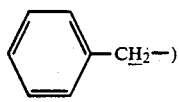

3.97–3.84 (1H, m, C$_{4'}$—H) 2.49–2.23, 1.96–1.65 (1H, m, C$_{2'}$—H)

Reference Example 35

3'-O-benzyl-5'-O-α-naphthylcarbonyl-2'-deoxy-5-fluorouridine

Yield 48%
M.p. 158°–160° C.
NMR (CDCl$_3$)δ: 9.20 (1H, bs, —NH—, disappeared by addition of D$_2$O) 8.87–8.73 (1H, m,

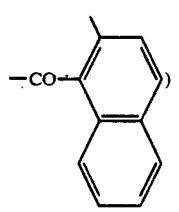

8.10–7.38 (12H, m, C$_6$—H,

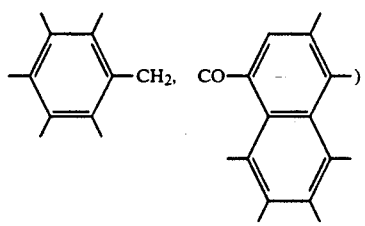

6.25 (1H, t, J=6 Hz, C$_{1'}$—H)
4.68–4.56 (4H, m, C$_{5'}$—H,

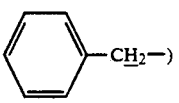

4.45–4.38 (1H, m, C$_{3'}$—H) 4.32–4.18 (1H, m, C$_{4'}$—H) 2.70–2.43, 2.17–1.86 (2H, m, C$_{2'}$—H)

Reference Example 36

3'-O-(4-chlorobenzoyl)-5'-O-benzyl-2'-deoxy-5-fluorouridine

Yield 57%
M.p. 215°–217° C.
NMR(DMSO-d$_6$)δ: 11.83 (1H, bs, —NH—, disappeared by addition of D$_2$O) 8.06–7.97 (3H, m, C$_6$—H,

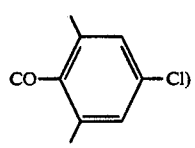

7.61 (2H, d, J=8 Hz,

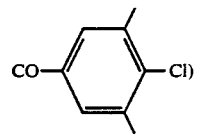

7.35 (5H, s,

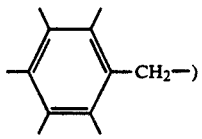

6.27 (1H, t, J=6 Hz, C$_{1'}$—H) 5.54–5.47 (1H, m, C$_{3'}$—H) 4.60 (2H, s,

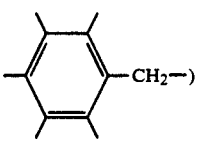

4.42–4.32 (1H, m, C$_{4'}$—H) 3.80–3.71 (2H, m, C$_{5'}$—H) 2.52–2.38 (2H, m, C$_{2'}$—H)

Reference Example 37

3'-O-benzyl-5'-O-(3,4,5-trimethoxybenzoyl)-2'-deoxy-5-fluorouridine

Yield 63%
NMR(DMSO-d$_6$)δ: 11.87 (1H, s, —NH—, disappeared by addition of D$_2$O) 7.93 (1H, d, J=7 Hz, C$_6$—H) 7.33 (5H, s,

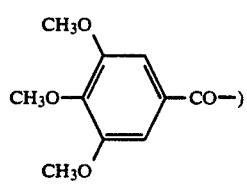

7.25 (2H, s,

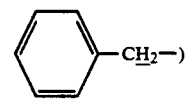

6.17 (1H, t, J=7 Hz, C$_{1'}$—H) 4.61–4.35 (6H, m, C$_{3'}$, $_{4'}$, $_{5'}$—H, 3.82, 3.77 (total 9H, each s

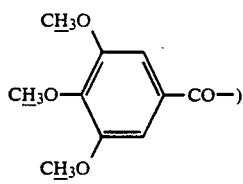

2.54–2.39 (2H, m, C$_{2'}$—H)

Reference Example 38

3'-O-(4-chlorobenzyl)-5'-O-acetyl-2'-deoxy-5-fluorouridine

Yield 90%
NMR(CDCl$_3$)δ: 7.67 (1H, d, J=6 Hz, C$_6$—H) 7.28 (5H, s, phenyl-H) 6.22 (1H, t, J=6 Hz, C$_{1'}$—H) 4.50 (2H, s,

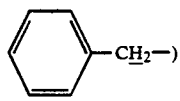

4.40–4.11 (4H, m, C$_{3'.4'.5'}$—H) 2.71–2.46, 2.28–1.93 (5H, m, C$_{2'}$—H, CH$_3$CO—)

Reference Example 39

Preparation of 3'-O-benzyl-2'-deoxy-5-fluoro-3-phenoxycarbonyluridine

To a solution of 0.50 g of 3'-0-benzyl-2'-deoxy-5-fluorouridine in 20 ml of dioxane were added 0.38 ml of trimethylchlorosilane and 1.04 ml of triethylamine, and the mixture was stirred at room temperature for 2 hours. Then, the resulting mixture was left to stand at 60° C. for 30 minutes. To the reaction mixture were added 0.40 g of phenoxycarbonylchloride and 1.00 ml of triethylamine, and the mixture was left to stand at 60° C. for 3 hours. The solvent was distilled off and the residue was dissolved in 50 ml of ethyl acetate. Then, the solution was washed with saturated aqueous solution of sodium chloride. The ethyl acetate layer was separated and concentrated. The residue was dissolved in 30 ml of methanol and 0.5 ml of acetic acid was added thereto. The mixture was left to stand overnight and the resulting mixture was concentrated. The residue was applied to a silica gel column to conduct gradient elution using chloroform and mixtures of methanol (up to 2%) and chloroform, giving 0.58 g of the title compound in a yield of 86%.

M.p. 110°–112° C.
NMR(CDCl$_3$)δ: 8.16 (1H, d, J=7 Hz, C$_6$—H) 7.34–7.22 (10H, m, phenyl-H) 6.27 (1H, t, J=6 Hz, C$_{1'}$—H) 4.49 (2H, s,

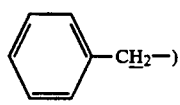

4.26–4.17 (2H, m, C$_{3'.4'}$—H) 3.95–3.60 (2H, m, C$_{5'}$—H) 2.63–1.98 (2H, m, C$_{2'}$—H)

Elementary Analysis: for C$_{23}$H$_{21}$FN$_2$O$_7$ Calcd. (%) C 60.53; H 4.64; N 6.14 Found (%) C 60.60; H 4.72; N 6.08

Reference Example 40

The general procedure of Reference Example 39 was followed, thereby giving the following compound.

3'-O-benzyl-2'-deoxy-3-(4-propoxybenzoyl)-5-fluorouridine

Yield 65%
M.p.-(glassy powder)
NMR(CDCl$_3$)δ: 8.19 (1H, d, J=7 Hz, C$_6$—H) 7.85 (2H, d, J=9 Hz,

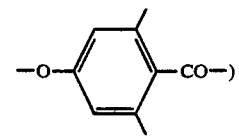

7.27 (5H, s,

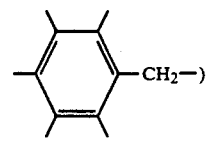

6.90 (2H, d, J=9 Hz,

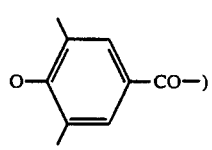

6.25 (1H, t, J=6 Hz, C$_{1'}$—H) 4.44 (2H, s,

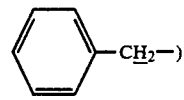

4.20–3.55 (6H, m, C$_{3'.4'.5'}$—H, —CH$_2$CH$_2$O—) 2.57–1.58 (4H, m, C$_{2'}$—H, CH$_3$CH$_2$CH$_2$O—) 0.99 (3H, t, J=7 Hz, CH$_3$CH$_2$—)

Reference Example 41

Preparation of 3'-O-benzyl-2'-deoxy-3-benzoyl-5-fluorouridine

To a solution of 0.50 g of 3'-O-benzyl-2'-deoxy-5-fluorouridine in 20 ml of dioxane were added 0.75 ml of trimethylchlorosilane and 2.00 ml of triethylamine, and the mixture was stirred at room temperature for 2 hours. Then, the resulting mixture was left to stand at 60° C. for 30 minutes. To the reaction mixture were added 0.42 g of benzoyl bromide and 1.00 ml of triethylamine, and the mixture was left to stand at 60° C. for 1 hour. The solvent was distilled off and the residue was dissolved in 50 ml of ethyl acetate. Then, the solution was washed with saturated aqueous solution of sodium chloride. The ethyl acetate layer was separated and concentrated. The residue was dissolved in 30 ml of methanol and 0.5 ml of acetic acid was added thereto. The mixture was left to stand overnight. The solvent was distilled off and the residue was applied to a silica gel column to conduct gradient elution using chloroform and mixtures of methanol (up to 2%) and chloroform, giving 0.35 g of the title compound as a powder in a yield of 54%.

M.p.-(glassy powder)

NMR (CDCl$_3$)δ: 8.19 (1H, d, J=7 Hz, C$_6$—H), 7.94–7.85 (2H, m,

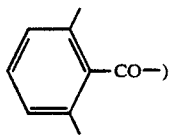

7.64–7.21 (8H, m,

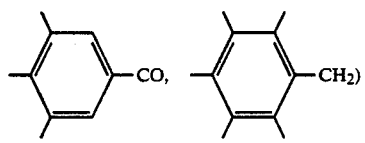

6.24 (1H, t, J=6 Hz, C$_{1'}$—H) 4.46 (2H, s,

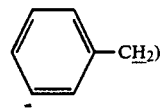

4.24–4.12 (2H, m, C$_{3',4'}$—H) 3.92–3.56 (2H, m, C$_{5'}$—H) 2.60–1.96 (2H, m, C$_{2'}$—H)

Reference Example 42

Preparation of 5'-O-acetyl-3'-O-benzyl-3-benzoyl-2'-deoxy-5-fluorouridine

To a solution of 0.20 g of 5'-O-acetyl-3'-O-benzyl-2'-deoxy-5-fluorouridine in 10 ml of dioxane were added 0.29 g of benzoyl chloride and 0.73 ml of triethylamine, and the mixture was left to stand at 80° C. for 2 hours. The solvent was distilled off and the residue was dissolved in 50 ml of ethyl acetate. The solution was washed with water. The ethyl acetate layer was dried over anhydrous sodium sulfate and concentrated. The concentrate was placed on a silica gel column and eluted with chloroform, giving 0.2 g of the title compound as an oil in a yield of 78%.

NMR(CDCl$_3$)δ: 7.95–7.27 (11H, m, phenyl-H, C$_6$—H) 6.20 (1H, t, J=6 Hz, C$_{1'}$—H) 4.45 (2H, s,

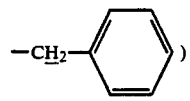

4.23–4.08 (4H, m, C$_{3',4',5'}$—H) 2.60–2.05 (5H, m, C$_{2'}$—H, COCH$_3$)

Elementary Analysis: for C$_{25}$H$_{23}$FN$_2$O$_7$ Calcd. (%) C 62.24; H 4.80; N 5.81 Found (%) C 62.34; H 5.06; N 5.77

Reference Examples 43–53

The general procedure of Reference Example 42 was followed, thereby giving the following compounds.

Reference Example 43

3'-O-benzyl-5'-O-acetyl-2'-deoxy-3-(4-propoxybenzoyl)-5-fluorouridine

Yield 38%

M.p.-(oily)

NMR(CDCl$_3$)δ: 7.85 (2H, d, J=9 Hz,

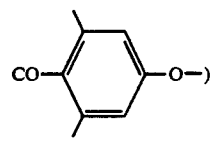

7.75 (1H, d, J=7 Hz, C$_6$—H) 7.30 (5H, s,

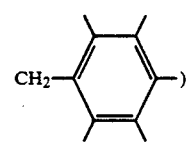

6.92 (2H, d, J=9 Hz,

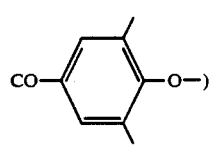

6.20 (1H, t, J=6 Hz, C$_{1'}$—H) 4.45 (2H, s,

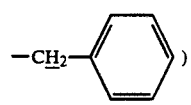

4.23–4.08 (4H, m, C$_{3',4',5'}$—H) 3.96 (2H, t, J=6 Hz, —OCH$_2$CH$_2$CH$_3$) 2.70–1.68 (7H, m, C$_{2'}$—H, COCH$_3$, —OCH$_2$CH$_2$CH$_3$) 1.01 (3H, t, J=7 Hz, —O(CH$_2$)$_2$CH$_3$)

Reference Example 44

3'-O-benzyl-5'-O-acetyl-2'-deoxy-3-(4-chlorobenzoyl)-5-fluorouridine

Yield 73%

M.p.-(oily)

NMR (CDCl$_3$)δ: 7.84 (2H, d, J=9 Hz,

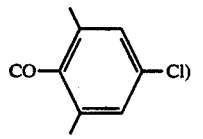

7.78 (1H, d, J=6 Hz, C$_6$—H) 7.44 (2H, d, J=9 Hz.

7.47–7.16 (7H, m,

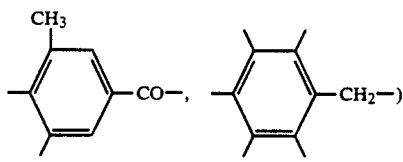

6.20 (1H, t, J=6 Hz, C$_{1'}$—H) 4.46 (2H, s,

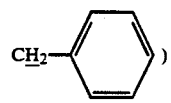

4.25–4.08 (4H, m, C$_{3',4',5'}$—H)
2.67–2.00 (8H, m, C$_{2'}$—H, COCH$_3$,

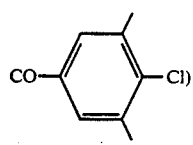

7.30 (5H, s,

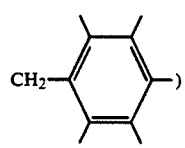

6.20 (1H, t, J=6 Hz, C$_{1'}$—H) 4.51 (2H, d, J=1 Hz,

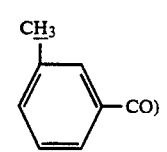

Reference Example 47
3'-O-benzyl-5'-acetyl-2'-deoxy-3-(4-methylbenzoyl)-5-fluorouridine Yield 84%
M.p.-(oily)
NMR(CDCl$_3$)δ: 7.79 (2H, d, J=8 Hz,

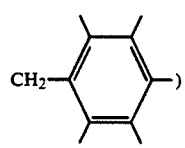

4.28–4.08 (4H, m, C$_{3',4',5'}$—H) 2.70–2.43, 2.25–2.03 (5H, m, C$_{2'}$—H, COCH$_3$)

Reference Example 45
3'-O-benzyl-5'-O-acetyl-2'-deoxy-3-(2-methylbenzoyl)-5-fluorouridine Yield 44%
M.p.-(oily)
NMR(CDCl$_3$)δ: 7.62–7.32 (10H, m, C$_6$—H, phenyl-H) 6.19 (1H, t, J=7 Hz, C$_{1'}$—H) 4.47 (2H, d, J=1 Hz,

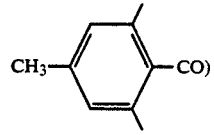

7.78 (1H, d, J=7 Hz, C$_6$—H) 7.27 (5H, s

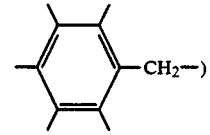

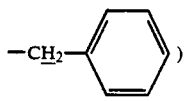

4.25–4.07 (4H, m, C$_{3',4',5'}$—H) 2.67–2.00 (8H, m, C$_{2'}$—H, COCH$_3$,

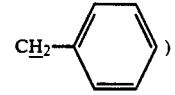

Reference Example 46
3'-O-benzyl-5'-O-acetyl-2'-deoxy-3-(3-methylbenzoyl)-5-fluorouridine Yield 68%
M.p.-(oily)
NMR(CDCl$_3$)δ: 7.81–7.65 (3H, m, C$_6$—H,

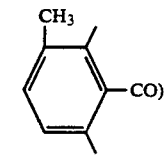

7.22 (2H, d, J=8 Hz,

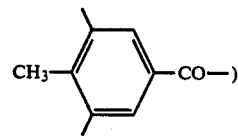

6.20 (1H, 6, J=6 Hz, C$_{1'}$—H) 4.45 (2H, s,

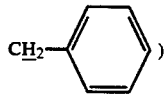

4.24–4.08 (4H, m, C$_{3',4',5'}$—H) 2.60–2.05 (8H, m, C$_{2'}$—H, COCH$_3$,

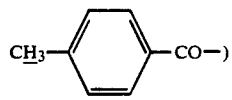

Reference Example 48

3'-O-benzyl-5'-O-acetyl-2'-deoxy-3-(4-methoxybenzoyl)-5-fluorouridine

Yield 70%
M.p.-(powder)
NMR(CDCl$_3$)δ: 7.85 (2H, d, J=8 Hz,

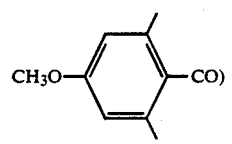

7.77 (1H, d, J=7 Hz, C$_6$—H) 7.28 (5H, s,

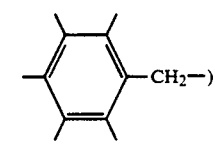

6.91 (2H, d, J=8 Hz,

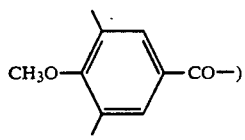

6.21 (1H, t, J=6 Hz, C$_{1'}$—H) 4.47 (2H, s,

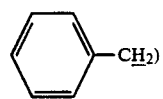

4.25–4.09 (4H, m, C$_{3',4',5'}$—H) 3.80 (3H, s, CH$_3$O—) 2.49–2.07 (5H, m, C$_{2'}$—H, COCH$_3$)

Reference Example 49

3'-O-benzyl-5'-O-benzoyl-2'-deoxy-3-benzoyl-5-fluorouridine

Yield 94%
M.p.-(oily)
NMR(CDCl$_3$)δ: 8.03–7.32 (16H, m, phenyl-H, C$_6$—H) 6.20 (1H, t, J=6 Hz, C$_{1'}$—H) 4.48–4.16 (6H, m, C$_{3',4',5'}$—H,

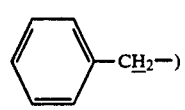

2.70–2.42, 2.25–1.95 (2H, m, C$_{2'}$—H)

Reference Example 50

3'-O-benzyl-5'-O-phenoxycarbonyl-2'-deoxy-3-phenoxycarbonyl-5-fluorouridine

Yield 48%
M.p.-(oily)
NMR(DMSO-d$_6$)δ: 8.21 (1H, d, J=7 Hz, C$_6$—H) 7.57–7.16 (15H, m, phenyl-H) 6.20 (1H, t, J=7 Hz, C$_{1'}$—H) 4.59–4.28 (6H, m, C$_{3',4',5'}$—H,

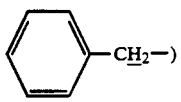

2.54–2.38 (2H, m, C$_{2'}$—H)

Reference Example 51

3'-O-benzyl-5'-O-α-naphthylcarbonyl-2'-deoxy-3-α-naphthylcarbonyl-5-fluorouridine Yield 29%
M.p.-(oily)
NMR(CDCl$_3$)δ: 9.11–8.79 (2H, m,

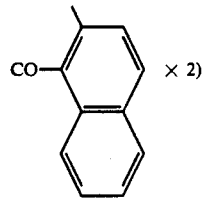

8.11–7.19 (13H, m,

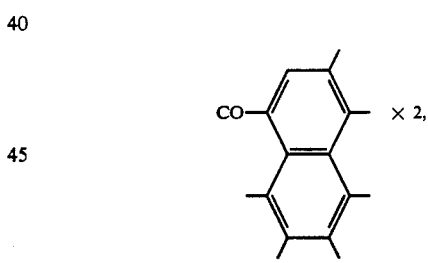

6.20 (1H, t, J=7 Hz, C$_{1'}$—H) 4.71–4.10 (6H, m, C$_{3',4',5'}$—H,

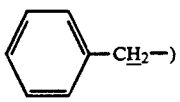

2.64–2.36, 2.15–1.85 (2H, m, C$_{2'}$—H)

Reference Example 52

3'-O-benzyl-5'-O-(3-methylbenzoyl)-2'-deoxy-3-(3-methylbenzoyl)-5-fluorouridine

Yield 18%
M.p.-(oily)
NMR(CDCl$_3$)δ: 7.81–7.62 (5H, m,

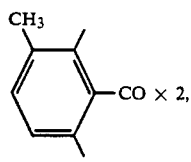

$C_6$—H) 7.43-7.42 (9H, m,

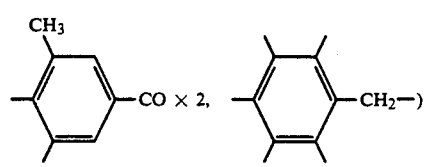

6.23 (1H, t, J=6 Hz, $C_{1'}$—H) 4.60-4.20 (6H, m, $C_{3',4',5'}$—H,

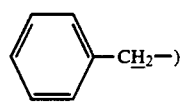

2.78-2.50, 2.24-1.93 (2H, m, $C_{2'}$—H) 2.39, 2.37 (each s, 3H,

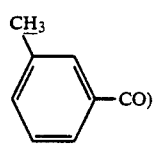

Reference Example 53

3'-O-benzyl-5'-O-acetyl-2'-deoxy-3-hexanoyl-5-fluorouridine

Yield 48%
M.p.-(oily)
NMR(CDCl$_3$)δ: 7.66 (1H, d, J=6 Hz, $C_6$—H) 7.32 (5H, s, phenyl-H) 6.20 (1H, t, J=6 Hz, $C_{1'}$—H) 4.54 (2H, s,

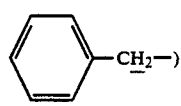

4.38-4.07 (4H, m, $C_{3',4',5'}$—H) 2.82 (2H, t, J=9 Hz, —CH$_2$—CO—) 2.59-2.44, 2.22-2.02 (5H, m, $C_{2'}$—H and CH$_3$CO—) 1.92-1.67 (2H, m,—CH$_2$CH$_2$CO—) 1.56-1.22 (4H, m, CH$_3$CH$_2$CH$_2$CH$_2$CH$_2$CO—) 0.90 (3H, t, J=5 Hz, CH$_3$CH$_2$)

Reference Example 54

Preparation of
3'-O-benzyl-5'-O-acetyl-2'-deoxy-5-fluorouridine

A 3.33 ml quantity of acetic anhydride was added to a solution of 3.95 g of 3'-O-benzyl-2'-deoxy-5-fluorouridine in 30 ml of pyridine, and the mixture was left to stand at 40° C overnight. The solvent was distilled off and the residue was dissolved in 30 ml of ethyl acetate. The solution was washed twice with 15 ml of water. The ethyl acetate layer was dried over anhydrous sodium sulfate and concentrated. The concentrate was placed on a silica gel column and eluted with chloroform, giving 3.62 g of the title compound in a yield of 81.5%.

M.p. 87°-88° C.
NMR(DMSO-d$_6$)δ: 11.86 (1H, d, J=4 Hz, —NH—, disappeared by addition of D$_2$O) 7.93 (1H, d, J=7 Hz, $C_6$—H) 7.35 (5H, s, phenyl-H) 6.15 (1H, t, J=6 Hz, $C_{1'}$—H) 4.55 (2H, s,

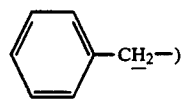

4.32-4.20 (4H, m, $C_{3',4',5'}$—H) 2.39-2.28 (2H, t, J=6 Hz, $C_{2'}$—H) 2.04 (3H, s, COCH$_3$)
Elementary Analysis: for $C_{18}H_{19}FN_2O_6$ Calcd. (%) C 57.14; H 5.06; N 7.40 Found (%) C 56.99; H 5.22; N 7.37

Reference Example 55

Preparation of
3'-O-acetyl-5'-O-benzyl-2'-deoxy-5-fluorouridine

Following the general procedure of Reference Example 54 and using 1.00 g of 5'-O-benzyl-2'-deoxy-5-fluorouridine, 1.00 g of the title compound was prepared in a yield of 88.9%.

M.p. 114°-116° C.
NMR(DMSO-d$_6$)δ: 11.85 (1H, bs, —NH—, disappeared by addition of D$_2$O) 7.95 (1H, d, J=7 Hz, $C_6$—H) 7.34 (5H, s, phenyl-H) 6.17 (1H, t, J=6 Hz, $C_{1'}$—H) 5.25-5.23 (1H, m, $C_{3'}$—H) 4.57 (2H, s,

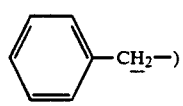

4.32-4.20 (1H, m, $C_{4'}$—H) 3.84-3.73 (2H, m, $C_{5'}$—H) 2.37-2.25 (2H, m, $C_{2'}$—H) 2.06 (3H, s, COCH$_3$)
Elementary Analysis: for $C_{18}H_{19}FN_2O_6$ Calcd. (%) C 57.14; H 5.06; N 7.40 Found (%) C 56.91; H 5.32; N 7.25

Reference Example 56

Preparation of
3'-O-benzyl-5'-O-chloroacetyl-2'-deoxy-5-fluorouridine

Chloroacetic anhydride was added to a solution of 0.20 g of 3'-O-benzyl-2'-deoxy-5-fluorouridine in 10 ml of pyridine, and the mixture was left to stand at room temperature overnight. Then the same subsequent procedures as in Reference Example 54 were conducted, giving 0.11 g of the title compound as an oil in a yield of 45%.

NMR(CDCl$_3$)δ: 10.22 (1H, bs, —NH—, disappeared by addition of D$_2$O) 7.60 (1H, d, J=6 Hz, $C_6$—H) 7.32 (5H, s, phenyl-H) 6.23 (1H, t, J=6 Hz, $C_{1'}$—H) 4.53 (2H, d, J=3 Hz,

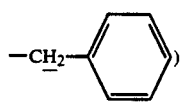

4.45-4.08 (6H, m, $C_{3',4',5'}$—H, ClCH$_2$CO—) 2.69-2.06 (2H, m, $C_{2'}$—H)

Elementary Analysis: for $C_{18}H_{18}ClFN_2O_6$ Calcd. (%) C 52.37; H 4.39; N 6.79 Found (%) C 52.43; H 4.63; N 6.80

Reference Example 57

Preparation of 3'-O-benzyl-2'-deoxy-3-(2-tetrahydrofuranyl)-5-fluorouridine

A 1.32 g quantity of N,O-bis(trimethylsilyl)-acetamide was added with stirring to a suspension of 0.40 g of 3'-O-benzyl-2'-deoxy-5-fluorouridine in 8 ml of dry dichloromethane at room temperature. To the mixture were added, after 4 hours, 0.32 g of 2-acetoxytetrahydrofuran and a solution of 0.1 ml of stannic chloride in 1.6 ml of dry dichloromethane. The mixture was stirred for 1.5 hours and neutralized with 0.64 ml of triethylamine and washed with water. The dichloromethane layer was concentrated and the residue was dissolved in 16 ml of methanol. To the solution was added 0.24 ml of acetic acid and the mixture was left to stand for 3 hours at 40° C. The solvent was distilled off and the residue was subjected to silica gel column chromatography to conduct a gradient elution using chloroform and mixtures of methanol (up to 4%) and chloroform, giving 0.3 g of the title compound in a yield of 77%.

NMR(CDCl$_3$)δ: 8.01 (1H, d, J=6 Hz, C$_6$—H) 7.30 (5H, s, phenyl-H) 6.58 (1H, bt, J=6 Hz,

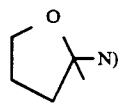

6.26 (1H, bt, J=6 Hz, C$_{1'}$—H) 4.51 (2H, s,

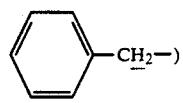

4.39–3.50 (7H, m, C$_{3'.4'.5'}$—H, C$_{6'}$—OH,

2.60–1.86 (6H, m, C$_{2'}$—H,

Elementary Analysis: for $C_{20}H_{23}FN_2O_6$ Calcd (%) C 59.11; H 5.70; N 6.89 Found (%) C 59.02; H 6.11; N 6.78

Reference Example 58

Preparation of 5'-O-acetyl-3'-O-benzyl-3'-(3-carbomethoxybenzoyl)-2'-deoxy-5-fluorouridine To a solution of 3.00 g of 5'-O-acetyl-3'-O-benzyl-2'-deoxy-5-fluorouridine in 100 ml of dry dioxane were added 2.40 g of isophthaloyl chloride and 8.5 ml of triethylamine, and the mixture was refluxed for 2 hours. Then, to the reaction mixture were added 5 ml of methanol and a suspension of 9.60 ml of triethylamine in 100 ml of dry dioxane, and the mixture was refluxed for 2 hours. The insolubles were removed by filtration and the filtrate was concentrated. The residue was dissolved in 100 ml of ethyl acetate, and the solution was washed twice with 30 ml of saturated aqueous solution of sodium chloride. The ethyl acetate layer was dried over anhydrous sodium sulfate and concentrated. The residue was placed on a silica gel column to conduct a gradient elution using chloroform and mixtures of methanol (up to 2%) and chloroform. The fractions corresponding to the title compound were collected and concentrated to dryness, giving the title compound as a powder in a yield of 69%.

NMR(CDCl$_3$)δ: 8.54–7.47 (5H, m, C$_6$—H and

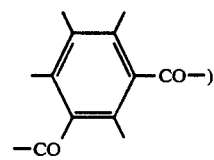

7.28 (5H, s,

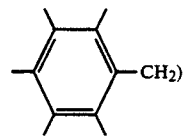

6.20 (1H, t, J=6 Hz, C$_{1'}$—H) 4.50 (2H, s,

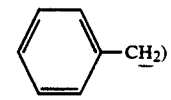

4.48–4.13 (4H, m, C$_{3'.4'.5'}$—H) 3.89 (3H, s, —COOCH$_3$) 2.50–1.93 (5H, m, C$_{2'}$—H and COCH$_3$)

Reference Example 59

Preparation of 3'-O-benzyl-2'-deoxy-5-fluoro-5'-O-(3,4-methylenedioxybenzoyl)uridine The general procedure of Reference Example 26 was followed, thereby producing the title compound in a yield of 72%.

M.p. 169°–171° C.

NMR(CDCl$_3$)δ: 9.72 (1H, bs, —NH—, disappeared by addition of D$_2$O) 7.71–7.52 (2H, m, C$_6$—H and

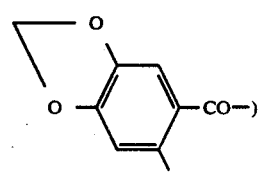

7.38 (1H, d, J=2 Hz,

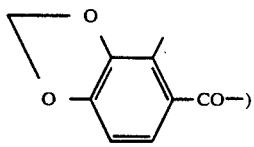

7.32 (5H, s,

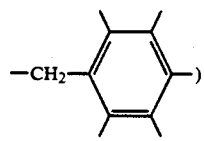

6.83 (1H, d, J=8 Hz,

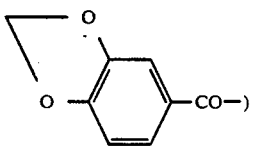

6.23 (1H, t, J=6 Hz, C$_{1'}$—H) 6.03 (2H, s, —OCH$_2$O—) 4.57–4.14 (6H, m,

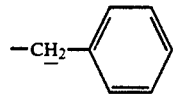

and C$_{3'.4'.5'}$—H) 2.75–2.49 and 2.19–1.89 (2H, m, C$_{2'}$—H)

Reference Example 60

Preparation of 3'-O-benzyl-5'-O-(4-chlorobenzoyl)-2'-deoxy-5-fluorouridine

The general procedure of Reference Example 26 was followed, thereby producing the title compound in a yield of 53%.

NMR(DMSO-d$_6$)δ: 11.9 (1H, bs, —NH—, disappeared by addition of D$_2$O) 7.95 (2H, d, J=9 Hz,

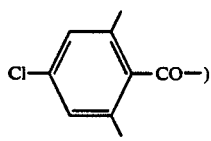

7.92 (1H, d, J=6 Hz, C$_6$—H) 7.59 (2H, d, J=9 Hz,

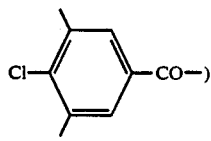

7.33 (5H, s,

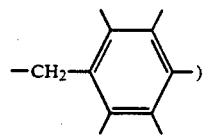

6.15 (1H, t, J=6 Hz, C$_{1'}$—H)
4.58–4.31 (6H, m, C$_{3'.4'.5'}$—H and

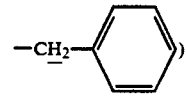

2.42–2.31 (2H, m, C$_{2'}$—H)

Reference Example 61

Preparation of 3'-O-(3-chlorobenzyl)-2'-deoxy-5-fluorouridine

A 2.00 g quantity of potassium hydroxide was dissolved in a mixture of 75 ml of water and 40 ml of dioxane. To the solution were added 1.00 g of 2'-deoxy-5-fluorouridine and 2.50 g of 3-chlorobenzyl chloride, and the resulting mixture was stirred at 45° C. for 3 days. After the reaction, the same subsequent procedure as in Reference Examples 4 and 5 was carried out, and the residue was placed on a silica gel column to conduct a gradient elution with chloroform and mixtures of methanol (up to 2%) and chloroform, thereby producing 0.21 g of the title compound in a yield of 14%.

M.p. 153°–155° C.

Reference Example 62

Preparation of 3'-O-(2-chlorobenzyl)-2'-deoxy-5-fluorouridine

A 3.75 g quantity of potassium hydroxide was dissolved in a mixture of 150 ml of water and 40 ml of dioxane. To the solution were added 1.00 g of 2'-deoxy-5-fluorouridine and 10 ml of 2-chlorobenzyl chloride, and the resulting mixture was stirred at 30° C. for 3 days. After the reaction, the same subsequent procedure as in Reference Examples 4 and 5 was carried out, and the residue was placed on a silica gel column and eluted with 2% methanol-chloroform, thereby producing 0.34 g of the title compound in a yield of 23%.

M.p. 78°–80° C.

Reference Example 63

Preparation of 2'-deoxy-5-fluoro-3'-O-(4-fluorobenzyl)uridine

A 7.5 g quantity of potassium hydroxide was dissolved in a mixture of 300 ml of water and 80 ml of dioxane. To the solution were added 2.00 g of 2'-deoxy-5-fluorouridine and 4.9 ml of 4-fluorobenzyl chloride, and the resulting mixture was stirred at 35° C. for 2 days. After the reaction, the same subsequent procedure as in Reference Examples 4 and 5 was carried out, and the residue was placed on a silica gel column and eluted with 2% methanol-chloroform, thereby producing 0.57 g of the title compound in a yield of 20%.

M.p. 130°–131° C.

Reference Example 64

Preparation of 2'-deoxy-5-fluoro-3'-O-(1-naphthylmethyl)uridine

The general procedures of Reference Examples 4 and 5 were followed using 1.3 g of potassium hydroxide, 1.00 g of 2'-deoxy-5-fluorouridine and 2.7 g of 1-naphthylmethyl bromide, thereby producing 0.28 g of the title compound in a yield of 18%.

M.p. 159°–160° C.

Reference Example 65

Preparation of 5'-O-acetyl-3–0-benzoyl-3'-O-(4-chlorobenzyl)-2'-deoxy-5-fluorouridine To a solution of 0.25 g of 3'-O-(4-chlorobenzyl)-5'-O-acetyl-2'-deoxy-5-fluorouridine in 30 ml of dioxane were added 0.26 g of benzoyl chloride and 0.51 ml of triethylamine, and the mixture was stirred at 90° C. for 2 hours. The reaction mixture was concentrated and the residue was dissolved in 50 ml of ethyl acetate. The solution was washed three times with a saturated aqueous solution of sodium hydrogen carbonate and dried over anhydrous sodium sulfate. The ethyl acetate was distilled off, and the residue was placed on a silica gel column and eluted with chloroform, thereby producing 0.29 g of the title compound in a yield of 92%.

NMR(CDCl$_3$)δ: 7.98–7.87 (2H, m,

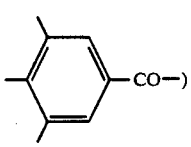

7.77 (1H, d, J=6 Hz, C$_6$—H) 7.69–7.32 (3H, m,

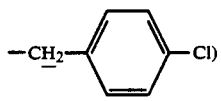

7.27 (4H, d, J=3 Hz, phenyl-H) 6.21 (1H, t, J=4 Hz, C$_{1'}$—H) 4.90 (2H, d, J=1 Hz,

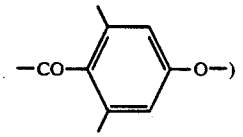

4.32–4.03 (4H, m, C$_{3'.4'.5'}$—H) 2.72–1.96 (5H, m, C$_{2'}$—H and CH$_3$CO—)

Reference Example 66

Preparation of 5'-O-acetyl-3-(4-chlorobenzoyl)-3'-O-(4-chlorobenzyl)-2'-deoxy-5-fluorouridine To a solution of 0.30 g of 3'-O-(4-chlorobenzyl)-5'-O-acetyl-2'-deoxy-5-fluorouridine in 30 ml of dioxane were added 0.38 g of 4-chlorobenzoyl chloride and 0.61 ml of triethylamine, and the mixture was stirred at 40° C. for 3 hours. The insolubles were removed by filtration, and the residue was dissolved in 50 ml of ethyl acetate. The solution was washed with water and dried. The ethyl acetate was distilled off, and the residue was placed on a silica gel column and eluted with chloroform-n-hexane (3:2), thereby producing 0.33 g of the title compound in a yield of 82%.

NMR(CDCl$_3$)δ: 7.86 (2H, J=9 Hz,

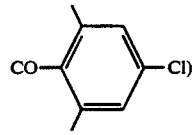

7.77 (1H, d, J=7 Hz, C$_6$—H) 7.48 (2H, d, J=9 Hz,

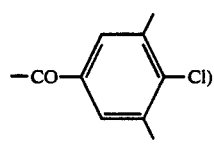

7.27 (4H, d, J=4 Hz,

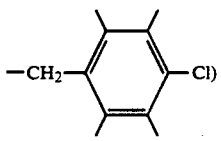

6.20 (1H, t, J=6 Hz, C$_{1'}$—H) 4.49 (2H, s,

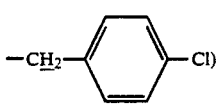

4.32–4.03 (4H, m, C$_{3'.4'.5'}$—H) 2.75–1.95 (5H, m, C$_{2'}$—H and CH$_3$CO—)

Reference Example 67

Preparation of 5'-O-acetyl-3-(4-n-propoxybenzoyl)-3'-O-(4-chlorobenzyl)-2'-deoxy-5-fluorouridine To a solution of 0.30 g of 3'-O-(4-chlorobenzyl)-5'-O-acetyl-2'-deoxy-5-fluorouridine in 30 ml of dioxane were added 0.44 g of 4-n-propoxybenzoyl chloride and 0.61 ml of triethylamine, and the mixture was stirred at 70° C. for 3 hours. The insolubles were removed by filtration, and the residue was dissolved in ethyl acetate. The solution was washed with water and dried. The ethyl acetate was distilled off, and the residue was placed on a silica gel column and eluted with chloroform-petroleum ether (1:1), thereby producing 0.15 g of the title compound in a yield of 36%.

NMR(CDCl$_3$)δ: 7.87 (2H, d, J=9 Hz, 7.74 (1H, d, J=6 Hz, H$_6$) 7.27 (4H, d, J=3 Hz,

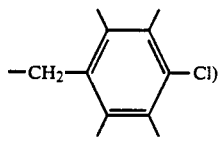

6.94 (2H, d, J=9 Hz,

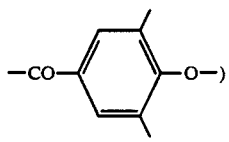

6.21 (1H, t, J=4 Hz, $C_{1'}$—H) 4.49 (2H, s,

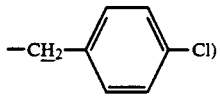

4.31–3.93 (6H, m, $C_{3'\cdot 4'\cdot 5'}$—H and —O—CH$_2$CH$_2$CH$_3$) 2.72–1.65 (7H, m, $C_{2'}$—H, CH$_3$CO— and —O—CH$_2$CH$_2$CH$_3$) 1.04 (3H, t, J=7 Hz, —OCH$_2$CH$_2$CH$_3$)

Reference Example 68

Preparation of 3-benzoyl-3'-O-(4-chlorobenzyl)-2'-deoxy-5-fluorouridine

The general procedure of Reference Example 41 was followed using 0.50 g of 3'-O-(4-chlorobenzyl)-2'-deoxy-5-fluorouridine, thereby producing 0.46 g of the title compound as a powder in a yield of 72%.

M.p.-(powder)
NMR(CDCl$_3$)δ: 8.19 (1H, d, J=6 Hz, $C_6$—H) 7.90 (2H, bd, J=7 Hz,

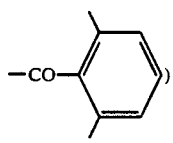

7.65–7.35 (3H, m,

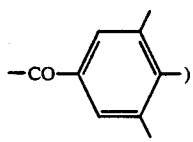

7.24 (4H, s,

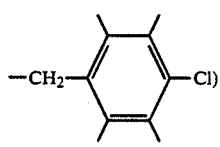

6.24 (1H, t, J=6 Hz, $C_{1'}$—H) 4.42 (2H, s,

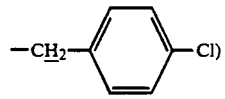

4.24–4.15 (2H, m, $C_{3'\cdot 4'}$—H) 3.95–3.60 (2H, m, $C_{5'}$—H) 2.59–1.98 (2H, m, $C_{2'}$—H)

Reference Example 69

Preparation of 3-benzoyl-5'-O-benzoyl-3'-O-(4-chlorobenzyl)-2'-deoxy-5-fluorouridine A 0.23 ml quantity of benzoyl chloride was added to a solution of 0.25 g of 3'-O-(4-chlorobenzyl)-2'-deoxy-5-fluorouridine in pyridine. The mixture was stirred at room temperature for 2 hours. The solvent was distilled off. To the residue were added ethyl acetate and water to separate the ethyl acetate layer. The ethyl acetate layer was dried over anhydrous sodium sulfate and concentrated. The concentrate was subjected to silica gel column chromatography using chloroform as an eluent, giving 0.27 g of the title compound in a yield of 70%.

NMR(CDCl$_3$)δ: 8.05–7.85 (4H, m,

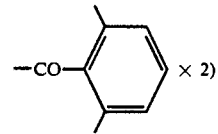

7.71 (1H, d, J=6 Hz, $C_6$—H) 7.63–7.32 (6H, m,

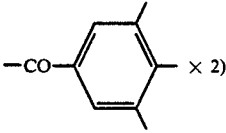

7.25 (4H, s,

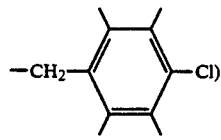

6.21 (1H, t, J=4 Hz, $C_{1'}$—H) 4.63–4.20 (6H, m, $C_{3'\cdot 4'\cdot 5'}$—H and

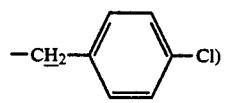

2.77–2.02 (2H, m, $C_{2'}$—H)

Reference Example 70

Preparation of 3'-O-benzyl-2'-deoxy-5-fluoro-3-nicotinoyl-5'-O-nicotinoyluridine A 0.40 g quantity of nicotinoyl chloride hydrochloride and 1.0 ml of triethylamine were added to a solution of 0.50 g of 3'-O-benzyl-2'-deoxy-5-fluorouridine in 40 ml of dioxane. The mixture was refluxed for 6 hours. The solvent was distilled off and the residue was subjected to silica gel column chromatography using 1% methanol-chloroform as an eluent, giving 0.23 g of the title compound in a yield of 29%.

NMR(DMSO-d$_6$)δ: 9.27 and 9.11 (each 1H, d,

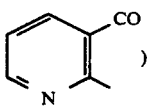
)

8.97-8.81 (2H, m,

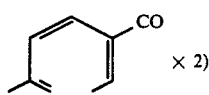
× 2)

8.57-8.16 (3H, m, C$_6$—H and

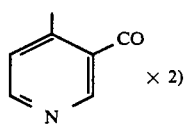
× 2)

7.73-7.50 (2H, m,

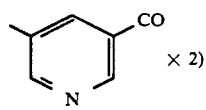
× 2)

7.32 (5H, s,

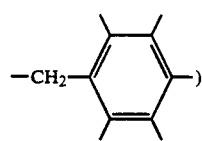
)

6.10 (1H, m, J=6 Hz, C$_1'$—H) 4.59 (2H, s,

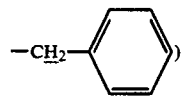
)

4.54-4.33 (4H, m, C$_{3'.4'.5'}$—H) 2.37-2.20 (2H, m, C$_{2'}$—H)

Reference Example 71

Preparation of 2'-deoxy-5-fluoro-3'-O-(4-carboxybenzyl)uridine

Potassium hydroxide (4.30 g) and 1.70 g of 4-methoxycarbonylbenzyl bromide were added to a solution of 3.00 g of 2'-deoxy-5-fluoro-5'-O-trityluridine in 200 ml of dioxane. The mixture was stirred at room temperature for a day. The reaction mixture was concentrated under a reduced pressure. To the concentrate was added 200 ml of water and the mixture was stirred at room temperature for 15 minutes. The reaction mixture was rendered acidic with acetic acid, and extracted with ethyl acetate. The organic layer was dried over magnesium sulfate and concentrated under a reduced pressure. The concentrate was dissolved in 50 ml of a 80% aqueous solution of acetic acid. The solution was heated to 100° C. for 2 hours. The solvent was distilled off and the residue was applied to silica gel column chromatography using 3% methanol-chloroform as an eluent, affording 650 mg of the title compound in a yield of 28%.

NMR(DMSO-d$_6$)δ: 11.83 (1H, bs, N$_3$—H, disappeared by addition of D$_2$O) 8.19 (1H, d, J=7 Hz, C$_6$—H) 7.94 (2H, d, J=8 Hz,

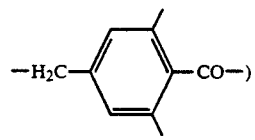
)

7.46 (2H, d, J=8 Hz,

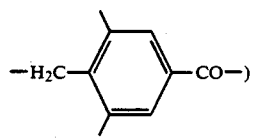
)

6.14 (1H, t, J=6 Hz, C$_1'$—H) 5.20 (1H, bs, C$_5'$—OH, disappeared by addition of D$_2$O) 4.63 (2H, s,

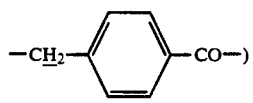
)

4.22-3.64 (4H, m, C$_{3'.4'.5'}$—H) 2.35-2.04 (2H, m, C$_{2'}$—H)

Reference Example 72

Preparation of 2'-deoxy-3'-O-benzyl-5-fluorouridine

In 50 ml of dioxane was dissolved 10 g of 2'-deoxy-5'-O-trityl-5-fluorouridine. To the solution were added 2.9 ml of benzyl bromide and 14.6 g of particles of potassium hydroxide. The mixture was stirred at room temperature for 1 hour. Thereto was added 40 ml of water. The mixture was adjusted to a pH of about 3 to about 4 and extracted with ethyl acetate. The ethyl acetate layer was washed with an aqueous solution of sodium chloride and dried over anhydrous sodium sulfate. The sodium sulfate was separated by filtration and the solvent was distilled off, giving as an intermediate 16.0 g of 2'-deoxy-3'-O-benzyl-5'-O-trityl-5-fluorouridine.

The compound thus obtained was dissolved in 80 ml of a 80% solution of acetic acid to undergo reaction at 50 to 60° C. for 2 hours. The reaction mixture was cooled with ice for 1 hour and 5.1 g of trityl alcohol was removed by filtration. The mother liquor was concentrated and ethanol was added to the concentrate. The mixture was stirred and the crystals thus precipitated were separated by filtration and dried, giving 5.3 g of the title compound in a yield of 75.7%.

M.p. 138°–139° C.

The analysis by NMR showed that the compound obtained above was identical with the compound prepared in Reference Example 2.

Reference Example 73

Preparation of 2'-deoxy-3'-O-benzyl-5-fluorouridine

The general procedure of Reference Example 72 was followed using 2'-deoxy-5'-O-(diphenyl-p-methoxyphenyl)methyl-5-fluorouridine, thereby producing the title compound in a yield of 63%. M.p. 138°–139° C.

The analysis by NMR showed that the compound obtained above was identical with the compound prepared in Reference Example 72.

Reference Example 74

Preparation of 2'-deoxy-3'-O-benzyl-5-fluorouridine

A 10 g quantity of 2'-deoxy-5'-O-trityl-5-fluorouridine was dissolved in 100 ml of dioxane. To the solution were added 2.9 ml of benzyl chloride, 6.9 g of particles of potassium hydroxide and 3.56 g of sodium iodide. The mixture was stirred at 40° C. for 4 hours, and 2.9 ml of benzyl chloride and 1.15 g of potassium hydroxide were added and stirred for 1 hour. Thereto was added water to dissolve the potassium hydroxide in water. The solution was adjusted to a pH of about 3 with acetic acid and extracted with ethylene dichloride. The extract was washed with water and the ethylene dichloride layer was dried over anhydrous sodium sulfate. The sodium sulfate was separated by filtration and the solvent was distilled off, giving 8 g of 2'-deoxy-3'-O-benzyl-5'-O-trityl-5-fluorouridine as an oil.

The compound thus obtained was dissolved in 80 ml of a 80% solution of acetic acid to undergo reaction at 50 to 60° C. for 2 hours. The reaction mixture was cooled with ice for 1 hour. The trityl alcohol was separated by filtration and the filtrate was concentrated. The concentrate was recrystallized from ethanol, giving a first crop of crystals of the title compound in a yield of 70.6%.

The ethanol mother liquor was concentrated and the concentrate was recrystallized from a small amount of ethanol, affording a second crop of crystals of the title compound in a yield of 15.9%.

Overall yield 86.5%

M.p. 138°–139° C.

The analysis by NMR showed that the product was identical with the compound prepared in Reference Example 72.

Reference Example 75

Preparation of 2'-deoxy-3'-O-benzyl-5-fluorouridine

In 50 ml of dioxane was dissolved 10 g of 2'-deoxy-5'-O-trityl-5-fluorouridine. To the solution were added 2.9 ml of benzyl bromide and 14.6 g of particles of potassium hydroxide. The mixture was stirred at room temperature for 1 hour. The solvent was distilled off and the residue was dissolved in 80 ml of a 80% solution of acetic acid to undergo reaction at 50° to 60° C. for 2 hours. The reaction mixture was cooled with ice for 1 hour, the trityl alcohol was separated by filtration and the mother liquor was concentrated. To the concentrate was added ethanol and the mixture was stirred. The crystals precipitated were separated by filtration and dried, affording 5.0 g of the title compound in a yield of 72%.

M.p. 138°–139° C.

The analysis by NMR showed that the compound thus prepared was identical with the compound obtained in Reference Example 72.

Reference Examples 76 to 104

The general procedure of Reference Example 72 was followed, thereby producing compounds identical with those prepared in Reference Examples 1, 3 to 25, 61 to 64 and 71, respectively.

Reference Examples 105 to 133

The general procedure of Reference Example 74 was followed, thereby producing compounds identical with those prepared in Reference Examples 1, 3 to 25, 61 to 64 and 71, respectively.

Reference Example 134

Preparation of 3'-O-benzyl-2'-deoxy-5-fluoro-5'-O-stearoyluridine

The title compound was prepared as an oil by carrying out the same reaction and subsequent treatment as in Reference Example 26. Yield 78%.

NMR(CDCl$_3$)δ: 7.65 (1H, d, J=6 Hz, C$_6$—H) 7.32 (5H, s, phenyl-H) 6.23 (1H, t, J=6 Hz, C$_{1'}$—H) 4.54 (2H, d, J=2 Hz,

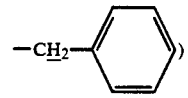

4.29–4.01 (4H, m, C$_{3'·4'·5'}$—H) 2.33–1.83 (4H, m, C$_{2'}$—H and —OCOCH$_2$—) 1.25 (30H, bs, —(CH$_2$)$_{15}$—) 0.88 (3H, t, —CH$_3$)

Reference Example 135

Preparation of 5'-O-cyclohexyl-2'-deoxy-3'-O-(2,4-dichlorobenzyl)-5-fluorouridine The title compound was prepared as an oil by carrying out the same reaction and subsequent treatment as in Reference Example 26. Yield 77%.

NMR(CDCl$_3$)δ: 9.50 (1H, b, NH) 7.67 (1H, d, J=6 Hz, C$_6$—H) 7.40–7.16 (3H, m, phenyl-H) 6.25 (1H, t, J=6 Hz, C$_{1'}$—H) 4.58 (2H, s,

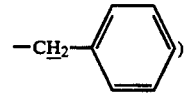

4.37–4.08 (4H, m, C$_{3'·4'·5'}$—H) 2.77–2.51 and 2.48–1.04 (13H, m, C$_{2'}$—H and cyclohexyl-H)

Reference Example 136

Preparation of 2'-deoxy-5-fluoro-3'-O-(4-methoxybenzyl)-5'-O-(2-thenoyl)uridine

The title compound was prepared as a powder by carrying out the same reaction and subsequent treatment as in Reference Example 26. Yield 91%.

NMR(CDCl₃)δ: 9.20 (1H, bs, NH) 7.82 (1H, dd, J₄,₅=4 Hz, J₃,₅=2 Hz,

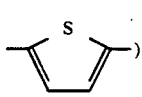

7.63 (1H, d, J=6 Hz, C₆—H) 7.59 (1H, dd, J₃,₄=5 Hz, J₄,₅=4 Hz,

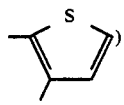

7.29–7.08 (3H, m,

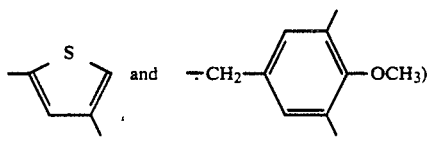

6.87 (2H, d, J=9 Hz,

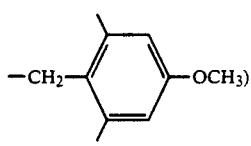

6.25 (1H, t, J=6 Hz, C₁′—H) 4.56–4.10 (6H, m, C₃′,₄′,₅′—H and

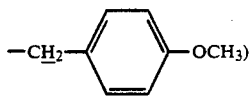

3.78 (3H, s, —OCH₃) 2.74–2.48 and 2.22–1.78 (2H, m, C₂′—H)

Reference Example 137

Preparation of 2′-deoxy-5-fluoro-3′-(3-methylbenzyl)-5′-O-(2-furoyl)uridine

The title compound was prepared as a powder by carrying out the same reaction and subsequent treatment as in Reference Example 26. Yield 85%.

NMR(CDCl₃)δ: 9.14 (1H, bs, NH) 7.93 (1H, d, J=6 Hz, C₆—H) 7.58 (1H, bs,

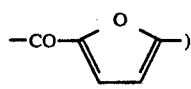

7.29–7.10 (5H, m, furanyl-H,

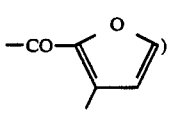

6.55 (1H, dd, J₃,₄=4 Hz, J₄,₅=2 Hz,

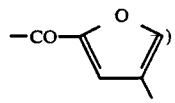

6.35 (1H, t, J=6 Hz, C₁′—H) 4.77–4.10 (6H, m, C₃′,₄′,₅′—H and —CH₂ 2.71–2.44 and 2.34–1.97 (5H, m, C₂′—H and CH₃)

Reference Example 138

Preparation of 3′-O-benzyl-5′-O-crotonoyl-2′-deoxy-5-fluorouridine

The title compound was prepared as a powder in a yield of 75% by carrying out the same reaction and treatment as in Reference Example 54.

NMR(CDCl₃)δ: 8.63 (1H, bs, NH) 7.67 (1H, d, J=6 Hz, C₆—H) 7.32 (5H, s, phenyl-H) 7.14–6.89 (1H, m, —CH=CHCH₃) 6.24 (1H, t, J=6 Hz, C₁′—H) 5.84 (1H, dd, J_{α,β}=16 Hz, J_{α,γ}=2 Hz, —CH=CHCH₃) 4.54 (2H, s,

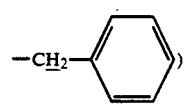

4.42–4.05 (4H, m, C₃′,₄′,₅′—H) 2.73–2.44 and 2.20–2.02 (2H, m, C₂′—H) 1.90 (3H, dd, J_{β,γ}=7 Hz, J_{α,γ}=2 Hz, —CH=CHCH₃)

Reference Example 139

Preparation of 3′-(2-bromobenzyl)-2′-deoxy-5′-O-ethoxyacetyl-5-fluorouridine

A 1.24 g quantity of DCC was added to a solution of 1 g of 3′-(2-bromobenzyl)-2′-deoxy-5-fluorouridine and 0.63 g of ethoxy acetate in 10 ml of pyridine. The mixture was stirred at room temperature for 24 hours. The insolubles were separated by filtration and the filtrate was concentrated. The concentrate was purified with isopropanol-ether, giving 1.06 g of the title compound as a powder in a yield of 80%.

NMR(CDCl₃)δ: 9.49 (1H, bs, NH) 7.74 (1H, d, J=6 Hz, C₆—H) 7.60–7.06 (4H, m, phenyl-H) 6.34 (1H, t, J=6 Hz, C₁′—H) 4.60 (2H, s,

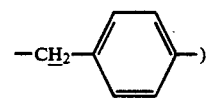

4.39–4.13 (6H, m, C₃′,₄′,₅′—H and —COCH₂O—) 3.59 (2H, q, J=7 Hz, —OCH₂CH₃) 2.73–2.48, 2.31–2.00 (2H, m, C₂′—H) 1.22 (3H, t, J=7 Hz, —OCH₂CH₃)

Reference Example 140

Preparation of 2′-deoxy-5-fluoro-3′-O-(2,4,6-trimethylbenzyl)uridine

A 1.66 g quantity of 2,4,6-trimethylbenzyl chloride was added to a solution of 4.00 g of 2′-deoxy-5-fluoro-5′-O-trityluridine, 2.30 g of potassium hydroxide and 1.47 g of sodium iodide in 50 ml of dried dioxane. The mixture was stirred at 60° C. for 3 hours. The solvent was distilled off, and ethylacetate and water were added to the residue. The ethyl acetate layer was washed with water and dried over anhydrous sodium sulfate. The ethyl acetate was distilled off and the residue was dissolved in 50 ml of a 80% solution of acetic acid. The resulting solution was left to stand at 70° C. for 2 hours. The reaction mixture was concentrated and water was added to the concentrate. The mixture was rendered weakly basic with an aqueous solution of sodium hydroxide and washed with ether. The aqueous layer was made weakly acidic with a 6N solution of hydrochloric acid and extracted with ethyl acetate. The ethyl acetate layer was washed with water, dried over anhydrous sodium sulfate and concentrated. Ether was added to the concentrate to deposit solids and the solids were recrystallized from ethanol, giving 1.69 g of the title compound in a yield of 55%.

M.p 179°-181° C.

NMR(DMSO-d$_6$)δ: 11.82 (1H, bs, NH) 8.20 (1H, d, J=7 Hz, C$_6$—H) 6.83 (2H, s,

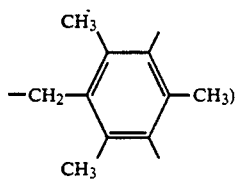

6.07 (1H, bt, J=6 Hz, C$_{1'}$—H) 5.19 (1H, bt, J=5 Hz, 5'—OH) 4.47 (2H, s,

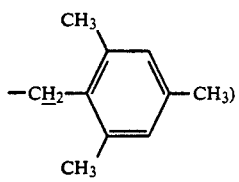

4.20-4.10 (1H, m, C$_{3'}$—H) 4.02-3.91 (1H, m, C$_{4'}$—H) 3.69-3.57 (2H, m, C$_{5'}$—H) 2.29-2.12 (11H, m, CH$_3$×3 and C$_{2'}$—H)

Reference Example 141

Preparation of 2,6-ditrimethylsilyloxypyridine

A 8.00 g quantity of 2,6-dihydroxypyridine was refluxed in 60 ml of hexamethyldisilazane overnight. The excess disilazane was distilled off and the residue was subjected to distillation under a reduced pressure, giving 10.78 g of the title compound having a boiling point of 72° C./1 mmHg in a yield of 61%.

Reference Example 142

Preparation of 2'-deoxy-5-fluoro-3'-O-(4-methoxycarbonylbenzyl)uridine

Pottasium hydroxide (4.30 g) and 1.70 g of 4-methoxycarbonylbenzyl bromide were added to a solution of 3.00 g of 2'-deoxy-5-fluoro-5'-O-trityluridine in 200 ml of dioxane. The mixture was stirred at room temperature for a day. The reaction mixture was concentrated under a reduced pressure. To the concentrate was added 200 ml of ethyl acetate for extraction. The extract was washed with water, dried over magnesium sulfate and concentrated. The concentrate was dissolved in 20 ml of a 80% aqueous solution of acetic acid.

M.p. 169°-170° C.

NMR(CDCl$_3$)δ: 9.85 (1H, bs, N$_3$—H) 8.04-7.94 (3H, m, C$_6$—H and

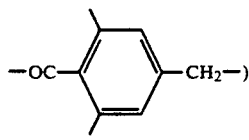

7.37 (2H, d, J=8 Hz,

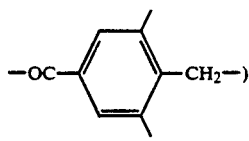

6.24 (1H, t, J=6 Hz, C$_{1'}$—H) 4.58 (2H, s, 3'—O—CH$_2$—) 4.31-3.70 (7H, m, C$_{3'.4'.5'}$—H and —COCH$_3$) 3.19 (1H, bs, C$_{5'}$—OH) 2.66-2.04 (2H, m, C$_{2'}$—H)

Reference Example 143

Preparation of 2'-deoxy-3'-O-cinnamyl-5-fluorouridine

The general procedure of Reference Example 142 was followed, thereby producing the title compound in a yield of 23%.

NMR(DMSO-d$_6$)δ: 11.75 (1H, bs, N$_3$—H) 8.20 (1H, d, J=7 Hz, C$_6$—H) 7.53-7.24 (5H, m,

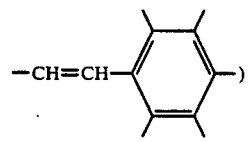

6.64 (1H, d, J=16 Hz,

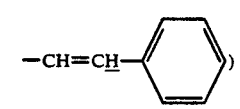

6.47-6.08 (2H, m, C$_{1'}$—H and

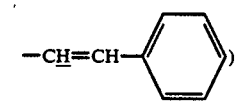

5.20 (1H, bs, C$_{5'—OH}$) 4.17 (2H, d, J=5 Hz, C$_{3'}$—O—CH$_2$—) 4.20-4.03 (2H, m, C$_{3'.4'}$—H) 3.74-3.59 (2H, m, C$_{5'}$—H) 2.34-2.21 (2H, m, C$_{2'}$—H)

Reference Example 144

Preparation of 2'-deoxy-3'-O-(4-dimethlaminobenzyl)-5-fluorouridine

A 0.86 ml quantity of pyridine and 1.19 ml of phosphorus tribromide were added to a solution of 1.60 g of 4-dimethylaminobenzyl alcohol in 20 ml of benzene, and the mixture was stirred at 80° C. for 1 hour. The reaction mixture was concentrated and the concentrate was dissolved in 50 ml of a 2:1 mixture of water and acetonitrile. The resulting mixture was adjusted to a pH of 11 by addition of potassium hydroxide. Thereto was added 1.00 g of 2'-deoxy-5-fluorouridine and the mixture was stirred at room temperature for 2 days.

The reaction mixture was poured into ice water and extracted with ethyl acetate. The organic layer was dried over magnesium sulfate and concentrated. The concentrate was placed on silica gel column and eluted with 1% methanol-chloroform, thereby giving 70 mg of the title compound in a yield of 5%.

NMR(DMSO-d$_6$)δ: 11.98 (1H, bs, N$_3$—H) 8.18 (1H, d, J=7 Hz, C$_6$—H) 7.15 (2H, d, J=9 Hz,

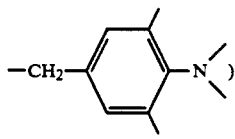

6.69 (2H, d, J=9 Hz,

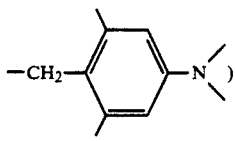

6.09 (1H, t, J=6 Hz, C$_{1'}$—H) 5.18 (1H, bs, C$_{5'}$—OH) 4.38 (2H, s,

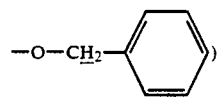

4.18-3.96 (2H, m, C$_{3'.4'}$—H) 3.70-3.58 (2H, m, C$_{5'}$—H) 2.88 (6H, s, CH$_3$×2) 2.28-2.09 (2H, m, C$_{2'}$—H)

Reference Example 145

Preparation of 2'-deoxy-5-fluoro-3'-O-(3-phenylpropyl)uridine

To a solution of 500 mg of the 2'-deoxy-3'-O-cinnamyl-5-fluoro-5'-O-trityluridine prepared in Reference Example 143 in 30 ml of methanol was added 50 mg of 5% palladium-carbon, and the catalytic reduction was conducted at room temperature for 1 hour.

The reaction mixture was filtered and concentrated. The concentrate was dissolved in 20 ml of 80% acetic acid and the solution was stirred at 65° C. for 2 hours. The reaction mixture was concentrated, and the concentrate was placed on a silica gel column and eluted with 1% methanol-chloroform, thereby giving 190 mg of the title compound in a yield of 63%.

NMR(DMSO-d$_6$)δ: 11.80 (1H, bs, N$_3$—H) 8.19 (1H, d, J=7 Hz, C$_6$—H) 7.22 (5H, s,

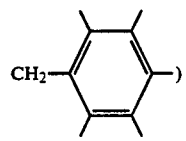

6.12 (1H, t, J=6 Hz, C$_{1'}$—H) 5.18 (1H, t, J=5 Hz, C$_{5'}$—OH) 4.06-3.93 (2H, m, C$_{3'.4'}$—H) 3.66-3.62 (2H, m, C$_{5'}$—H) 3.41 (2H, t, J=6 Hz, C$_{3'}$—O—CH$_2$—) 2.72-1.66 (6H, m, C$_{2'}$—H and

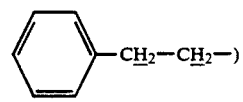

Example 1

Preparation of 5-chloro-2,4-distearoyloxypyridine

A 2.00 g quantity of 5-chloro-4-hydroxy-2-pyridone was refluxed in 150 ml of pyridine to obtain a uniform solution. To the solution was added 5.85 g of stearoyl chloride and the mixture was subjected to reaction at room temperature overnight. After completion of the reaction, the pyridine was concentrated and the concentrate was extracted with petroleum ether. The petroleum ether layer was concentrated and subjected to silica gel column chromatography using as an eluent petroleum ether-chloroform (1:9), giving 1.40 g of the title compound in a yield of 15%.

NMR(CDCl$_3$)δ: 8.39 (1H, s, C$_6$—H of the pyridine ring) 7.04 (1H, s, C$_3$—H of the pyridine ring) 2.50-2.63 (4H, m, CH$_2$CO×2) 0.81-1.77 and 1.26 (66H, m, CH$_2$×30 and CH$_3$×2)

Example 2

Preparation of 5-chloro-4-stearoyloxy-2-pyridone

A 2.00 g quantity of 5-chloro-4-hydroxy-2-pyridone pyridine was reacted in the same manner as in Example 1. After completion of the reaction, the pyridine was distilled off and the residue was washed with petroleum ether and then with water. The solids thus obtained were subjected to silica gel column chromatography using as an eluent 2% methanol-chloroform, giving 1.42 g of the title compound in a yield of 25%.

NMR(DMSO-d$_6$)δ: 11.87 (1H, bs, —NH—) 7.80 (1H, s, C$_6$—H of the pyridine ring) 6.32 (1H, s, C$_3$—H of the pyridine ring) 2.60 (2H, t, J=7 Hz, CH$_2$CO) 1.24 (30H, bs, CH$_2$×15) 0.85 (3H, t, J=7 Hz, CH$_3$)

Example 3

Preparation of 5-chloro-4-(3-methylbenzoyl)oxy-2-pyridone

The general procedure of Example 2 was repeated using 2.00 g of 5-chloro-4-hydroxy-2-pyridone and 3.00 g of 3-methylbenzoyl chloride and also using diethyl ether as a solvent for washing, thereby producing 1.09 g of the title compound in a yield of 30%.

NMR(DMSO-d$_6$)δ: 12.00 (1H, bs, —NH—) 7.94-7.88 (3H, m, C$_6$—H of the pyridine ring and

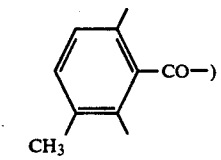

7.57-7.49 (2H, m,

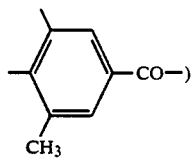

6.54 (1H, s, C$_3$—H of the pyridine ring) 2.42 (3H, s, CH$_3$)

Example 4

Preparation of 4-butanoyloxy-5-chloro-2-pyridone

The general procedure of Example 3 was followed using 2.00 g of 5-chloro-4-hydroxy-2-pyridone and 2.20 g of butanoyloxy chloride, thereby producing 0.38 g of the title compound in a yield of 13%.

NMR(DMSO-d$_6$)δ: 11.90 (1H, bs, —NH—) 7.82 (1H, s, C$_6$—H of the pyridine ring) 6.34 (1H, s, C$_3$—H of the pyridine ring) 2.60 (2H, t, J=7 Hz, CH$_2$CO) 1.66 (2H, m, CH$_2$) 0.97 (3H, t, J=7 Hz, CH$_3$)

Example 5

Preparation of 5-chloro-2,4-dibutanoyloxypyridine

The general procedure of Example 1 was repeated using 2.00 g of 5-chloro-4-hydroxy-2-pyridone and 2.20 g of butanoyl chloride and also using diethyl ether as a solvent for extraction, thereby producing 2.43 g of the title compound in a yield of 50%.

NMR(CDCl$_3$)δ: 8.40 (1H, s, C$_6$—H of the pyridine ring) 7.05 (1H, s, C$_3$—H of the pyridine ring) 2.49–2.70 (4H, m, CH$_2$CO×2) 1.66–1.93 (4H, m, CH$_2$×2) 1.04 (6H, t, J=7 Hz, CH$_3$×2)

Example 6

Preparation of 4-hexanoyloxy-5-chloro-2-pyridone

The general procedure of Example 3 was followed using 2.00 g of 5-chloro-4-hydroxy-2-pyridone and 2.75 g of hexanoyl chloride, thereby producing 1.33 g of the title compound in a yield of 40%.

NMR(DMSO-d$_6$)δ: 11.96 (1H, bs, —NH—) 7.82 (1H, s, C$_6$—H of the pyridine ring) 6.34 (1H, s, C$_3$—H of the pyridine ring) 2.61 (2H, t, J=7 Hz, CH$_2$CO) 1.20–1.79 (6H, m, CH$_2$×3) 0.88 (3H, t, J=6 Hz, CH$_3$)

Example 7

Preparation of 5-chloro-2,4-dihexanoyloxypyridine

The general procedure of Example 5 was followed using 2.00 g of 5-chloro-4-hydroxy-2-pyridone and 2.75 g of hexanoyl chloride to produce 1.22 g of the title compound in a yield of 26%.

NMR(CDCl$_3$)δ: 8.40 (1H, s, C$_6$—H of the pyridine ring) 7.05 (1H, s, C$_3$—H of the pyridine ring) 2.30–2.75 (4H, m, CH$_2$CO×2) 1.28–1.90 (12H, m, CH$_2$×6) 0.86–1.03 (6H, m, CH$_3$×2)

Example 8

Preparation of 5-chloro-2,4-di(3-methylbenzoyloxy)pyridine

The general procedure of Example 5 was followed using 2.00 g of 5-chloro-4-hydroxy-2-pyridone and 3.00 g of 3-methylbenzoyl chloride, thereby producing 1.64 g of the title compound in a yield of 32%.

NMR(CDCl$_3$)δ: 8.51 (1H, s, C$_6$—H of the pyridine ring) 8.03 (4H, bs, 7.48–7.41 (4H, m,

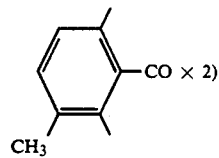

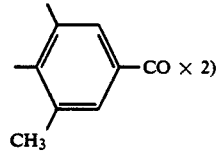

7.37 (1H, s, C$_3$—H of the pyridine ring) 2.46 and 2.44 (6H, each, s, CH$_3$)

Example 9

Preparation of 4-benzoyloxy-2-pyridone 50 ml of a solution of 1.00 g of 4-hydroxy-2-pyridone and 1.35 ml of benzoyl chloride in pyridine was refluxed for 6 hours. After the pyridine was distilled off, the residue was mixed with water. The precipitate was recovered by filtration and was washed with a small amount of ethanol to obtain 0.86 g of the title compound in a yield of 44%.

M.p. 194°–196° C.

Example 10

Preparation of 4-benzoyloxy-5-chloro-2-pyridone

Using 1.00 g of 5-chloro-4-hydroxy-2-pyridone and 0.96 ml of benzoyl chloride and following the general procedure of Example 9, 0.64 g of the title compound was produced in a yield of 37%. M.p. 196°–197° C.

Example 11

Preparation of 4-(3-benzyloxycarbonylbenzoyloxy)-2-pyridone

The general procedure of Example 1 was repeated using 2.80 g of 4-hydroxy-2-pyridone and 14.70 g of 3-benzyloxycarbonylbenzoyl chloride, thereby producing 4.29 g of the title compound in a yield of 49%.

NMR(CDCl$_3$)δ: 8.80–8.84 (1H, m,

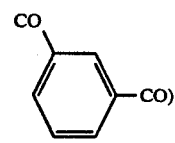

8.35 (2H, dd, J$_{2,4}$=2 Hz, J$_{4,5}$=8 Hz,

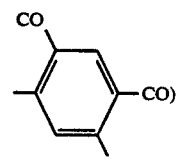

7.66–7.37 (7H, m, phenyl-H and

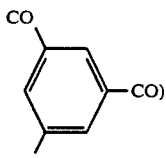

and C$_6$—H of the pyridine ring) 6.53 (1H, d, C$_3$—H of the pyridine ring, J=2 Hz) 6.30 (1H, dd, C$_5$—H of the pyridine ring, J$_{3,5}$=2 Hz, J$_{5,6}$=8 Hz)

Example 12

Preparation of 4-acetoxy-2-pyridone

A 5.00 g quantity of 4-hydroxy-2-pyridone and 3.84 ml of acetyl chloride were reacted for 5 hours in the same manner as in Example 2. The title compound was isolated in an amount of 4.15 g from the reaction mixture in the same manner as in Example 2 except that ethyl acetate was used as extraction solvent. Yield was 60%.

NMR(DMSO-d$_6$)δ: 11.45 (1H, bs, N—H) 7.43 (1H, d, C$_6$—H of the pyridine ring, J=8 Hz) 6.10–6.04 (2H, m, C$_{3,5}$—H of the pyridine ring) 2.24 (3H, s, CH$_3$)

Example 13

Preparation of 4-propanoyloxy-2-pyridone

Using 1.00 g of 4-hydroxy-2-pyridone and 0.94 ml of propanoyl chloride and following the general procedure of Example 12, 350 mg of the title compound was obtained in a yield of 23%.

NMR(DMSO-d$_6$)δ: 11.61 (1H, bs, N—H) 7.43 (1H, d, C$_6$—H of the pyridine ring, J=8 Hz) 6.10–6.02 (2H, m, C$_{3,5}$—H of the pyridine ring) 2.58 (2H, q, —CH$_2$—, J=8 Hz) 1.11 (3H, t, —CH$_3$, J=7.5 Hz)

Example 14

Preparation of 4-n-decanoyloxy-2-pyridone

The general procedure of Example 12 was repeated using 1.00 g of 4-hydroxy-2-pyridone and 2.05 g of n-decanoyl chloride to produce 370 mg of the title compound in a yield of 15%.

NMR(DMSO-d )δ: 11.60 (1H, bs, N—H) 7.42 (1H, d, C$_6$—H of the pyridine ring, J=8 Hz) 6.06–6.03 (2H, m, C$_{3,5}$—H of the pyridine ring) 1.62 (2H, t, CO—CH$_2$, J=6 Hz) 1.39–0.91 (14H, m, CH$_2$×7) 0.79 (3H, t, —CH$_3$, J=6 Hz)

Example 15

Preparation of 4-(2-chlorobenzoyloxy)-2-pyridone

The general procedure of Example 12 was followed using 1.00 g of 4-hydroxy-2-pyridone and 1.36 ml of 2-chlorobenzoyl chloride to produce 1.42 g of the title compound in a yield of 68%.

NMR(DMSO-d$_6$)δ: 11.74 (1H, bs, N—H) 8.12–7.62 (4H, m,

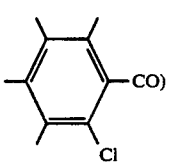

7.51 (1H, d, C$_6$—H of the pyridine ring, J=8 Hz) 6.29–6.20 (2H, m, C$_{3,5}$—H of the pyridine ring)

Example 16

Preparation of 2,4-dinicotinoyloxypyridine

A 1.00 g quantity of 4-hydroxy-2-pyridone and 3.53 g of nicotinoyl acid chloride hydrochloride were reacted in 30 ml of pyridine at room temperature for 2 days. The resultant reaction mixture was treated in the same manner as in Example 12 to obtain 260 mg of the title compound in a yield of 9%.

NMR(CDCl$_3$)δ: 9.40–7.40 (9H, m, C$_6$—H of the pyridine ring and 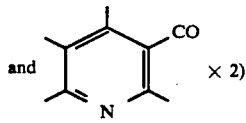

7.36–7.29 (2H, m, C$_{3,5}$—H of the pyridine ring)

Example 17

Preparation of 2,4-di(4-ethoxybenzoyloxy)pyridine

The general procedure of Example 16 was followed using 1.00 g of 4-hydroxy-2-pyridone and 3.32 g of 4-ethoxybenzoyl chloride to produce 220 mg of the title compound in a yield of 6%.

NMR(DMSO-d$_6$)δ: 8.50 (1H, d, C$_6$—H of the pyridine ring, J=6 Hz) 8.14–7.07 (8H, m,

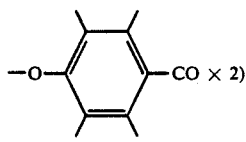

7.48–7.40 (2H, m, C$_{3,5}$—H of the pyridine ring) 4.17 (4H, q, O—CH$_2$×2, J=7 Hz) 1.37 (6H, t, CH$_3$×2, J=7 Hz)

Example 18

Preparation of 4-acetoxy-5-chloro-2-pyridone

A 5.00 g quantity of 5-chloro-4-hydroxy-2-pyridone and 3.66 ml of acetyl chloride were stirred in 250 ml of pyridine at room temperature for 3 hours. The reaction mixture was then concentrated and the concentrate was washed with ethyl acetate and water to produce 3.39 g of the title compound in a yield of 52%.

NMR(DMSO-d$_6$)δ: 11.91 (1H, bs, N—H) 7.81 (1H, s, C$_6$—H of the pyridine ring) 6.35 (1H, s, C$_3$—H of the pyridine ring) 2.32 (3H, s, CH$_3$)

Example 19

Preparation of 4-(2-naphthoyloxy)-2-pyridone

Using 1.00 g of 4-hydroxy-2-pyridone and 2.57 g of β-naphthoyl chloride and following the general procedure of Example 18, 1.65 g of the title compound was produced in a yield of 69%.

NMR(DMSO-d$_6$)δ: 11.72 (1H, bs, N—H) 8.81–7.64 (7H, m, H of the naphthalene ring) 7.51 (1H, d, C$_6$—H of the pyridine ring, J=8 Hz) 6.33–6.25 (2H, m, C$_{3,5}$-H of the pyridine ring)

Example 20

Preparation of 4-(4-nitrobenzoyloxy)-2-pyridone

To a suspension of 1.00 g of 4-hydroxy-2-pyridone in 50 ml of dried dioxane were added 3.78 ml of triethylamine and a solution of 2.17 g of 4-nitrobenzoyl chloride in 30 ml of dried dioxane, and the mixture was refluxed for 6 hours. After the dioxane was distilled off, the residue was washed with water and then with a 1:1 mixture of methanol-acetone to obtain the title compound in an amount of 1.72 g (yield: 73.4%)

M.p. 255°-256° C.

Example 21

Preparation of 4-acetoxy-2-benzoyloxy-5-chloropyridine

The general procedure of Example 20 was repeated using 500 mg of 4-acetoxy-5-chloro-2-pyridone and 0.37 ml of benzoyl chloride to produce 720 mg of the title compound in a yield of 93%.

NMR(CDCl$_3$)$\delta$: 8.46 (1H, s, C$_6$—H of the pyridine ring) 8.24-7.49 (5H, m, H of the benzoyl ring) 7.20 (1H, s, C$_3$—H of the pyridine ring) 2.38 (3H, s, CH$_3$)

Example 22

Preparation of 2,4-diacetoxypyridine

The general procedure of Example 18 was followed using 1.00 g of 4-hydroxy-2-pyridone and 4.00 g of acetyl bromide to obtain 0.90 g of the title compound in a yield of 56.7%.

NMR(CDCl$_3$)$\delta$: 8.36 (1H, d, C$_6$—H of the pyridine ring, J=6 Hz) 7.06 (1H, dd, C$_5$—H of the pyridine ring, J$_{3,5}$=2 Hz, J$_{5,6}$=6 Hz) 6.96 (1H, d, C$_3$—H of the pyridine ring, J=2.0 Hz) 2.31 (3H, s, CH$_3$) 2.30 (3H, s, CH$_3$)

Example 23

Preparation of 4-(3-benzyloxycarbonylpropanoyloxy)-2-pyridone

To a solution of 1.00 g of 4-hydroxy-2-pyridone and 2.00 g of 3-benzyloxycarbonylpropionic acid in 30 ml of dimethylformamide was added at room temperature 1.90 g of N,N'-dicyclohexylcarbodiimide with stirring and the mixture was stirred overnight. The crystals formed were filtered off and the filtrate was concentrated. The concentrate was dissolved in 50 ml of ethyl acetate and washed with 20 ml of water three times. The ethyl acetate layer was dried over anhydrous sodium sulfate and concentrated. The concentrate was then subjected to silica gel column chromatography using as an eluent 2% methanol-chloroform, giving 0.62 g of the title compound in a yield of 23%.

NMR(DMSO-d$_6$)$\delta$: 11.66 (1H,bs, —NH—, disappeared by addition of D$_2$O) 7.48-7.37 (6H, m, phenyl-H and C$_6$—H of the pyridine ring) 6.06-5.96 (2H, m, C$_{3,5}$—H of the pyridine ring) 5.15 (2H, s,

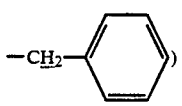

2.90-2.75 (4H, m, —COCH$_2$CH$_2$CO—)

Example 24

Preparation of 4-(3-carboxybenzoyloxy)-2-pyridone 1.00 g of 4-hydroxy-2-pyridone was suspended in 50 ml of pyridine. After the addition of 3.65 g of isophthaloyl chloride, the suspension was refluxed with heating for 1.5 hours. The reaction mixture was left to stand for cooling, to which water was added and the mixture was extracted with ethyl acetate. The ethyl acetate layer was washed with water, dried over magnesium sulfate and concentrated under reduced pressure. The concentrate was washed with ether to give 1.00 g of the title compound in a yield of 43%.

NMR(DMSO-d$_6$)$\delta$: 8.58-7.68 (4H, m, H of the benzoyl ring) 7.50 (1H, d, C$_6$—H of the pyridine ring, J=8 Hz) 6.31-6.25 (2H, m, C$_{3,5}$—H of the pyridine ring)

Example 25

Preparation of 1-(carbomethoxymethylcarbamoyl)-4-hydroxy-2-pyridone

To 50 ml of a suspension of 2.00 g of 4-hydroxy-2-pyridone in dioxane was added 2.49 g of carboxymethylisocyanate and the resultant mixture was refluxed at 80° C. for 2 hours. After completion of the reaction, the dioxane was distilled off and diethylether was added to the residue to produce 2.20 g of the title compound in the form of solid in a yield of 54%.

M.p. 124°-126° C.

NMR(DMSO-d$_6$)$\delta$: 10.87 (2H, bs, —CONH—, OH) 8.22 (1H, d, C$_6$—H, J=8 Hz) 6.18 (1H, dd, C$_5$—H, J$_{3,5}$=2 Hz, J$_{5,6}$=8 Hz) 5.77 (1H, d, C$_3$—H, J=2 Hz) 4.17 (2H, d, CH$_2$, J=4 Hz) 3.69 (3H, s, CH$_3$)

Example 26

Preparation of 6-benzoyloxy-2-pyridone

A 1.60 g quantity of 2,6-bis(trimethylsilyloxy)pyridine was dissolved in 10 ml of acetonitrile and 5 ml of acetonitrile solution containing 1.30 g of benzoyl chloride was added dropwise to the solution. After the mixture was reacted at room temperature for one day, the reaction mixture was concentrated and subjected to silica gel chromatography using chloroform as an eluent to produce 0.50 g of the title compound in a yield of 33%.

NMR(CDCl$_3$)$\delta$: 8.28-8.18 (2H, m,

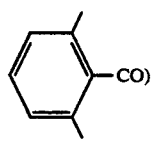

7.26-7.72 (4H, m, C$_4$—H of the pyridine ring and

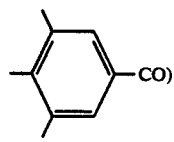

6.77 (1H, d, C$_3$—H or C$_5$—H of the pyridine ring, J=8 Hz) 6.64 (1H, d, C$_5$—H or C$_3$—H of the pyridine ring, J=8 Hz)

Example 27

Preparation of 2-benzoyloxy-4-hydroxypyridine

To 4.0 g of 2,4-bis(trimethylsilyloxy)-pyridine in 50 ml of methylene chloride were added 2.65 g of benzoyl and 0.2 ml of stannic chloride and the mixture was agitated for one hour. After completion of the reaction, the methylene chloride was distilled off and the residue was subjected to silica gel chromatography using as an eluent ethyl acetate-benzene (2:3) to obtain 1.00 g of the title compound in a yield of 29.6%.

M.p. 124°–127° C.

Example 28

Preparation of 4-hydroxy-2-(4-methylbenzoyloxy)-pyridine

To 3.5 g of 2,4-bis(trimethylsilyloxy)-pyridine in 50 ml of methylene chloride was added 2.34 g of p-methylbenzoyl chloride and the mixture was stirred at room temperature for one hour. Following thereafter the general procedure of Example 27, 1.86 g of the title compound was produced in a yield of 59.2%.

M.p. 120°–127° C.

NMR(DMSO-$d_6$)$\delta$: 10.92 (1H, bs, —OH) 8.09 (1H, d, $C_6$—H of the pyridine ring, J=6 Hz) 8.00 (2H, d,

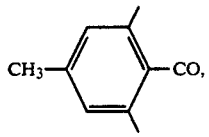

J=8 Hz) 7.41 (2H, d,

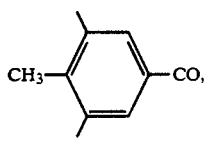

J=8 Hz) 6.78 (1H, dd, $C_5$—H of the pyridine ring, $J_{3,5}$=2 Hz, $J_{5,6}$=6 Hz) 6.62 (1H, d, $C_3$—H of the pyridine ring, J=2.0 Hz) 2.43 (3H, s, $CH_3$—)

Example 29

Preparation of 4-hydroxy-2-(2-methylpropanoyloxy)-pyridine

To 2.0 g of 2,4-bis(trimethylsilyloxy)-pyridine in 20 ml of methylene chloride was added 1.01 g of 2-methylpropionyl chloride and the mixture was stirred at room temperature for one hour. Following thereafter the general procedure of Example 27, 230 mg of the title compound was obtained in a yield of 16.1%.

NMR(DMSO-$d_6$)$\delta$: 7.37 (1H, d, $C_6$—H of the pyridine ring, J=7 Hz) 6.34 (1H, d, $C_3$—H of the pyridine ring, J=2 Hz) 6.17 (1H, dd, $C_5$—H of the pyridine ring, $J_{3,5}$=2 Hz, $J_{5,6}$=7 Hz) 2.96–2.56 (1H, m, $(CH_3)_2CH$—) 1.29 (6H, d, $CH_3$—$\times$2, J=7 Hz)

Example 30

Preparation of 4-hydroxy-2-(2-methylbenzoyloxy)-pyridine

The general procedure of Example 27 was followed using 4.0 g of 2,4-bis(trimethylsilyloxy)-pyridine and 2.92 g of 2-methylbenzoyl chloride, thereby producing 1.59 g of the title compound in a yield of 44.18%.

M.p. 116°–119° C.

Example 31

Preparation of 2,4-di-n-pentanoyloxypyridine

The general procedure of Example 27 was repeated using 1.00 g of 2,4-bis(trimethylsilyloxy)-pyridine, 50 ml of dichloromethane, 1.02 ml of pentanoyl chloride and 0.10 ml of stannic chloride, thereby producing 200 mg of the title compound in a yield of 18%.

NMR(CDCl$_3$)$\delta$: 8.35 (1H, d, $C_6$—H of the pyridine ring, J=6 Hz) 7.05 (1H, dd, $C_5$—H of the pyridine ring, $J_{3,5}$=6 Hz, $J_{5,6}$=2 Hz) 6.95 (1H, d, $C_3$—H of the pyridine ring, J=2.0 Hz) 2.67–2.48 (4H, m, CO—$CH_2$—$\times$2) 1.83–1.02 (8H, m, $CH_2\times4$) 0.87 (6H, t, $CH_3\times2$, J=7 Hz)

Example 32

Preparation of 5-chloro-2,4-dibenzoyloxypyridine

A 1.76 ml quantity of benzoyl chloride was added to a suspension of 1.00 g of 5-chloro-4-hydroxy-2-pyridone in 30 ml of pyridine, and the mixture was stirred at room temperature for two hours. The solvent was distilled off and the residue was dissolved in a mixture solution of 60 ml of ethyl acetate and 30 ml of water. The ethyl acetate layer was separated, washed twice with 30 ml of water, dried on anhydrous sodium sulfate and concentrated. The concentrate was further washed with a small amount of ethanol, giving 2.11 g of the title compound in a yield of 86.8%.

M.p. 124°–125° C.

Example 33

Preparation of 2,4-dibenzoyloxypyridine

To 4.0 g of 2,4-bis(trimethylsilyloxy)-pyridine in 50 ml of dichloromethane were added 2.65 g of benzoyl chloride and 0.2 ml of stannic chloride, and the mixture was stirred at room temperature for one hour. The solvent was distilled off and the residue was subjected to silica gel chromatography using ethyl acetate-benzene (2:3) as an eluent to produce 0.74 g of the title compound in a yield of 14.8%.

M.p. 100°–102° C.

Example 34

Preparation of 5-chloro-4-(2-thenoyloxy)-2-pyridone

A 2.42 g quantity of 2-thenoyl chloride was added to a suspension of 2.00 g of 5-chloro-4-hydroxy-2-pyridone in 100 ml of pyridine, and the mixture was stirred at room temperature for 4.5 hours. The reaction mixture was concentrated and the concentrate was washed with ethyl acetate and water, thereby producing 0.82 g of the title compound in a yield of 23%.

NMR(DMSO-$d_6$)$\delta$: 8.19–8.04 (2H, m, $C_{3,5}$—H of the thiophene ring) 7.88 (1H, s, $C_6$—H of the pyridine ring) 7.38–7.28 (1H, m, $C_4$—H of the thiophene ring) 6.56 (1H, s, $C_3$—H of the pyridine ring)

Example 35

Preparation of 4-phenoxyacetyloxy-2-pyridone

A 1.86 ml quantity of phenoxyacetyl chloride was added to a suspension of 1.00 g of 4-hydroxy-2-pyridone in 30 ml of pyridine, and the mixture was stirred at room temperature for four hours. The reaction mixture was concentrated and the concentrate was washed with ethyl acetate, water and chloroform in this order, thereby producing 500 mg of the title compound in a yield of 23%.

NMR(DMSO-d$_6$)δ: 11.51 (1H, bs, N-H, disappeared by addition of D$_2$O) 7.51-6.91 (6H, m, C$_6$—H of the pyridine ring and phenyl-H) 6.16-6.07 (2H, m, C$_{3,5}$—H of the pyridine ring) 5.05 (2H, s, CH$_2$)

Example 36

Preparation of 1-ethylcarbamoyl-4-hydroxy-2-pyridone

A 2.50 ml quantity of ethyl isocyanate was added to a suspension of 3.00 g of 4-hydroxy-2-pyridone in 20 ml of pyridine, and the mixture was stirred at room temperature for one hour. The solvent was distilled off and the residue was dissolved in 50 ml of ethyl acetate. The solution was washed twice with 30 ml of water. The ethyl acetate layer was dried on anhydrous sodium sulfate and concentrated. The concentrate was recrystallized from ethanol-ether, thereby producing 1.48 g of the title compound in a yield of 30.1%.

M.p. 272° C. (foaming)

NMR(DMSO-d$_6$)δ: 11.05 (1H, bs, OH) 10.52 (1H, t, J=5 Hz, —CONH—) 8.25 (1H, d, J=8 Hz, C$_6$—H of the pyridine ring) 6.15 (1H, dd, J$_{3,5}$=3 Hz, J$_{5,6}$=8 Hz, C$_5$—H of the pyridine ring) 5.73 (1H, d, J=3 Hz, C$_3$—H of the pyridine ring) 3.50-3.20 (2H, m, —CH$_2$CH$_3$) 1.16 (3H, t, J=7 Hz, —CH$_2$CH$_3$)

Example 37

Preparation of 1-methylcarbamoyl-4-hydroxy-2-pyridone

A 0.64 ml quantity of methyl isocyanate was added to a suspension of 1.00 g of 4-hydroxy-2-pyridone in 20 ml of pyridine and the mixture was stirred at room temperature for one hour. Thereafter the general procedure of Example 36 was followed to produce the title compound in a yield of 30%.

M.p. 268° C. (foaming)

NMR(DMSO-d$_6$)δ: 11.27 (1H, bs, OH) 10.36 (1H, bs, —CONH—) 8.23 (1H, d, J=8 Hz, C$_6$—H of the pyridine ring) 6.13 (1H, dd, J$_{3,5}$=2 Hz, J$_{5,6}$=8 Hz, C$_5$—H of the pyridine ring) 5.71 (1H, d, J=2 Hz, C$_3$—H of the pyridine ring) 2.88 (3H, d, J=5 Hz, CH$_3$)

Example 38

Preparation of 4-(4-n-propoxybenzoyloxy)-2-pyridone

A 2.14 g quantity of 4-n-propoxybenzoyl chloride was added to a suspension of 1.00 g of 4-hydroxy-2-pyridone in 30 ml of pyridine, and the mixture was stirred at room temperature for 4 hours. The reaction mixture was concentrated and the concentrate was washed with ethyl acetate and water, thereby producing 1.98 g of the title compound in a yield of 81%.

NMR(DMSO-d$_6$)δ: 8.03 (2H, d, J=9 Hz,

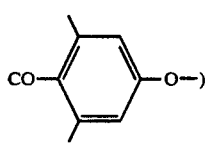

7.47 (1H, d, J=8 Hz, C$_6$—H of the pyridine ring) 7.23 (2H, d, J=9 Hz,

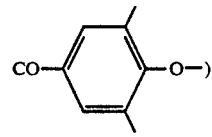

6.24-6.17 (2H, m, C$_{3,5}$—H of the pyridine ring) 4.05 (2H, t, J=7 Hz, O—CH$_2$) 1.88-1.65 (2H, m, CH$_2$—CH$_3$) 0.99 (3H, t, J=7 Hz, CH$_3$)

Example 39

Preparation of 5-chloro-4-nicotinoyloxy-2-pyridone

A 2.93 g quantity of nicotinoyl chloride hydrochloride was added to a suspension of 2.00 g of 5-chloro-4-hydroxy-2-pyridone in 100 ml of pyridine, and the mixture was stirred at room temperature for 9 hours. The reaction mixture was concentrated and the concentrate was washed with ethyl acetate and water, thereby producing 1.77 g of the title compound in a yield of 51%.

NMR(DMSO-d$_6$)δ: 9.26 (1H, d, C$_2$—H of the pyridine ring, J=2 Hz) 8.94 (1H, dd, J$_{4,6}$=2 Hz, J$_{5,6}$=5 Hz, C$_6$—H of the nicotinoyl ring) 8.47 (1H, td, J$_{2,4}$=2 Hz, J$_{4,5}$=8 Hz, C$_5$—H of the nicotinoyl ring) 7.90 (1H, s, C$_6$—H of the pyridine ring) 7.75-7.61 (1H, m, C$_5$—H of the nicotinoyl ring) 6.61 (1H, s, C$_3$—H of the pyridine ring)

Example 40

Preparation of 5-chloro-4-phenylacetyloxy-2-pyridone

A 3.63 ml quantity of phenylacetyl chloride was added to a suspension of 2.00 g of 5-chloro-4-hydroxy-2-pyridone in 60 ml of pyridine. The same subsequent procedure as in Example 39 was conducted, thereby producing 500 mg of the title compound in a yield of 14%.

NMR(DMSO-d$_6$)δ: 7.81 (1H, s, C$_6$—H of the pyridine ring) 7.35 (5H, s, phenyl-H) 6.36 (1H, s, C$_3$—H of the pyridine ring) 4.02 (1H, s, —CH$_2$—)

Example 41

Preparation of 5-chloro-4-(2-furoyloxy)-2-pyridone

A 2.15 g quantity of 2-furoyl chloride was added to a suspension of 2.00 g of 5-chloro-4-hydroxy-2-pyridone in 100 ml of pyridine. The same subsequent procedure as in Example 39 was conducted, thereby producing 1.13 g of the title compound in a yield of 34%.

NMR(DMSO-d$_6$)δ: 8.15 (1H, d, J=2 Hz, C$_5$—H of the furan ring) 7.88 (1H, s, C$_6$—H of the pyridine ring) 7.64 (1H, d, J=4 Hz, C$_3$—H of the furan ring) 6.82 (1H, dd, J$_{4,5}$=2 Hz, J$_{3,4}$=4 Hz, C$_4$—H of the furan ring) 6.54 (1H, s, C$_3$—H of the pyridine ring)

Example 42

Preparation of 5-chloro-4-(3,4,5-trimethoxybenzoyl-oxy)-2-pyridone

A 3.80 g quantity of 3,4,5-trimethoxybenzoyl chloride was added to a suspension of 2.00 g of 5-chloro-4-hydroxy-2-pyridone in 100 ml of pyridine, and the mixture was stirred at room temperature for 2.5 hours. The reaction mixture was concentrated and the concentrate was washed with ethyl acetate and water, thereby producing 1.60 g of the title compound in a yield of 34%.

NMR(CDCl$_3$)δ: 7.88 (1H, s, C$_6$—H of the pyridine ring) 7.39 (2H, s, phenyl-H) 6.82 (1H, s, C$_3$—H of the pyridine ring) 3.87 (6H, s, —OCH$_3$×2) 3.80 (3H, s, —OCH$_3$)

Example 43

Preparation of 2-benzoyloxy-5-chloro-4-nicotinoyloxypyridine

A 300 ml quantity of 5-chloro-4-nicotinoyloxy-2-pyridone was suspended in a mixture solvent of 30 ml of dioxane and 10 ml of pyridine and to the suspension were added 0.17 ml of benzoyl chloride and 0.83 ml of triethylamine. The mixture was refluxed for 3 hours. The resulting reaction mixture was concentrated and the concentrate was subjected to silica gel column chromatography using as an eluent, chloroform, thereby producing 230 mg of the title compound in a yield of 54%.

NMR(CDCl$_3$)δ: 9.41–8.37 (3H, m, C$_{2,4,6}$—H of the nicotinoyl ring) 8.51 (1H, s, C$_6$—H of the pyridine ring) 8.24–8.14 (2H, m,

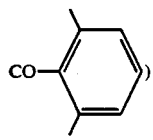

7.64–7.31 (4H, m, C$_5$—H of the pyridine ring and

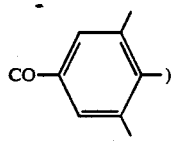

7.44 (1H, s, C$_3$—H of the pyridine ring)

Example 44

Preparation of 2,4-diacetoxy-5-chloropyridine

A 1.00 g quantity of 5-chloro-4-hydroxy-2-pyridone was suspended in 40 ml of pyridine. To the suspension was slowly added 3.38 g of acetyl bromide with stirring at room temperature and then the mixture was stirred at 70° C. for 1 hour. The precipitate formed was filtered off and the filtrate was concentrated. The concentrate was washed with ether and then with acetone. The ether and acetone layers were combined and concentrated, and the concentrate was subjected to silica gel column chromatography using an eluent chloroform, thereby producing 1.52 g of the title compound in a yield of 96.4%.

NMR(CDCl$_3$)δ: 8.41 (1H, s, C$_6$—H of the pyridine ring) 7.06 (1H, s, C$_3$—H of the pyridine ring) 2.36 and 2.32 (each 3H, s, CH$_3$)

Example 45

Preparation of 5-chloro-4-piperonyloyloxy-2-pyridone

A 3.80 g quantity of piperonyloyl chloride was added to a suspension of 2.00 g of 5-chloro-4-hydroxy-2-pyridone in 60 ml of pyridine, and the mixture was stirred at room temperature for 2.5 hours. The reaction mixture was filtered and the filtrate was concentrated. The concentrate was washed successively with ethyl acetate, water and chloroform and then purified by silica gel column chromatography using as an eluent 2% methanol-chloroform, thereby producing 200 mg of the title compound in a yield of 5%.

NMR(DMSO-d$_6$)δ: 12.01 (1H, bs, N—H) 7.86 (1H, s, C$_6$—H of the pyridine ring) 7.78 (1H, dd, J$_{2,6}$=2 Hz, J$_{5,6}$=8 Hz,

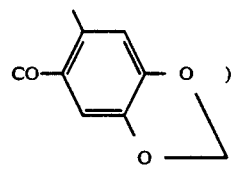

7.52 (1H, d, J=1 Hz,

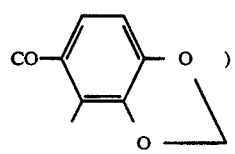

7.11 (1H, d, J=8 Hz,

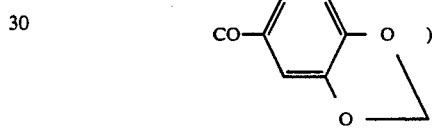

6.51 (1H, s, C$_3$—H of the pyridine ring) 6.20 (2H, s, CH$_2$)

Example 46

Preparation of 5-chloro-2,4-dipiperonyloyloxypyridine

The general procedure of Example 45 was followed using 2.00 g of 5-chloro-4-hydroxy-2-pyridone and 3.80 g of piperonyloyl chloride, thereby producing 180 mg of the title compound in a yield of 3%.

NMR(DMSO-d$_6$)δ: 8.68 (1H, s, C$_6$—H of the pyridine ring) 7.86–7.72 (2H, m,

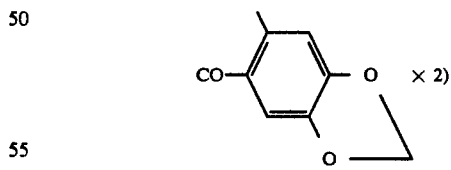

7.68 (1H, s, C$_3$—H of the pyridine ring) 7.59–7.54 (2H, m,

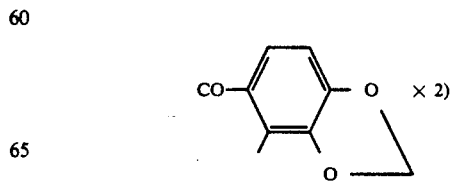

7.20–7.08 (2H, m,

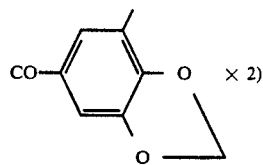

6.21 and 6.20 (each 2H, s, —CH$_2$—)

Example 47

Preparation of 4-(3-benzyloxycarbonylbenzoyloxy)-5-chloro-2-pyridone

The general procedure of Example 1 was followed using 2.20 g of 5-chloro-4-hydroxy-2-pyridone and 5.31 g of 3-benzyloxycarbonylbenzoyl chloride, thereby giving 1.73 g of the title compound in a yield of 29%.

NMR(DMSO-d$_6$)δ: 12.22 (1H, bs, N—H) 8.65–7.80 (4H, m,

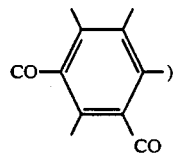

7.89 (1H, s, C$_6$—H of the pyridine ring) 7.52–7.34 (5H, m,

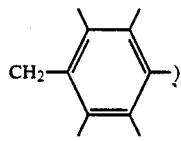

6.60 (1H, s, C$_3$—H of the pyridine ring) 5.42 (2H, s, —CH$_2$—)

Example 48

Preparation of 4-(n-pentanoyloxy)-2-pyridone

The general procedure of Example 31 was followed using 1.00 g of 2,4-bis(trimethylsilyloxy)-pyridine and 1.02 ml of n-pentanoyl chloride, thereby giving 310 mg of the title compound in a yield of 41%.

NMR(DMSO-d$_6$)δ: 11.62 (1H, bs, N—H) 7.42 (1H, d, J=8 Hz, C$_6$—H of the pyridine ring) 6.11–6.00 (2H, m, C$_{3,5}$—H of the pyridine ring) 2.55 (2H, t, J=7 Hz, CO—CH$_2$—) 1.69–1.23 (4H, m, CH$_2$×2) 0.90 (3H, t, J=7 Hz, CH$_3$)

Example 49

Preparation of 2-acetoxy-4-benzoyloxy-5-chloropyridine

The general procedure of Example 21 was followed using 200 mg of 2-acetoxy-5-chloro-4-hydroxypyridine, 0.15 ml of benzoyl chloride and 0.74 ml of triethylamine and 20 ml of acetonitrile, thereby giving 300 mg of the title compound in a yield of 96%.

NMR(CDCl$_3$)δ: 8.43 (1H, s, C$_6$—H of the pyridine ring) 8.23–7.48 (5H, m, phenyl-H) 7.27 (1H, s, C$_3$—H of the pyridine ring) 2.29 (3H, s, CH$_3$)

Example 50

Preparation of 4-benzoyloxy-5-chloro-1-ethoxymethyl-2-pyridone

The general procedure of Example 49 was followed using 200 mg of 5-chloro-1-ethoxymethyl-4-hydroxy-2-pyridone, 0.14 ml of benzoyl chloride, 0.68 ml of triethylamine and 20 ml of dioxane, thereby producing 280 mg of the title compound in a yield of 93%.

NMR(CDCl$_3$)δ: 8.21–7.42 (5H, m, phenyl-H) 7.58 (1H, s, C$_6$—H of the pyridine ring) 6.61 (1H, s, C$_3$—H of the pyridine ring) 5.35 (2H, s, N—CH$_2$) 3.65 (2H, q, J=5 Hz, CH$_2$—CH$_3$) 1.23 (3H, t, J=5 Hz, CH$_2$—CH$_3$)

Example 51

Preparation of 1-allyl-5-chloro-4-hydroxy-2-pyridone

The general procedure of Example 50 was followed using 878 mg of 2,4-bis(trimethylsilyloxy)chloropyridine, 0.35 ml of allyl bromide, 0.10 ml of stannic chloride and 15 ml of acetonitrile, thereby producing 60 mg of the title compound in a yield of 9%.

NMR(DMSO-d$_6$)δ: 7.80 (1H, s, C$_6$—H of the pyridine ring) 6.11–5.69 (1H, m, —CH=) 5.81 (1H, s, C$_3$—H of the pyridine ring) 5.30–4.94 (1H, m, =CH$_2$) 4.60–4.36 (1H, m, N—CH$_2$)

Example 52

Preparation of 2,4-di(3-chlorobenzoyloxy)pyridine

A 1.00 g quantity of 4-hydroxy-2-pyridone was suspended in 30 ml of pyridine and 3.46 g of 3-chlorobenzoyl chloride was added to the suspension. The mixture was stirred at room temperature for 2 days. The reaction mixture was filtered and the filtrate was concentrated and the concentrate was extracted with ethyl acetate. The extract was concentrated and the concentrate was washed with water and with methanol, giving 1.74 g of the title compound in a yield of 50%.

NMR(CDCl$_3$)δ: 8.56 (1H, d, J=6 Hz, C$_6$—H of the pyridine ring) 8.16–7.66 (8H, m,

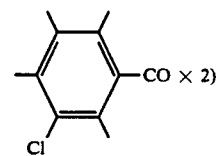

7.57–7.52 (2H, m, C$_{3,5}$—H of the pyridine ring)

Example 53

Preparation of 2,4-di(2-methoxybenzoyloxy)pyridine

A 2.00 g quantity of 4-hydroxy-2-pyridone was suspended in 60 ml of pyridine, and 5.52 g of 2-anisoyl chloride was added to the suspension. The mixture was stirred at room temperature for 1 day. The reaction mixture was concentrated and the concentrate was washed with benzene and extracted with ethyl acetate. The extract was concentrated and the concentrate was subjected to a silica gel column chromatography using chloroform-acetone (30:1) as an eluent, giving 120 mg of the title compound in a yield of 2%.

NMR(CDCl$_3$)δ: 8.45 (1H, d, J=6 Hz, C$_6$—H of the pyridine ring) 8.14–6.96 (8H, m,

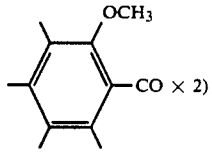

7.27–7.21 (2H, m, C$_{3,5}$—H of the pyridine ring) 3.93 (6H, s, —OCH$_3$×2)

Example 54

Preparation of 1-carboxylmethylcarbamoyl-4-hydroxy-2-pyridone

A 5.40 ml quantity of 1N aqueous solution of sodium hydroxide was added to a solution of 600 mg of 4-hydroxy-1-methoxycarbonylmethylcarbamoyl-2-pyridone in 10 ml of methanol, and the mixture was stirred at room temperature for 1 hour. Then the reaction solution was made weakly acidic with 1N hydrochloric acid. The precipitate thus formed was filtered and dried, producing 410 mg of the title compound in a yield of 71.9%.

NMR(DMSO-d$_6$)δ: 10.82 (1H, t, CO—NH—CH$_2$—, J=5 Hz, disappeared by addition of D$_2$O) 8.10 (1H, d, C$_6$—H of the pyridine ring, J=8 Hz) 6.02 (1H, dd, C$_5$—H of the pyridine ring, J=2 Hz, J=8 Hz) 5.50 (1H, d, C$_3$—H of the pyridine ring, J=2 Hz) (2H, d, —NH—CH$_2$—COOH, J=5 Hz)

Example 55

Preparation of 4-(3-benzyloxycarbonylpropoxy)-1-ethoxymethyl-2-pyridone

A 0.22 g quantity of 1-ethoxymethyl-4-hydroxy-2-pyridone and 0.43 g of monobenzyl ester of succinic acid were dissolved in 5 ml of tetrahydrofuran, and 0.45 g of dicyclohexylcarbodiimide was added to the solution with ice cooling. The mixture was reacted overnight at room temperature and the precipitates were filtered off. The filtrate was concentrated and purified on a silica gel chromatography using chloroform as an eluent, giving 0.41 g of the title compound in a yield of 88%.

NMR(CDCl$_3$)δ: 7.34 (6H, bs, phenyl-H, C$_6$—H of the pyridine ring) 6.30 (1H, d, C$_3$—H of the pyridine ring, J=2 Hz) 6.06 (1H, dd, C$_5$—H of the pyridine ring, J=7 Hz, 2 Hz) 5.33 (2H, s, —CH$_2$N) 5.15 (2H, s, —CH$_2$OCO) 3.60 (2H, q, CH$_2$CH$_3$, J=7 Hz) 2.68–2.82 (4H, m, CH$_2$CH$_2$) 1.20 (3H, t, CH$_3$, J=7 Hz)

Example 56

Preparation of 5-chloro-2,4-dibenzoyloxypyridine and 4-benzoyloxy-5-chloro-2-pyridone A 0.50 g quantity of 5-chloro-4-hydroxy-2-pyridone was dissolved in 15 ml of N,N-dimethylformamide, and 0.45 g of sodium hydride was added to the solution. The mixture was stirred at room temperature for 2 hours. Then a solution of 1.10 g of benzoyl chloride in 5 ml of N,N-dimethylformamide was added dropwise and reacted for 1 hour. After the reaction, the solvent was distilled off, then the residue was extracted with chloroform, and the extract was concentrated. The concentrate was subjected to a silica gel column chromatography, giving as the first eluate 0.80 g of the desired dibenzoyloxy derivative in a yield of 66% and as the second eluate 0.04 g of the desired 4-benzoyloxy derivative in a yield of 5%.

The dibenzoyloxy derivative (5-chloro-2,4-dibenzoyloxypyridine) M.p. 124°–125° C.

The 4-benzoyloxy derivative (4-benzoyloxy-5-chloro-2-pyridone) M.p. 196°–197° C.

Example 57

Preparation of 5-chloro-2-ethoxycarbonyloxy-4-hydroxypyridine

A 2.00 g quantity of 5-chloro-4-hydroxy-2-pyridone was refluxed in 1,1,1,3,3,3-hexamethyldisilazane overnight. The solution was cooled by standing and the excess disilazane was distilled off. The ammonia present in the residue was removed by a vacuum pump. The residue was diluted with 20 ml of acetonitrile. To the dilution was added 20 ml of a solution of 3.00 g of ethyl chloroformate in acetonitrile. To the mixture was added dropwise 0.10 ml of stannic chloride and the resulting mixture was refluxed for 5 hours. The reaction mixture was concentrated, the concentrate was dissolved in ethyl acetate and the solution was treated with methanol. The unreacted starting material (5-chloro-4-hydroxy-2-pyridone) thus precipitated was separated by filtration. The ethyl acetate layer was concentrated and the concentrate was subjected to silica gel column chromatography using as an eluent 1% methanol-chloroform, giving 0.68 g of the title compound in a yield of 23%.

NMR(DMSO-d$_6$)δ: 12.0 (1H, broad, OH) 8.21 (1H, s, C$_6$—H of the pyridine ring) 6.78 (1H, s, C$_3$—H of the pyridine ring) 4.26 (2H, q, CH$_2$CH$_3$, J=7 Hz) 1.29 (3H, t, CH$_2$CH$_3$, J=7 Hz)

Example 58

Preparation of 5-chloro-4-ethoxycarbonyloxy-2-pyridone

A 2.00 g quantity of 5-chloro-4-hydroxy-2-pyridone was refluxed in 30 ml of 1,1,1,3,3,3-hexamethyldisilazane overnight. The solution was cooled by standing and the excess disilazane was distilled off. The presence of ammonia resulting as a by-product from the reaction was confirmed at that time. To the solution was added 15 ml of methylene chloride and thereto was further added 10 ml of a solution of 2.20 g of ethyl chloroformate in methylene chloride. The mixture was subjected to reaction at room temperature for 4 hours. The same subsequent procedure as in Example 57 was repeated, collecting the unreacted materials and affording 0.18 g of the title compound in a yield of 6%.

NMR(DMSO-d$_6$)δ: 11.96 (1H, s, NH) 7.84 (1H, s, C$_6$—H of the pyridine ring) 6.49 (1H, s, C$_3$—H of the pyridine ring) 4.29 (2H, q, CH$_2$CH$_3$, J=7 Hz) 1.30 (3H, t, CH$_2$CH$_3$, J=7 Hz)

Example 59

Preparation of 4-acetoxy-5-chloro-5-pyridone

There were mixed 3.00 g of 5-chloro-2,4-bis-(trimethylsilyloxy)pyridine, 3.0 ml of triethylamine and 50 ml of acetonitrile. To the mixture was added dropwise 1.00 ml of acetyl bromide, and the resulting mixture was subjected to reaction at room temperature for 1 hour. After completion of the reaction, the mixture was concentrated and the concentrate was recrystallized from acetone, giving 0.66 g of the title compound in a yield of 34%.

Example 60

Preparation of 5-chloro-4-lauroyloxy-2-pyridone and 5-chloro-2,4-di(lauroyloxy)pyridine A 2.00 g quantity of 5-chloro-4-hydroxy-2-pyridone was suspended in 100 ml of pyridine. To the suspension was added dropwise 4.50 g of lauroyl chloride and the mixture was stirred at room temperature for 6 hours. After completion of the reaction, the pyridine was distilled off and the residue was stirred in ether overnight. The precipitate thus obtained was separated by filtration and dried, affording 1.20 g of the desired monoacyl product. The ether layer was concentrated and the concentrate was applied to silica gel column chromatography using chloroform as an eluent, giving 0.38 g of monoacyl product (total yield of 35%) and 2.14 g of diacyl product (yield of 31%). Monoacyl product (5-chloro-4-lauroyloxy-2-pyridone)

NMR(DMSO-$d_6$)$\delta$: 7.81 (1H, s, $C_6$—H of the pyridine ring) 6.33 (1H, s, $C_3$—H of the pyridine ring) 2.61 (2H, t, $CH_2CO$, J=7 Hz) 1.25 (18H, m, $CH_2 \times 9$) 0.85 (3H, t, $CH_3$, J=7 Hz) Diacyl product (5-chloro-2,4-di(lauroyloxy)pyridine)

NMR(CDCl$_3$)$\delta$: 8.39 (1H, s, $C_6$—H of the pyridine ring) 7.04 (1H, s, $C_3$—H of the pyridine ring) 2.52–2.72 (4H, m, $CH_2CO \times 2$) 1.27 (36H, bs, $CH_2 \times 18$) 0.88 (6H, t, $CH_3 \times 2$)

Example 61

Preparation of 5-chloro-4-hydroxy-1-methylthiomethyl-2-pyridone

A 0.50 g quantity of 5-chloro-4-hydroxy-2-pyridone was refluxed in 10 ml of 1,1,1,3,3,3-hexamethyldisilazane overnight. The excess hexamethyldisilazane was distilled off and the residue was dissolved in 15 ml of acetonitrile. To the solution was added 0.70 g of chloromethyl methyl sulfide and the mixture was stirred at room temperature for 6 hours. The mixture was neutralized with triethylamine and the solvent was distilled off. The residue was subjected to silica gel column chromatography using 2% methanol-chloroform as an eluent, giving 0.01 g of the title compound in a yield of 2%.

NMR(DMSO-$d_6$)$\delta$: 7.94 (1H, s, $C_6$—H of the pyridine ring) 5.77 (1H, s, $C_3$—H of the pyridine ring, disappeared by addition of $D_2O$) 4.92 (2H, s, $CH_2S$) 2.12 (3H, s, $CH_3$)

Example 62

Preparation of 5-chloro-4-(4-chlorobenzoyloxy)-2-pyridone and 5-chloro-2,4-di(4-chlorobenzoyloxy)-pyridine The general procedure of Example 60 was followed using 2.00 g of 5-chloro-4-hydroxy-2-pyridone, 3.60 g of 4-chlorobenzoyl chloride and 100 ml of pyridine and conducting the reaction overnight, thereby producing 1.11 g of desired monoacyl product (yield 29%) and 2.70 g of desired diacyl product (yield 47%). Monoacyl product (5-chloro-4-(4-chloro-benzoyl)oxy-2-pyridone)

NMR(DMSO-$d_6$)$\delta$: 12.01 (1H, bs, NH) 8.12 (2H, d,

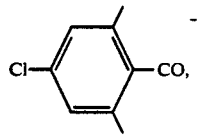

J=8 Hz) 7.89 (1H, s, $C_6$—H of the pyridine ring) 7.70 (2H, d,

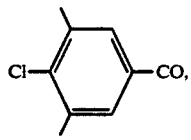

J=8 Hz) 6.57 (1H, s, $C_3$—H of the pyridine ring) Diacyl product (5-chloro-2,4-di(4-chlorobenzoyl)-oxypyridine)

NMR(CDCl$_3$)$\delta$: 8.51 (1H, s, $C_6$—H of the pyridine ring) 8.15 (4H, d,

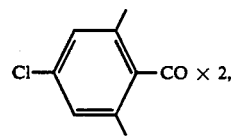

J=8 Hz) 7.39–7.57 (5H, m, $C_3$—H of the pyridine ring and

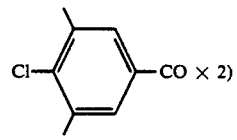

Example 63

Preparation of 5-chloro-4-(4-methoxybenzoyloxy)-2-pyridone and 5-chloro-2,4-di(4-methoxybenzoyloxy)-pyridine A 2.00 g quantity of 5-chloro-4-hydroxy-2-pyridone was suspended in 150 ml of pyridine. To the solution was added dropwise 2.80 g of 4-methoxybenzoyl chloride. The mixture was reacted at room temperature for 4 hours. After completion of the reaction, the pyridine was distilled off and the residue was applied to silica gel column chromatography using as an eluent petroleum ether-chloroform (1:4) to give 2.74 g of the desired dibenzoyl product in a yield of 48% and employing as an eluent chloroform to afford 1.27 g of monobenzoyl product in a yield of 33%. Monobenzoyl product (5-chloro-4-(4-methoxybenzoyloxy)-2-pyridone)

NMR(DMSO-$d_6$)$\delta$: 11.95 (1H, s, NH) 8.07 (2H, d,

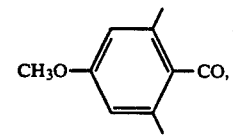

J=9 Hz) 7.86 (1H, s, C₆—H of the pyridine ring) 7.14 (2H, d,

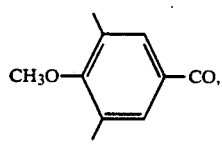

J=9 Hz) 6.51 (1H, s, C₃—H of the pyridine ring) 3.88 (3H, s, CH₃O) Dibenzoyl product (5-chloro-2,4-di(4-methoxybenzoyloxy)pyridine)

NMR(CDCl₃)δ: 8.49 (1H, s, C₆—H of the pyridine ring) 8.17 (2H, d,

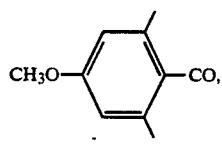

J=9 Hz) 8.16 (2H, d,

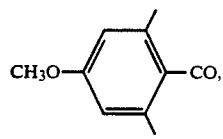

J=9 Hz) 7.37 (1H, s, C₃—H of the pyridine ring) 7.01 (2H, d,

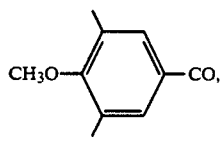

J=9 Hz) 6.98 (2H, d,

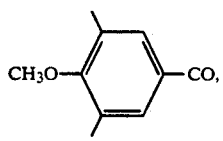

J=9 Hz) 3.91 (3H, s, CH₃O) 3.89 (3H, s, CH₃O)

Example 64

Preparation of
5-chloro-4-(4-dimethylaminobenzoyloxy)-2-pyridone
and
5-chloro-2,4-di(4-dimethylaminobenzoyl-oxy)pyridine There were mixed 2.70 g of 4-dimethylaminobenzoic acid, 2.0 ml of thionyl chloride and 50 ml of benzene. The mixture was refluxed overnight and left to stand for cooling. Then the benzene was distilled off and the residue was diluted with 70 ml of pyridine. The dilution was added to 80 ml of a solution of 2.00 g of 5-chloro-4-hydroxy-2-pyridone in pyridine. The mixture was subjected to reaction at room temperature for 3 hours. The pyridine was distilled off and the residue was applied to silica gel column chromatography using chloroform as an eluent to give 1.34 g of the desired diacyl product (yield 24%) and employing 2% methanol-chloroform as an eluent to afford 1.89 g of monoacyl product (yield 47%). Monoacyl (5-chloro-4-(4-dimethylaminobenzoyloxy)-2-pyridone)

NMR(DMSO-d₆)δ: 11.88 (1H, bs, —NH—) 7.91 (2H, d,

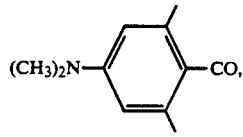

J=9 Hz) 7.80 (1H, s, C₆—H of the pyridine ring) 6.81 (2H, d,

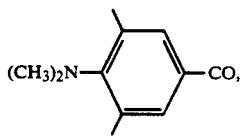

J=9 Hz) 6.45 (1H, s, C₃—H of the pyridine ring) 3.05 (6H, s, CH₃×2) Diacyl product (5-chloro-2,4-di(4-dimethylaminobenzoyloxy)pyridine)

NMR(CDCl₃)δ: 8.45 (1H, s, C₆—H of the pyridine ring) 8.05 (4H, d,

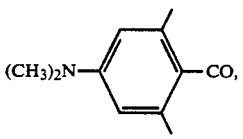

J=9 Hz) 7.36 (1H, s, C₃—H of the pyridine ring) 6.69 (2H, d,

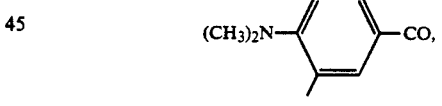

J=9 Hz) 6.67 (2H, d,

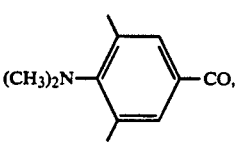

J=9 Hz) 3.08 (6H, s, CH₃) 3.07 (6H, s, CH₃)

Example 65

Preparation of
5-chloro-2,4-di(4-methylbenzoyloxy)-pyridine

A 2.66 g quantity of 4-methylbenzoyl chloride was added dropwise to 50 ml of a solution of 1.00 g of 5-chloro-4-hydroxy-2-pyridone in pyridine. The mixture was subjected to reaction at room temperature overnight. The pyridine was distilled off and the residue was stirred in ether for 6 hours. The solids thus precipitated were dried, giving 1.71 g of the title compound. The ether was concentrated and the residue was applied to silica gel column chromatography using as an eluent petroleum ether-chloroform (1:2), affording 0.85 g of the same compound (total amount 2.56 g, total yield 97%).

NMR(DMSO-d$_6$)δ: 8.71 (1H, s, C$_6$—H of the pyridine ring) 8.07 (2H, d,

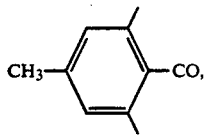

J=8 Hz) 8.04 (2H, d,

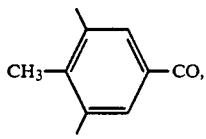

J=8 Hz) 7.73 (1H, s, C$_3$—H of the pyridine ring) 7.46 (2H, d,

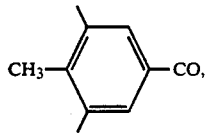

J=8 Hz) 7.45 (2H, d,

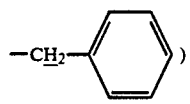

J=8 Hz) 3.29 (6H, s, CH$_3$×2)

Example 66

Preparation of 4-(4-benzyloxybenzoyloxy)-5-chloro-2-pyridone

A 3.00 g quantity of 5-chloro-4-hydroxy-2-pyridone was suspended in 100 ml of pyridine. To the suspension was added 5.59 g of 4-benzyloxybenzoyl chloride with stirring at room temperature. The reaction mixture was stirred at 90° C. for 1.5 hours. The solvent was distilled off and ethyl acetate was added to the residue. The mixture was stirred at room temperature overnight. The ethyl acetate layer was concentrated and the residue was subjected to silica gel column chromatography using as an eluent 2% methanol-chloroform, giving 770 mg of the title compound in a yield of 10.5%.

NMR(CDCl$_3$)δ: 8.14 (2H, d,

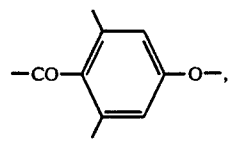

J=9 Hz) 7.52 (1H, s, C$_6$—H of the pyridine ring) 7.40 (5H, s, phenyl-H) 7.07 (2H, d,

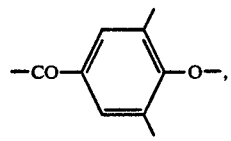

J=9 Hz) 6.64 (1H, s, C$_3$—H of the pyridine ring) 5.17 (2H, s,

—CH$_2$—⟨phenyl⟩)

Example 67

Preparation of 5-chloro-4-hydroxy-1-methoxymethyl-2-pyridone

The general procedure of Example 61 was followed using 1.75 g of 2,4-bis(trimethylsilyloxy)-5-chloropyridine, 0.66 g of chloromethyl methyl ether and 20 ml of acetonitrile, thereby producing 0.63 g of the title compound in a yield of 49%.

NMR(DMSO-d$_6$)δ: 11.55 (1H, bs, OH) 7.87 (1H, s, C$_6$—H of the pyridine ring) 5.76 (1H, s, C$_3$—H of the pyridine ring) 5.12 (2H, s, NCH$_2$) 3.24 (3H, s, OCH$_3$)

Example 68

Preparation of 5-chloro-4-(1-naphthoyloxy)-2-pyridone

The general procedure of Example 45 was followed using 2.00 g 5-chloro-4-hydroxy-2-pyridone, 3.93 g of α-naphthoyl chloride and 100 ml of pyridine, thereby producing 1.15 g of the title compound in a yield of 28%.

NMR(DMSO-d$_6$)δ: 12.07 (1H, bs, NH) 8.89–7.64 (7H, m, naphthyl-H) 7.94 (1H, s, C$_6$—H of the pyridine ring) 6.68 (1H, s, C$_3$—H of the pyridine ring)

Example 69

Preparation of 5-chloro-2,4-di(1-naphthoyloxy)-pyridine

The general procedure of Example 45 was followed using 2.00 g of 5-chloro-4-hydroxy-2-pyridone, 3.93 g of α-naphthoyl chloride and 100 ml of pyridine, thereby producing 3.83 g of the title compound in a yield of 61%.

NMR(DMSO-d$_6$)δ: 8.92–7.60 (14H, m, naphthyl-H×2) 8.81 (1H, s, C$_6$—H of the pyridine ring) 7.98 (1H, s, C$_3$—H of the pyridine ring)

Example 70

Preparation of
4-(4-benzyloxycarbonyl)benzoyloxy-2-pyridone

A 20 ml quantity of a solution of 4.60 g of (4-benzyloxycarbonyl)benzoyl chloride in dioxane was added to 20 ml of a solution of 1.80 g of 4-hydroxy-2-pyridone and 7.50 g of triethylamine in dioxane. The mixture was refluxed for 6 hours, left to stand for cooling and concentrated. The concentrate was extracted with ethyl acetate and washed with water. The ethyl acetate was distilled off and the residue was subjected to silica gel column chromatography using as an eluent 2% methanol-chloroform, giving 0.80 g of the title compound in a yield of 14%.

NMR(DMSO-$d_6$)$\delta$: 11.90 (1H, bs, NH) 8.20 (4H, bs,

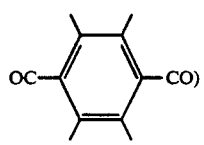

7.39–7.50 (6H, m, phenyl-H and $C_6$—H of the pyridine ring) 6.22–7.34 (2H, m, $C_{3,5}$—H of the pyridine ring) 5.41 (2H, s,

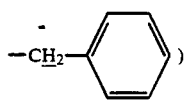

Example 71

Preparation of
2-benzoyloxy-5-bromo-4-hydroxypyridine

There were mixed 0.15 g of potassium fluoride, 0.35 g of 18-crown-6 and 50 ml of acetonitrile. The mixture was refluxed for 30 minutes and 0.50 g of 5-bromo-2,4-dibenzoyloxypyridine was added thereto. The mixture was refluxed overnight, left to stand for cooling and concentrated. The concentrate was extracted with ethyl acetate and washed with water. The ethyl acetate layer was concentrated and the concentrate was treated with ether, giving 0.23 g of the title compound in a yield of 62%.

NMR(DMSO-$d_6$)$\delta$: 12.10 (1H, broad, OH) 8.36 (1H, s, $C_6$—H of the pyridine ring) 8.07–8.17 (2H, m,

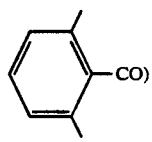

7.60–7.73 (3H, m,

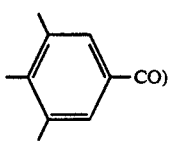

6.81 (1H, s, $C_3$—H of the pyridine ring)

Example 72

Preparation of 5-bromo-4-benzoyloxy-2-pyridone and 5-bromo-2,4-dibenzoyloxypyridine A 2.00 g quantity of 5-bromo-4-hydroxy-2-pyridone was suspended in 100 ml of pyridine. To the suspension was added dropwise 2.20 g of benzoyl chloride and the mixture was reacted at room temperature for 4 hours. After completion of the reaction, the mixture was concentrated and the residue was stirred in ether overnight. The crystals precipitated were separated by filtration, affording 1.01 g of the desired monobenzoyloxy product in a yield of 33%. The ether was concentrated and the concentrate was applied to silica gel column chromatography using as an eluent petroleum ether-chloroform (1:2), affording 1.44 g of the desired dibenzoyloxy product in a yield of 34%. Monobenzoyloxy product (5-bromo-4-benzoyloxy-2-pyridone)

NMR(DMSO-$d_6$)$\delta$: 8.08–8.17 (2H, m,

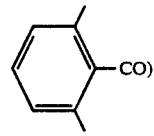

7.92 (1H, s, $C_6$—H of the pyridine ring) 7.62–7.73 (3H, m,

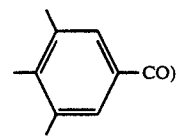

6.65 (1H, s, $C_3$—H of the pyridine ring) Dibenzoyloxy product (5-bromo-2,4-dibenzoyloxypyridine)

NMR(CDCl$_3$)$\delta$: 8.63 (1H, s, $C_6$—H of the pyridine ring) 8.19–8.27 (4H, m,

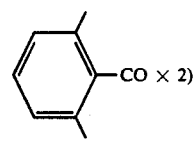

7.40–7.65 (7H, m, $C_3$—H of the pyridine ring and

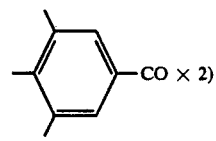

Example 73

Preparation of
2,4-bis(trimethylsilyloxy)-5-chloropyridine

A 50 ml quantity of hexamethyldisilazane was added to 9.6 g of 5-chloro-4-hydroxy-2(1H)-pyridone. The mixture was stirred in an oil bath at 140° C. overnight. The insolubles were removed by filtration and the fil-

Example 74

Preparation of 2-acetoxy-5-chloro-4-hydroxypyridine

A 2.09 ml quantity of acetyl bromide and 0.10 ml of stannic chloride were added to a solution of 5.00 g of 2,4-bis(trimethylsilyloxy)-5-chloropyridine in 250 ml of dried dichloromethane. The mixture was stirred at room temperature for 3.5 hours. The mixture was neutralized with triethylamine and the solvent was distilled off. The residue was subjected to silica gel column chromatography using 40% ethyl acetate-benzene as an eluent, giving 2.07 g of the title compound in a yield of 64%.

M.p. 270° to 272° C.

NMR(DMSO-$d_6$)$\delta$: 11.90 (1H, bs, OH) 8.20 (1H, s, $C_6$—H) 6.69 (1H, s, $C_3$—H) 2.27 (3H, s, COCH$_3$)

Example 75

Preparation of 5-chloro-4-hydroxy-1-(2-tetrahydrofuranyl)-2-pyridone

A 10 ml quantity of hexamethyldisilazane was added to 1.00 g of 5-chloro-4-hydroxy-2(1H)-pyridone. The mixture was refluxed for 6 hours. The excess hexamethyldisilazane was distilled off and the oily residue was dissolved in 50 ml of dichloromethane. To the solution were added 1.00 g of 2-acetoxy tetrahydrofuran and 0.1 ml of stannic chloride and the mixture was stirred at room temperature overnight. The mixture was neutralized with triethylamine and the solvent was distilled off. To the residue was added methanol and the mixture was stirred at room temperature for 2 hours. The solvent was distilled off again and the residue was subjected to silica gel column chromatography using as an eluent 2% methanolchloroform, giving 1.07 g of the title compound in a yield of 73.5%.

M.p. 170° to 173° C.

NMR(DMSO-$d_6$)$\delta$: 11.6 (1H, bs, OH) 7.59 (1H, s, $C_6$—H) 6.09-5.99 (1H, q,

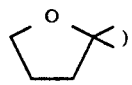

5.76(1H, s, $C_3$—H) 4.39-3.73 (2H, m,

2.42-1.82 (4H, m,

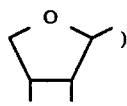

Example 76

Preparation of 4-hydroxy-1-(3-phthalidyl)-2-pyridone

A 10 ml quantity of hexamethyldisilazane was added to 1.00 g of 4-hydroxy-2-pyridone. The mixture was refluxed for 6 hours. The reaction mixture was concentrated under a reduced pressure and 2.29 g of acephthalide was added to the residue. The mixture was stirred at room temperature overnight. Methanol was added to the reaction mixture and the mixture was stirred at room temperature for 15 minutes. The resulting mixture was concentrated under a reduced pressure. The concentrate was subjected to silica gel column chromatography using as an eluent 1% methanolchloroform, giving 0.62 g of the title compound in a yield of 30%.

M.p. 239° to 241° C.

NMR(DMSO-$d_6$)$\delta$: 11.05 (1H, bs, OH) 8.29-7.52 (5H, m,

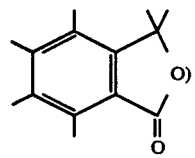

6.99 (1H, d, J=8 Hz, $C_6$—H) 5.88 (1H, dd, $J_{3,5}$=2 Hz, $J_{5,6}$=8 Hz, $C_5$—H) 5.65 (1H, d, J=2 Hz, $C_3$—H)

Example 77

Preparation of 1-benzyloxymethyl-5-chloro-4-hydroxy-2-pyridone

The general procedure of Example 75 was repeated with the exception of using benzyloxymethyl chloride in place of 2-acetoxytetrahydrofuran used in Example 75 and acetonitrile in place of dichloromethane used in Example 75, thereby producing the title compound in a yield of 57%.

M.p. 165° to 167° C.

NMR(DMSO-$d_6$)$\delta$: 11.65 (1H, bs, OH) 7.92 (1H, s, $C_6$—H) 7.31 (5H, s, phenyl-H) 5.77 (1H, s, $C_3$—H) 5.27 (2H, s, —NCH$_2$O—) 4.55 (2H, s,

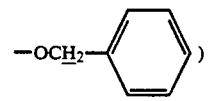

Example 78

Preparation of 5-chloro-1-ethoxymethyl-4-hydroxy-2-pyridone

The general procedure of Example 75 was repeated with the exception of using chloromethylethyl ether in place of 2-acetoxytetrahydrofuran used in Example 75, giving 5-chloro-1-ethoxymethyl-4-hydroxy-2(1H)-pyridone in a yield of 39%.

M.p. 217° to 219° C.

NMR(DMSO-$d_6$)$\delta$: 11.63 (1H, bs, OH) 7.87 (1H, s, $C_6$—H) 5.75 (1H, s, $C_3$—H) 5.16 (2H, s, N—CH$_2$—O—) 3.49 (2H, q, J=7 Hz, —OCH$_2$CH$_3$) 1.09 (3H, t, J=7 Hz, —OCH$_2$CH$_3$)

Example 79

Preparation of 2-benzoyloxy-5-chloro-4-hydroxy-pyridine

The general procedure of Example 75 was repeated with the exception of using benzoyl chloride in place of 2-acetoxytetrahydrofuran used in Example 75, giving the title compound in a yield of 51%. M.p. (The compound softened at 184° C.)

NMR(DMSO-d$_6$)δ: 8.27 (1H, s, C$_6$—H) 8.16–8.07 (2H, m,

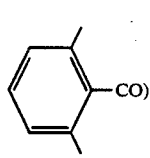

7.78–7.51 (3H, m,

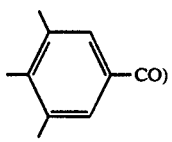

6.91 (1H, s, C$_3$—H)

Example 80

Preparation of 4-benzoyloxy-5-chloro-2-pyridine

A 0.31 ml quantity of aniline was added to a solution of 1.00 g of 5-chloro-2,4-dibenzoyloxypyridine in 30 ml of dioxane and the mixture was left to stand at 90° to 100° C. for 5 hours. Thereto was added 0.15 ml of aniline and the mixture was further subjected to reaction for 2 hours. The solvent was distilled off and the residue was washed with water. The precipitate was recovered by filtration and applied to silica gel column chromatography to conduct gradient elution using chloroform and 2% methanol-chloroform, giving 0.26 g of the title compound in a yield of 37%. The compound thus obtained was found identical in melting point and in NMR spectrum data with the compound prepared in Example 10.

Example 81

Preparation of 6-benzoyloxy-3-cyano-2-hydroxypyridine

A 0.51 ml quantity of triethylamine and 0.43 ml of benzoyl chloride were added to a solution of 1.00 g of 3-cyano-2,6-dihydroxypyridine in 40 ml of N,N-dimethylacetamide. The mixture was stirred at room temperature for 15 minutes. To the reaction mixture were added 0.51 ml of triethylamine and 0.43 ml of benzoyl chloride, and the mixture was stirred at room temperature for 15 minutes. The reaction mixture was filtered and the filtrate was concentrated under a reduced pressure. The concentrate was washed with chloroform and with water, giving 1.06 g of the title compound in a yield of 60%.

NMR(DMSO-d$_6$)δ: 12.76 (1H, bs, OH or NH) 8.33 (1H, d, J=8 Hz, C$_4$—H of the pyridine ring) 8.17–8.07 (2H, m,

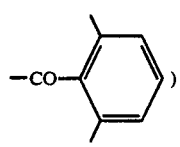

7.94–7.58 (3H, m,

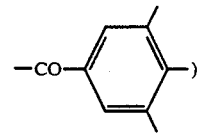

6.95 (1H, d, J=8 Hz, C$_5$—H of the pyridine ring)

Examples 82 to 86

The following compounds were prepared in the same manner as in Example 81.

Example 82

3-cyano-6-(2,4-dichlorobenzoyloxy)-2-hydroxypyridine

NMR((CD$_3$)$_2$CO)δ: 8.29 (1H, d, J=8 Hz, C$_4$—H of the pyridine ring) 8.17 (1H, d, J=8 Hz,

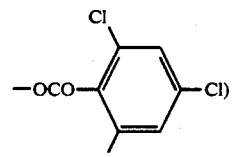

7.74 (1H, d, J=2 Hz,

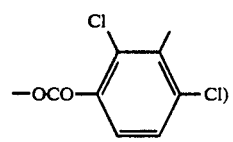

7.61 (1H, dd, J=8 Hz, J=2 Hz,

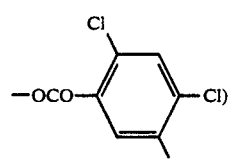

7.01 (1H, d, J=8 Hz, C$_6$—H of the pyridine ring)

Example 83

3-cyano-6-(2-furoyloxy)-2-hydroxypyridine

NMR(DMSO-d$_6$)δ: 8.32 (1H, d, J=8 Hz, C$_4$—H of the pyridine ring) 8.14 (1H, dd, J=1Hz, J=2 Hz,

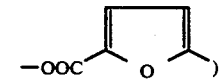

7.63 (1H, dd, J=1Hz, J=4 Hz,

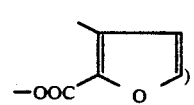

6.95 (1H, d, J=8 Hz, C$_5$—H of the pyridine ring) 6.82 (1H, dd, J=2 Hz, J=4 Hz,

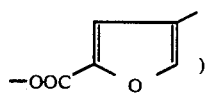

Example 84

3-cyano-6-(3,4,5-trimethoxybenzoyloxy)-2-hydroxypyridine

NMR(DMSO-d₆)δ: 8.32 (1H, d, J=8 Hz, C₄—H of the pyridine ring) 7.39 (2H, s,

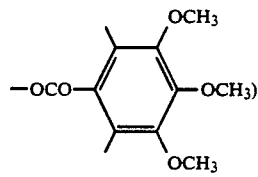

6.93 (1H, d, J=8 Hz, C₆—H of the pyridine ring) 3.89 (6H, s,

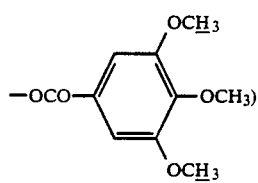

3.80 (3H, s,

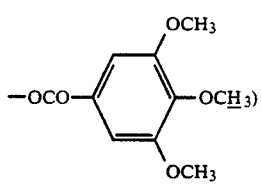

Example 85

3-cyano-6-(2-thenoyloxy)-2-hydroxypyridine

NMR(DMSO-d₆)δ: 8.32 (1H, d, J=8 Hz, C₄—H of the pyridine ring) 8.15 (1H, dd, J=1Hz, J=5 Hz,

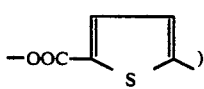

8.06 (1H, dd, J=1Hz, J=4 Hz,

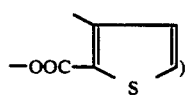

7.33 (1H, dd, J=4 Hz, J=5 Hz,

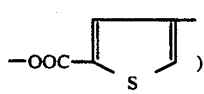

6.96 (1H, d, J=8 Hz, C₅—H of the pyridine ring)

Example 86

3-chloro-6-(4-fluorobenzoyloxy)-2-hydroxypyridine

NMR(DMSO-d₆)δ: 12.27 (1H, bs, OH or NH) 8.26–8.10 (2H, m,

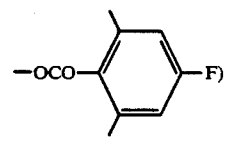

7.96 (1H, d, J=8 Hz, C₄—H of the pyridine ring) 7.43 (2H, t, J=9 Hz,

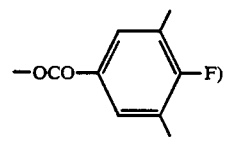

6.79 (1H, d, J=8 Hz, C₅—H of the pyridine ring)

Example 87

Preparation of 4-(2-thenoyloxy)-2-pyridone

The general procedure of Example 18 was followed using 2.00 g of 4-hydroxy-2-pyridone and 3.17 g of 2-thenoyl chloride, thereby producing 2.98 g of the title compound in a yield of 75%.

NMR(DMSO-d₆)δ: 11.69 (1H, bs, N—H, disappeared by addition of D₂O) 8.14–7.99 (2H, m, C₃,₅—H of the thiophene ring) 7.48 (1H, d, J=8 Hz, C₆—H of the pyridine ring) 7.35–7.26 (1H, m, C₄—H of the thiophene ring) 6.26–6.17 (2H, m, C₃,₅—H of the pyridine ring)

Example 88

Preparation of 6-benzoyloxy-3-chloro-2-hydroxypyridine

Benzoic anhydride (5.81 g) was added to a solution of 3.74 g of 3-chloro-2,6-dihydroxypyridine in 100 ml of pyridine and the mixture was stirred at room temperature for 1.5 hours. The reaction mixture was concentrated under reduced pressure. The residue was washed with ether and recrystallized from acetone, giving 3.07 g of the title compound in a yield of 48%.

NMR(DMSO-d₆)δ: 12.25 (1H, bs, OH or NH) 8.15–7.92 (3H, m, C₄—H of the pyridine ring and

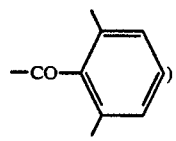

7.79–7.61 (3H, m,

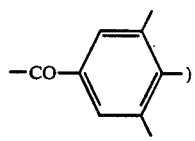

6.80 (1H, d, J=8 Hz, C$_5$—H of the pyridine ring)

Example 89

Preparation of 4-acetoxy-2-benzoyloxypyridine

A 0.77 g quantity of 4-acetoxy-2-pyridone was suspended in 30 ml of dioxane. To the suspension were added 2.09 ml of triethylamine and 0.58 ml of benzoyl chloride and the mixture was stirred at room temperature for 2.5 hours. The reaction mixture was concentrated under reduced pressure and the residue was subjected to silica gel chromatography using, as an eluent, chloroform, giving 0.95 g of the title compound in a yield of 73%.

NMR(CDCl$_3$)δ: 8.42 (1H, d, J=6 Hz, C$_6$—H of the pyridine ring) 8.25–7.98 (2H, m,

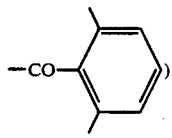

7.63–7.39 (3H, m,

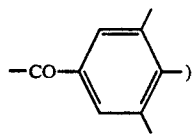

7.25–7.06 (2H, m, C$_{3,5}$—H of the pyridine ring) 2.29 (3H, s, COCH$_3$)

Example 90

Preparation of 6-benzoyloxy-2-(4-bromobenzoyloxy)-3-cyanopyridine

Triethylamine (3.46 ml) and 1.82 g of 4-bromobenzoyl chloride were added to a solution of 2.00 g of 6-benzoyloxy-3-cyano-2-hydroxypyridine in 50 ml of dioxane. The mixture was stirred at room temperature for 1 hour. The salt thus produced was separated by filtration and the filtrate was concentrated. The concentrate was applied to silica gel column chromatography using, as an eluent, chloroform, giving 2.97 g of the title compound in a yield of 84%.

NMR(DMSO-d$_6$)δ: 8.80 (1H, d, J=8 Hz, C$_4$—H of the pyridine ring) 8.19–7.53 (10H, m, C$_5$—H of the pyridine ring and

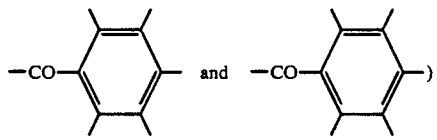

Example 91

Preparation of 6-benzoyloxy-2-(4-chlorobenzoyloxy)-3-cyanopyridine

The general procedure of Example 90 was followed using 1.00 g of 6-benzoyloxy-3-cyano-2-hydroxypyridine and 0.72 g of 4-chlorobenzoyl chloride, thereby producing 1.29 g of the title compound in a yield of 82%.

NMR(DMSO-d$_6$)δ: 8.82 (1H, d, J=8 Hz, C$_4$—H of the pyridine ring) 8.23–7.59 (10H, m, C$_5$—H of the pyridine ring and

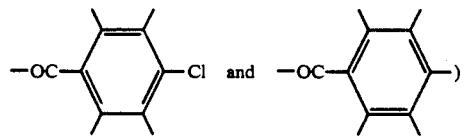

Example 92

Preparation of 3-cyano-2,6-dibenzoyloxypyridine

The general procedure of Example 90 was followed using 1.00 g of 6-benzoyloxy-3-cyano-2-hydroxypyridine and 0.58 g of benzoyl chloride, thereby producing 1.15 g of the title compound in a yield of 80%.

NMR(DMSO-d$_6$)δ: 8.81 (1H, d, J=8 Hz, C$_4$—H of the pyridine ring) 8.24–8.11 (4H, m,

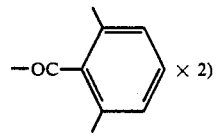

7.81–7.63 (7H, m, C$_5$—H of the pyridine ring and

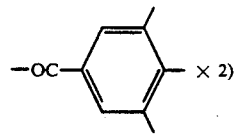

Example 93

Preparation of 6-(2-chlorobenzoyloxy)-3-cyano-2-hydroxypyridine

The general procedure of Example 81 was followed using 2.00 g of 3-cyano-2,6-dihydroxypyridine and 2.57 g of 2-chlorobenzoyl chloride, thereby producing 2.21 g of the title compound in a yield of 55%.

H-NMR(DMSO-d$_6$)δ: 8.35 (1H, d, J=8 Hz, C$_4$—H of the pyridine ring) 8.10 (1H, dd, J=7 Hz, J=1 Hz,

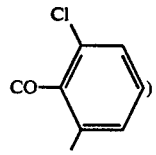

7.75–7.40 (3H, m, m,

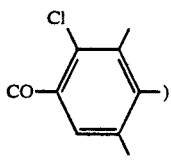

7.00 (1H, d, J=8 Hz, C$_5$—H of the pyridine ring)

Example 94

Preparation of 3-cyano-6-(3-methylbenzoyloxy)-2-hydroxypyridine

The general procedure of Example 81 was followed using 2.00 g of 3-cyano-2,6-dihydroxypyridine and 2.27 g of 3-methylbenzoyl chloride, thereby producing 2.16 g of the title compound in a yield of 58%.

NMR(DMSO-d$_6$)δ: 8.33 (1H, d, J=8 Hz, C$_4$—H of the pyridine ring) 8.00–7.85 (2H, m,

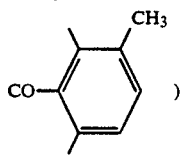

7.65–7.41 (2H, m,

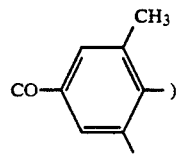

6.94 (1H, d, J=8 Hz, C$_5$—H of the pyridine ring)

Example 95

Preparation of 6-(2,4-dichlorobenzoyloxy)-2-hydroxypyridine

The general procedure of Example 81 was followed using 3.00 g of 2,6-dihydroxypyridine hydrogen-chloride and 4.26 g of 2,4-dichlorobenzoyl chloride, thereby producing 4.49 g of the title compound in a yield of 78%.

NMR(DMSO-d$_6$)δ: 8.10 (1H, d, J=9 Hz,

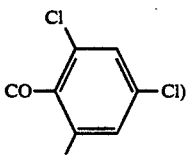

7.90–7.58 (3H, m,

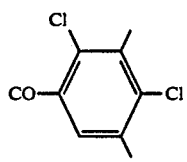

and C$_4$—H of the pyridine ring) 6.78 (1H, d, J=8 Hz, C$_5$—H of the pyridine ring) 6.64 (1H, d, J=8 Hz, C$_3$—H of the pyridine ring)

Example 96

Preparation of 2,6-dihydroxy-3-chloropyridine (compound of the formula (1) wherein R$^1$=R$^2$=H, R$^3$=Cl, R$^4$=OH)

To 30 ml of carbon tetrachloride were added 1.46 g of 2,6-dibenzyloxypyridine and 1.45 g of potassium carbonate. Thereto was added dropwise a solution of 0.4 ml of surfuryl chloride in 10 ml of carbon tetrachloride at room temperature over a period of 2 hours. After addition, the mixture was stirred for 1 hour and the reaction mixture was filtered. The filtrate was concentrated and the concentrate was subjected to silica gel column chromatography using n-hexane and benzene (7:1) as an eluent, affording 1.2 g of a colorless oil in a yield of 74%.

| | Elementary analysis | | |
|---|---|---|---|
| | C | H | N |
| Calcd. (%) | 70.05 | 4.95 | 4.30 |
| Found (%) | 70.02 | 4.82 | 4.25 |

A 6.5 g portion of 2,6-dibenzyloxy-3-chloropyridine thus obtained was dissolved in 130 ml of ethanol. To the solution was added 429 mg of 5% palladium carbon. The mixture was subjected to catalytic reduction at atmospheric pressure. The reaction mixture was filtered and the filtrate was concentrated to obtain red crystals which were recrystallized from methanol-ethyl acetate, affording 410 mg of the title compound as pale green, pyramidal crystals in a yield of 14%. M.p. 300° C. or higher (decomposition). (The compound changed its color at or above 220° C. and was blackened at or above 250° C.)

Pharmacological Test I

Sarcoma-180 subcultured as ascites in ICR mice was diluted with a physiological saline solution and subcutaneously transplanted into the backs of ICR mice in two groups (i.e. one group to be applied with a medicinal preparation and the other (control group) not to be applied therewith) in an amount of 2×10$^7$ ascites cells each. A medicinal preparation suspended in a 5% solution of gum arabic was orally administered to each of mice once a day for 7 consecutive days from 24 hours after the transplantation.

The solid tumor was extirpated from under the dorsal skin of mice on the 10th day after the transplantation to measure the weight of the tumor. There was determined the ratio (T/C) of the weight of tumor (T) cut out from the group of mice applied with the preparation to the weight of tumor (C) from the group of mice not applied therewith. The 50% tumor inhibition dose (ED$_{50}$ value) in which T/C is 0.5 was found from the dose-response curve of dosage and the ratio (T/C).

A table below shows the ED$_{50}$ values obtained by using, as test drugs, antitumor agents in single dosages, or in combination with 2,4-dihydroxypyridine (shown as 2,4-DHP in the table) for comparison in a ratio by mole of 1:1, or in mixture with each of compounds of this invention, i.e. active ingredients capable of increasing the antitumor activity according to this invention (pyridine derivatives of the formula (1)) in a ratio by mole of 1:1. In the table below, the antitumor agents and the active ingredients of this invention are indicated with the following abbreviations and symbols.

Antitumor agents

5-FU: 5-fluorouracil
FT-207: 1-(2-tetrahydrofuryl-5-fluorouracil)
HCFU: 1-n-hexylcarbamoyl-5-fluorouridine
5-DFUR: 5'-deoxy-5-fluorouridine
FUdR: 2'-deoxy-5-fluorouridine
OFU: 1-ethoxymethyl-5-fluorouracil
TK-117: 2-deoxy-5-fluoro-3-(3,4-methylenedioxybenzoyl)uridine
FUR: 5-fluorouridine
FF-707: 2'-deoxy-5-fluoro-3',5'-bis-O-(4-methoxyphenoxycarbonyl)-3-(n-propoxybenzoyl)uridine
Anti-T-1: 2'-deoxy-3'-O-benzyl-5-fluorouridine
Anti-T-2: 5'-O-acetyl-3'-O-benzyl-2'-deoxy-5-fluorouridine
Anti-T-3: 2'-deoxy-3'-O-benzyl-3-benzoyl-5-fluorouridine
Anti-T-4: 2'-deoxy-3'-O-(4-chlorobenzyl)-5-fluorouridine

Compounds of this Invention

Compound-1: 2,4-dihydroxy-5-chloropyridine
Compound-2: 2,6-dihydroxy-3-chloropyridine
Compound-3: 2,4-dihydroxy-5-bromopyridine
Compound-4: 2,4-dihydroxy-5-methylpyridine
Compound-5: 2,6-dihydroxy-3-cyanopyridine
Compound-6: 2,6-dihydroxy-3-nitropyridine
Compound-7: 2,6-dihydroxypyridine
Compound-8: 2,4-dihydroxy-5-carboxypyridine
Compound-9: 2,4-dihydroxy-5-ethoxycarbonylpyridine
Compound-10: 2,4-dihydroxy-3,5-dichloropyridine
Compound-11: 2,4-dihydroxy-3,5-dibromopyridine
Compound-12: 2,4-dihydroxy-3-chloropyridine
Compound-13: 2,4-dihydroxy-3-bromopyridine
Compound-14: 2,4-dihydroxy-3-methylpyridine
Compound-15: 2,4-dihydroxy-3-aminopyridine
Compound-16: 2,6-dihydroxy-3-carbamoylpyridine
Compound-17: 2,4,6-trihydroxypyridine
Compound-18: 5-chloro-4-octadecanoyloxy-2-pyridone
Compound-19: 2,4-dibenzoyloxypyridine
Compound-20: 6-benzoyloxy-2-pyridone
Compound-21: 2-benzoyloxy-5-chloro-4-hydroxypyridine
Compound-22: 5-chloro-4-(2-methylbenzoyloxy)-2-pyridone
Compound-23: 4-benzoyloxy-5-chloro-2-pyridone
Compound-24: 2,4-bis(4-ethoxybenzoyloxy)pyridine
Compound-25: 5-chloro-1,2-dihydro-4-hydroxy-2-oxo-1-(2-tetrahydrofuranyl)pyridine
Compound-26: 5-chloro-1,2-dihydro-4-hydroxy-2-oxo-1-methoxymethylpyridine
Compound-28: 6-benzoyloxy-3-cyano-2-hydroxypyridine
Compound-29: 3-cyano-6-(3,4,5-trimethoxybenzoyl)-2-hydroxypyridine
Compound-30: 3-cyano-6-(2-furoyloxy)-2-hydroxypyridine
Compound-31: 3-cyano-6-(3,4-dichlorobenzoyloxy)-2-hydroxypyridine
Compound-32: 6-benzoyloxy-2-(4-bromobenzoyloxy)-3-cyanopyridine

| Antitumor agent | Compound of this invention | $ED_{50}$ (mg/kg) |
|---|---|---|
| 5-FU | — | 25 |
| " | Compound 1 | 7 |
| " | Compound 2 | 10 |
| " | Compound 18 | 8 |
| " | Compound 19 | 7 |
| " | Compound 20 | 5 |
| FT-207 | — | 110 |
| " | Compound 1 | 8 |
| " | Compound 2 | 8 |
| " | Compound 3 | 6 |
| " | Compound 4 | 7 |
| " | Compound 5 | 8 |
| " | Compound 6 | 8 |
| " | Compound 7 | 10 |
| " | Compound 8 | 45 |
| " | Compound 9 | 50 |
| " | Compound 10 | 45 |
| " | Compound 11 | 45 |
| " | Compound 12 | 40 |
| " | Compound 13 | 65 |
| " | Compound 14 | 60 |
| " | Compound 15 | 65 |
| " | Compound 16 | 65 |
| " | Compound 17 | 75 |
| " | Compound 20 | 4 |
| " | Compound 21 | 6 |
| TK-117 | — | 25 |
| " | Compound 1 | 12 |
| " | Compound 2 | 12 |
| HCFU | — | 70 |
| " | Compound 1 | 15 |
| " | Compound 2 | 25 |
| " | Compound 22 | 10 |
| " | Compound 21 | 8 |
| 5'-DFUR | — | 90 |
| " | Compound 1 | 7 |
| " | Compound 2 | 7 |
| " | Compound 3 | 8 |
| " | Compound 23 | 5 |
| " | Compound 24 | 7 |
| FUdR | — | 23 |
| " | Compound 1 | 10 |
| " | Compound 22 | 5 |
| " | Compound 20 | 2 |
| OFU | — | 180 |
| " | Compound 2 | 25 |
| FF-707 | — | 20 |
| " | Compound 1 | 12 |
| FUR | Compound 1 | 7 |
| Anti-T-1 | — | 8 |
| " | Compound 1 | 5 |
| " | Compound 2 | 0.5 |
| " | Compound 3 | 4 |
| " | Compound 4 | 2 |
| " | Compound 25 | 5 |
| " | Compound 19 | 3 |
| " | Compound 26 | 4 |
| " | Compound 28 | 3.5 |
| " | Compound 29 | 2.5 |
| " | Compound 30 | 2.5 |
| " | Compound 31 | 2 |
| " | Compound 32 | 2 |
| Anti-T-2 | — | 5 |
| " | Compound 1 | 3 |
| " | Compound 25 | 3 |
| Anti-T-3 | — | 3 |
| " | Compound 1 | 2 |
| Anti-T-4 | — | 1 |
| FT-207 | 2,4-DHP (comparison) | 36 |
| OFU | " | 80 |
| 5'-DFUR | " | 25 |
| FUdR | " | 13 |

The results obtained above show that when incorporated in an antitumor agent, the pyridine derivative of this invention can increase the antitumor activity of the agent in a marked degree.

Pharmacological Test II (acute toxicity)

3'-O-benzyl-2'-deoxy-5-fluorouridine and 3'-O-benzyl-5'-O-acetyl-2'-deoxy-5-fluorouridine were each orally administered to 5-week-old ICR male mice (8 mice in each group) to check the mice for the symptoms, change of body weight and mortality by observing the mice for 14 consecutive days after the administration of the compounds. The $LD_{50}$ value was determined from the mortality by the Litchfield-Wilcoxon method with 10 the results shown below in Table 2.

TABLE 2

| Test Compound | $LD_{50}$ (mg/kg) |
|---|---|
| 3'-O-benzyl-2'-deoxy-5-fluorouridine | Over 1000 |
| 3'-O-benzyl-5'-O-acetyl-2'-deoxy-5-fluorouridine | Over 1000 |

Pharmacological Test III (acute toxicity)

2,6-dihydroxy-3-cyanopyridine was intravenously administered to 5-week-old ICR male mice (8 mice in each group) to check the mice for the symptoms, change of body weight and mortality by observing the mice for 14 consecutive days after the administration of the compounds. The $LD_{50}$ value as determined from the mortality by the Litchfield-Wilcoxon method was 315 mg/kg.

| Preparation Example 1 | |
|---|---|
| 2,6-Dihydroxy-3-chloropyridine | 20 mg |
| 2'-Deoxy-3'-O-benzyl-5'-O-acetyl-5-fluorouridine | 50 mg |
| Lactose | 110 mg |
| Crystalline cellulose | 67 mg |
| Magnesium stearate | 3 mg |

Capsules (250 mg each) were prepared which had the foregoing composition.

| Preparation Example 2 | |
|---|---|
| 2,6-Dihydroxy-3-chloropyridine | 10 mg |
| 2'-Deoxy-3'-O-benzyl-5-fluorouridine | 20 mg |
| Lactose | 107 mg |
| Crystalline cellulose | 60 mg |
| Magnesium stearate | 3 mg |

Capsules (200 mg each) were prepared which had the foregoing composition.

| Preparation Example 3 | |
|---|---|
| 2,6-Dihydroxy-3-chloropyridine | 10 mg |
| 5-Fluorouracil | 10 mg |
| Lactose | 180 mg |
| Corn starch | 290 mg |
| Hydroxypropylmethyl cellulose | 10 mg |

Granules (500 mg each wrapper) were prepared which had the foregoing composition.

| Preparation Example 4 | |
|---|---|
| 2,6-Dihydroxy-3-chloropyridine | 20 mg |
| 2'-Deoxy-3'-O-benzyl-5'-O-acetyl-5-fluorouridine | 10 mg |
| Macrogol 300 | 500 mg |

-continued

| Preparation Example 4 | |
|---|---|
| Distilled water for injection | Suitable amount |

Injection solutions (5 ml each ampoule) were prepared which had the foregoing composition.

| Preparation Example 5 | |
|---|---|
| 2,6-Dihydroxy-3-chloropyridine | 10 g |
| 5-Fluorouracil | 10 g |
| Lactose | 10 g |
| Corn starch | 24 g |
| Crystalline cellulose | 25 g |
| Methyl cellulose | 1.5 g |
| Magnesium stearate | 1 g |

2,6-Dihydroxy-3-chloropyridine, 5-fluorouracil, lactose, corn starch and crystalline cellulose were thoroughly mixed and the mixture was granulated with a 5% aqueous solution of methyl cellulose. The granulate was carefully dried while passed through a 200-mesh screen. The dried granulate was passed through a 200-mesh screen and mixed with magnesium stearate. The mixture was pressed into tablets, preparing one thousand tablets for oral administration.

What is claimed is:

1. A pharmaceutical composition having potentiated anti-cancer activity comprising:

I. an anti-cancer effective amount of an anti-cancer compound selected from the group consisting of 5-fluorouracil and compounds capable of producing 5-fluorouracil in vivo, wherein said anti-cancer compound is at least one selected from the group consisting of:

a) a 5-fluorouracil compound having the formula

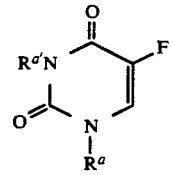

wherein $R^a$ and $R^{a1}$ are each the same or different and represent hydrogen, phthalidyl, tetrahydrofuranyl, tetrahydropyranyl, lower alkylcarbamoyl, lower alkoxy-lower alkyl, phenyl-lower alkoxy-lower alkyl, acyl or a group

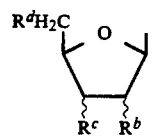

wherein $R^b$, $R^c$ and $R^d$ are each the same or different and represent hydrogen, hydroxy, phenyl-lower alkoxy, phenyl-lower alkoxy-lower alkoxy, lower alkanoyloxy, or aroyloxy or aryloxycarbonyloxy which may have on the phenyl ring 1 to 3 substituents selected from among lower alkyl, lower alkoxy, nitro and halogen; when both $R^b$ and $R^c$ are hydroxy, they may be combined together through an alkylidene or an arylidene group to form an alkylidenedioxy or an arylidenedioxy group; wherein $R^b$ is hydrogen, one of $R^c$ and $R^d$ cannot be phenyl-lower alkoxy when the other is hydroxy, lower alkanoyloxy or aroyloxy; wherein said acyl represented by $R^a$ and $R^{a1}$ is selected from the group consisting of alkanoyl group having 1 to 20 carbon atoms and optionally substituted with phenyl-lower alkoxycarbonyl, lower alkylcarbamoyl, phenyl or phenoxy; arylcarbonyl group which may be optionally substituted with lower alkylenedioxy or with 1 to 3 substituents selected from the group consisting of halogen, lower alkyl, lower alkoxy, nitro, phenyl-lower alkoxycarbonyl, carboxyl, hydroxy, guanidyl, phenyl-lower alkoxy and amino optionally substituted with lower alkyl; lower alkoxycarbonyl group; phenoxycarbonyl group; pyridylcarbonyl group; thienylcarbonyl group; and furanylcarbonyl group;

b) a compound of the formula

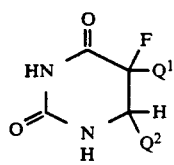

(2-b)

wherein $Q^1$ is lower alkoxycarbonyl and $Q^2$ is lower alkoxy or

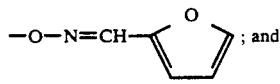; and c) a 2'-deoxy-5-fluorouridine compound having the formula

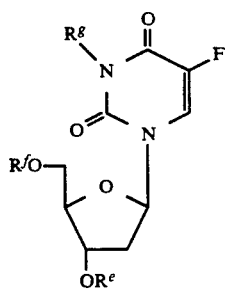

(3)

wherein one of $R^e$ and $R^f$ represents phenyl-lower alkyl group optionally having a substituent selected from the group consisting of lower alkyl, lower alkoxy, halogen, carboxy, lower alkoxycarbonyl and di(lower alkyl)amino on the phenyl ring, phenyl-lower alkyl group substituted with lower alkylenedioxy or phenyl on the phenyl ring, phenyl-lower alkenyl or naphthyl-lower alkyl group, and the other of $R^e$ and $R^f$ represents hydrogen or acyl, $R^g$ represents hydrogen, acyl or tetrahydrofuranyl, wherein said acyl represented by $R^e$, $R^f$ or $R^g$ is selected from the group consisting of substituted or unsubstituted $C_{1-20}$ alkanoyl group, substituted or unsubstituted aryl-carbonyl group, 5- or 6-membered unsaturated hetero ring-carbonyl group having nitrogen, sulfur or oxygen atom as the hetero atom, carbonic acid ester residue, substituted or unsubstituted cycloalkyl carbonyl group, lower alkenyl carbonyl group and lower alkynyl carbonyl group, and II. about 0.1 to about 10 moles of a pyridine compound per mole of said anti-cancer compound, said pyridine compound having the formula

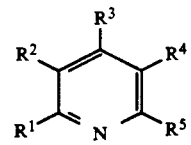

wherein $R^1$ is hydroxy or acyloxy, $R^2$ and $R^4$ are each hydrogen, halogen, amino, carboxyl, carbamoyl, cyano, nitro, lower alkyl, lower alkenyl or lower alkoxycarbonyl, $R^3$ and $R^5$ are each hydrogen, hydroxy or acyloxy, wherein the acyl moiety of said $R^1$, $R^3$ and $R^5$ acyloxy is selected from the group consisting of alkanoyl group having 1 to 20 carbon atoms and optionally substituted with phenyl-lower alkoxycarbonyl, lower alkylcarbamoyl, phenyl or phenoxy; arylcarbonyl group which may be optionally substituted with lower alkylenedioxy or with 1 to 3 substituents selected from the group consisting of halogen, lower alkyl, lower alkoxy, nitro, phenyl-lower alkoxycarbonyl, carboxyl, hydroxy, guanidyl, phenyl-lower alkoxy and amino optionally substituted with lower alkyl; lower alkoxycarbonyl group; phenoxycarbonyl group; pyridylcarbonyl group; thienylcarbonyl group; or furanylcarbonyl group; when at least one of $R^1$, $R^3$ and $R^5$ is hydroxy, the structure of 1-position on the pyridine ring can be

due to keto-enol tautomerism, said hydrogen attached to nitrogen being optionally substituted with a substituent selected from the group consisting of lower alkyl, tetrahydrofuranyl, tetrahydropyranyl, lower alkoxy-lower alkyl, phthalidyl, carbamoyl, lower alkoxycarbonyl-lower alkyl-carbamoyl, phenyl-lower alkoxy-lower alkyl, phenylcarbamoyl which may have a substituent on the phenyl ring, lower alkylcarbamoyl, carboxy-lower alkylcarbamoyl, lower alkylthio-lower alkyl and lower alkenyl, provided that the compound having the following formula is excluded,

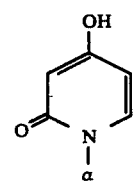

wherein α is hydrogen, lower alkyl, tetrahydrofuranyl, tetrahydropyranyl, lower alkoxy-lower alkyl, lower-alkyl-carbamoyl, lower alkylthio-lower alkyl or lower alkenyl.

2. A pharmaceutical composition as defined in claim 1, wherein said anti-cancer compound is selected from the group consisting of:

a) a 5-fluorouracil compound having the formula

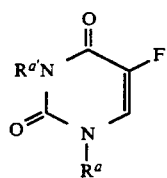

wherein $R^a$ and $R^{a1}$ are each the same or different and represent hydrogen, phthalidyl, tetrahydrofuranyl, tetrahydropyranyl, mono- or di($C_1$–$C_6$ alkyl) carbamoyl, $C_1$–$C_6$ alkoxy-$C_1$–$C_6$ alkyl, acyl or a group

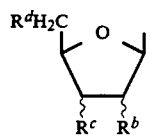

wherein $R^b$, $R^c$ and $R^d$ are each the same or different and represent hydrogen, hydroxy, phenyl-$C_1$–$C_6$ alkoxy, phenyl-$C_1$–$C_6$ alkoxy-$C_1$–$C_6$ alkoxy, $C_1$–$C_6$ alkanoyloxy, or aroyloxy or aryloxycarbonyloxy which may have on the phenyl ring 1 to 3 substituents selected from among $C_1$–$C_6$ alkyl, $C_1$–$C_6$ alkoxy, nitro and halogen; when both $R^b$ and $R^c$ are hydroxy, they may be combined together through an alkylidene or an arylidene group to form an alkylidenedioxy or an arylidenedioxy group; when $R^b$ is hydrogen, one of $R^c$ and $R^d$ cannot be phenyl-$C_1$–$C_6$ alkoxy when the other is hydroxy, $C_1$–$C_6$ alkanoyloxy or aroyloxy; wherein said acyl represented by $R^a$ and $R^{a'}$ is selected from the group consisting of alkanoyl group having 1 to 20 carbon atoms and optionally substituted with phenyl-($C_1$–$C_6$ alkoxy) carbonyl, mono-or di ($C_1$–$C_6$ alkyl) carbamoyl, phenyl or phenoxy; arylcarbonyl group which may be optionally substituted with $C_1$–$C_4$ alkylenedioxy or with 1 to 3 substituents selected from the group consisting of halogen, $C_1$–$C_6$ alkyl, $C_1$–$C_6$ alkoxy, nitro, phenyl-($C_1$–$C_6$ alkoxy) - carbonyl, carboxyl, hydroxy, quanidyl, phenyl-lower alkoxy and amino optionally substituted with $C_1$–$C_6$ alkyl; ($C_1$–$C_6$ alkoxy) - carbonyl group; phenoxycarbonyl group; pyridylcarbonyl group; thienylcarbonyl group; and furanylcarbonyl group;

b) a compound of the formula

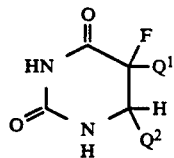

wherein $Q^1$ is ($C_1$–$C_6$ alkoxy) carbonyl and $Q^2$ is $C_1$–$C_6$ alkoxy or

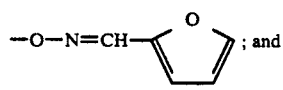; and c) a 2'-deoxy-5-fluorouridine compound having the formula

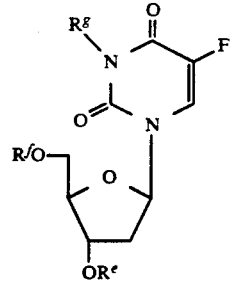

wherein one of $R^e$ and $R^f$ represents phenyl-$C_1$–$C_6$ alkyl group optionally having a substituted selected from the group consisting of $C_1$–$C_6$ alkyl, $C_1$–$C_6$ alkoxy, halogen, carboxy, ($C_1$–$C_6$ alkoxy) - carbonyl and di($C_1$–$C_6$ alkyl) amino on the phenyl ring, phenyl-$C_1$–$C_6$-alkyl group substituted with $C_1$–$C_4$ alkylenedioxy or phenyl on the phenyl ring, phenyl-$C_2$–$C_6$ alkenyl or naphthyl-$C_1$–$C_6$ alkyl group, and the other of $R^e$ and $R^f$ represents hydrogen or acyl, $R^g$ represents hydrogen, acyl or tetrahydrofuranyl, wherein said acyl represented by $R^e$, $R^f$ or $R^g$ is selected from the group consisting of substituted or unsubstituted $C_{1\text{-}20}$ alkanoyl group, substituted or unsubstituted aryl-carbonyl group, 5- or 6-membered unsaturated hetero ring-carbonyl group having nitrogen, sulfur or oxygen atom as the hetero atom, carbonic acid ester residue, substituted or unsubstituted ($C_3$–$C_8$ cycloalkyl)-carbonyl group, ($C_2$–$C_6$ alkenyl)-carbonyl group and ($C_2$–$C_8$ cycloalkyl)-carbonyl group, ($C_2$–$C_6$ alkenyl)-carbonyl group and ($C_2$–$C_6$ alkenyl)-carbonyl group, and wherein said pyridine compound has the formula

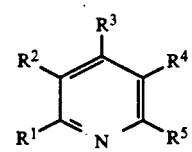

wherein $R^1$ is hydroxy or acyloxy, $R^2$ and $R^4$ are each hydrogen, halogen, amino, carboxyl, carbamoyl, cyano, nitro, $C_1$–$C_6$ alkyl, $C_2$–$C_6$ alkenyl or ($C_1$–$C_6$ alkoxy) carbonyl, $R^3$ and $R^5$ are each hydrogen, hydroxy or acyloxy, wherein the acyl moiety of said $R^1$, $R^3$ and $R^5$ acyloxy is selected from the group consisting of alkanoyl group having 1 to 20 carbon atoms and optionally substituted with phenyl-($C_1$–$C_6$ alkoxy) - carbonyl, mono- or di(C1–$C_6$ alkyl) carbamoyl, phenyl or phenoxy; arylcarbonyl group which may be optionally substituted with $C_1$–$C_4$ alkylenedioxy or with 1 to 3 substituents selected from the group consisting of halogen, $C_1$–$C_6$ alkyl, $C_1$–$C_6$ alkoxy, nitro, phenyl-($C_1$–$C_6$ alkoxy) carbonyl, carboxyl, hydroxy, guanidyl, phenyl-$C_1$–$C_6$ alkoxy and amino optionally substituted with $C_1$–$C_6$ alkyl; ($C_1$–$C_6$ alkoxy)carbonyl group; phenoxycarbonyl group; pyridylcarbonyl group; thienylcarbonyl group; or furanylcarbonyl group; when at least one of $R^1$, $R^3$ and $R^5$ is hydroxy, the structure of 1-position on the pyridine ring can be

due to keto-enol tautomerism, the hydrogen attached to nitrogen being optionally substituted with a substituent selected from the group consisting of $C_1$–$C_6$ alkyl, tetrahydrofuranyl, tetrahydropyranyl, $C_1$–$C_6$ alkoxy-$C_1$–$C_6$ alkyl, phthalidyl, carbamoyl, ($C_1$–$C_6$ alkoxy)carbonyl-($C_1$–$C_6$ alkyl)-carbamoyl, phenyl-$C_1$–$C_6$ - alkoxy-$C_1$–$C_6$ alkyl, phenyl-carbamoyl which may have a substituent on the phenyl ring, mono- or di($C_1$–$C_6$ alkyl) carbamoyl, carboxy-($C_1$–$C_6$ alkyl) carbamoyl, $C_1$–$C_6$ alkylthio-$C_1$–$C_6$ alkyl and $C_2$–$C_6$ alkenyl, provided that the compound having the following formula is excluded,

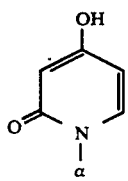

wherein α is hydrogen, $C_1$–$C_6$ alkyl, tetrahydrofuranyl, tetrahydropyranyl, $C_1$–$C_6$ alkoxy-$C_1$–$C_6$ alkyl, mono- or di ($C_1$–$C_6$ alkyl)-carbamoyl, $C_1$–$C_6$ alkylthio-$C_1$–$C_6$ alkyl or $C_2$–$C_6$ alkenyl.

3. A pharmaceutical composition as defined in claim 1, wherein the pyridine compound has the formula

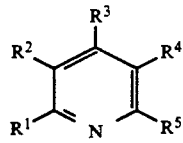

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring,
$R^2$ is a hydrogen atom,
$R^3$ is a hydrogen atom, a hydroxy group, $C_{1-20}$ alkanoyloxy group or a benzoyloxy group which may optionally be substituted with a $C_{1-6}$ alkyl group or a $C_{1-6}$ alkoxy group on the phenyl ring,
$R^4$ is a hydrogen atom, a halogen atom, a $C_{1-6}$ alkyl group, a cyano group or a nitro group,
$R^5$ is a hydrogen atom, a hydroxyl group or a halogen-substituted benzoyloxy group, when at least one of $R^1$, $R^3$ and $R^5$ is (are) hydroxy, the structure of 1-position on the pyridine ring can be

due to keto-enol tautomerism, the hydrogen attached to nitrogen being optionally substituted with a tetrahydrofuranyl group of a $C_{1-6}$ alkoxy-$C_{1-6}$ alkyl group, provided that one of $R^3$ and $R^5$ represents a hydrogen atom and that when each of $R^1$ and $R^3$ represents a hydroxy group, $R^4$ is not a hydrogen atom.

4. A pharmaceutical composition as defined in claim 2, wherein the pyridine compound has the formula

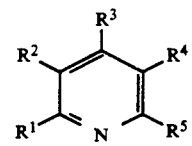

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring,
$R^2$ is a hydrogen atom,
$R^3$ is a hydrogen atom,
$R^4$ is a hydrogen atom, a halogen atom, a cyano group or a nitro group,
$R^5$ is a hydroxyl group or a halogen-substituted benzoyloxy group,
when at least one of $R^1$ and $R^5$ is (are) hydroxy, the structure of 1-position on the pyridine ring can be

due to keto-enol tautomerism.

5. A pharmaceutical composition as defined in claim 2, wherein the pyridine compound is selected from the group consisting of
2,4-dihydroxy-5-chloropyridine,
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

6. A pharmaceutical composition as defined in claim 2, wherein the anti-cancer compound is selected from the group consisting of 5-fluorouracil,
1-(2-tetrahydrofuryl)-5-fluorouracil,
1-n-hexylcarbamoyl-5-fluorouridine,
5'-deoxy-5-fluorouridine,
2'-deoxy-5-fluorouridine,
1-ethoxymethyl-5-fluorouracil, 2'-deoxy-5-fluoro-3-(3,4-methylenedioxy-benzoyl)uridine,
5-fluorouridine,
2'-deoxy-5-fluoro-3',5'-bis-O-(4-methoxy-phenoxycarbonyl)-3-(n-propoxybenzoyl)uridine,
2'-deoxy-3'-O-benzyl-5-fluorouridine,
5'-O-acetyl-3'-benzyl-2'-deoxy-5-fluorouridine,
2'-deoxy-3'-O-benzyl-3-benzoyl-5-fluorouridine and
2'-deoxy-3'-O-(4-chlorobenzyl)-5-fluorouridine; and
the pyridine compound has the formula

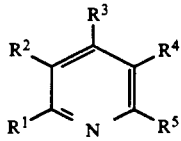

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring, $R^2$ is a hydrogen atom, $R^3$ is a hydrogen atom, a hydroxyl group, $C_{1-20}$ alkanoyloxy group or a benzoyloxy group which may optionally be substituted with a $C_{1-6}$ alkyl group or a $C_{1-6}$ alkoxy group on the phenyl ring, $R^4$ is a hydrogen atom, a halogen atom, a $C_{1-6}$ alkyl group, a cyano group or a nitro group, $R^5$ is a hydrogen atom, a hydroxyl group or a halogen-substituted benzoyloxy group, when at least one of $R^1$, $R^3$ and $R^5$ is (are) hydroxy, the structure of 1-position on the pyridine ring can be

due to keto-enol tautomerism, the hydrogen attached to nitrogen being optionally substituted with a tetrahydrofuranyl group or a $C_{1-6}$ alkoxy-$C_{1-6}$ alkyl group, provided that one of $R^3$ and $R^5$ represents a hydrogen atom and that when each of $R^1$ and $R^3$ represents a hydroxy group, $R^4$ is not a hydrogen atom.

7. A pharmaceutical composition as defined in claim 6, wherein the pyridine compound has the formula

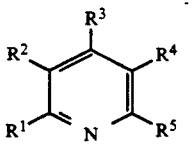

wherein $R^1$ is a hydroxy group, a furoyloxy group or a benzyoyloxy group which may optionally have 1 to 3 substituents selected from the group consisting of a $C_{1-6}$ alkoxy group and a halogen atom on the phenyl ring, $R^2$ is a hydrogen atom, $R^3$ is a hydrogen atom, $R^4$ is a hydrogen atom, a halogen atom, a cyano group or a nitro group, $R^5$ is a hydroxyl group or a halogen-substituted benzoyloxy group, when at least one of $R^1$ and $R^5$ is (are) hydroxy, the structure of 1-position on the pyridine ring can be

due to keto-enol tautomerism.

8. A pharmaceutical composition as defined in claim 6, wherein the pyridine compound is selected from the group consisting of
2,4-dihydroxy-5-chloropyridine,
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and 6-benzoyloxy-2-(4-bromobenzoyloxy)-3-cyanopyridine.

9. A pharmaceutical composition as defined in claim 1, wherein $R^3$ and $R^5$ are not hydrogen at the same time and one of $R^2$ and $R^4$ is hydrogen and the other is halogen, amino, carboxy, carbamoyl, cyano, nitro, $C_1$–$C_6$ alkyl, $C_2$–$C_6$ alkenyl or ($C_1$–$C_6$-alkoxy) - carbonyl.

10. A pharmaceutical composition as defined in claim 9, wherein one of $R^2$ and $R^4$ is hydrogen and the other is halogen or cyano.

11. A pharmaceutical composition as defined in claim 9, wherein $R^1$ is hydroxy, $C_{1-6}$ alkanoyloxy, benzoyloxy, furoyloxy or thenoyloxy; $R^3$ and $R^5$ are each hydrogen, hydroxy, $C_{1-6}$ alkanoyloxy, benzoyloxy or furoyloxy, provided that when at least one of $R^1$, $R^3$ and $R^5$ is hydroxy, the structure of 1-position on the pyridine ring can be

;

and one of $R^2$ and $R^4$ is hydrogen and the other is halogen or cyano.

12. A pharmaceutical composition as defined in claim 9, wherein $R^1$ is hydroxy, $C_{1-6}$ alkanoyloxy, benzoyloxy, furoyloxy or thenoyloxy; $R^3$ and $R^5$ are each hydrogen, hydroxy, $C_{1-6}$ alkanoyloxy, benzoyloxy or furoyloxy, provided that when at least one of $R^1$, $R^3$ and $R^5$ is hydroxy, the nitrogen atom of 1-position on the pyridine ring has tetrahydrofuranyl as a substituent; and one of $R^2$ and $R^4$ is hydrogen and the other is halogen or cyano.

13. A pharmaceutical composition as defined in claim 10, wherein the pyridine compound is selected from the group consisting of 4-acetoxy-5-chloro-2-pyridone, 4-benzoyloxy-5-chloro-2-pyridone, 5-chloro-4-(2-furoyloxy)-2-pyridone, 2-acetoxy-5-chloro-4-hydroxypyridine, 2-benzoyloxy-5-chloro-4-hydroxypyridine, 5-chloro-4-hydroxy-1-(2-tetrahydrofuranyl)-2-pyridone, 4-benzoyloxy-3-chloro-1-(2-tetrahydrofuranyl)-2-pyridone, 4-benzoyloxy-2-pyridone, 5-chloro-2,4-diacetoxypyridine, 6-benzoyloxy-3-cyano-2-hydroxypyridine, 3-cyano-6-(2-furoyloxy)-2-hydroxypyridine, 3-cyano-2-hydroxy-6-(2-thenoyloxy)-pyridine and 6-benzoyloxy-3-chloro-2-hydroxypyridine.

14. A pharmaceutical composition as defined in claim 13, wherein the pyridine compound is selected from the group consisting of 6-benzoyloxy-3-cyano-2-hydroxypyridine, 6-benzoyloxy-3-chloro-2-hydroxypyridine, 4-acetoxy-5-chloro-2-pyridone and 4-benzoyloxy-5-chloro-2-pyridone.

15. A pharmaceutical composition as defined in claim 1, wherein the anti-cancer compound is 5-fluorouracil compound having the formula (2-a) or a compound having the formula (2-b).

16. A pharmaceutical composition as defined in claim 15, wherein the pyridine compound has the formula

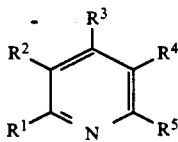

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring, $R^2$ is a hydrogen atom, $R^3$ is a hydrogen atom, a hydroxy group, $C_{1-20}$ alkanoyloxy group or a benzoyloxy group which may optionally be substituted with a $C_{1-6}$ alkyl group or a $C_{1-6}$ alkoxy group on the phenyl ring, $R^4$ is a hydrogen atom, a halogen atom, a $C_{1-6}$ alkyl group, a cyano group or a nitro group, $R^5$ is a hydrogen atom, a hydroxyl group or a halogen-substituted benzoyloxy group, when at least one of $R^1$, $R^3$ and $R^5$ is hydroxy, the structure of 1-position on the pyridine ring can be

due to keto-enol tautomerism, the hydrogen attached to nitrogen being optionally substituted with a tetrahydrofuranyl group of a $C_{1-6}$ alkoxy-$C_{1-6}$ alkyl group, provided that one of $R^3$ and $R^5$ represents a hydrogen atom and that when each of $R^1$ and $R^3$ represents a hydroxy group, $R^4$ is not a hydrogen atom.

17. A pharmaceutical composition as defined in claim 15, wherein the pyridine compound has the formula

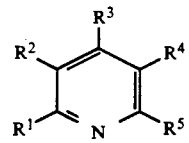

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring, $R^2$ is a hydrogen atom, $R^3$ is a hydrogen atom, $R^4$ is a hydrogen atom, a halogen atom, a cyano group or a nitro group, $R^5$ is a hydroxyl group or a halogen-substituted benzoyloxy group, when at least one of $R^1$ and $R^5$ is hydroxy, the structure of 1-position on the pyridine ring can be

due to keto-enol tautomerism.

18. A pharmaceutical composition as defined in claim 15, wherein the pyridine compound is selected from the group consisting of
2,4-dihydroxy-5-chloropyridine,
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

19. A pharmaceutical composition as defined in claim 15, wherein $R^a$ and $R^{a1}$ in the 5-fluorouracil compounds having the formula (2-a) are each acyl group selected from the group consisting of alkanoyl group having 1 to 20 carbon atoms and optionally substituted with phenyl-($C_1$-$C_6$ alkoxy)carbonyl, ($C_1$-$C_6$ alkyl) - carbamoyl, phenyl or phenoxy; arylcarbonyl group which may be optionally substituted with $C_1$-$C_4$ alkylenedioxy or with 1 to 3 substituents selected from the group consisting of halogen, $C_1$-$C_6$ alkyl, $C_1$-$C_6$ alkoxy, nitro, phenyl-($C_1$-$C_6$ alkoxy) carbonyl, carboxyl, hydroxy, guanidyl, phenyl-$C_1$-$C_6$alkoxy and amino optionally substituted with $C_1$-$C_6$ alkyl; ($C_1$-$C_6$ alkoxy) carbonyl group;

phenoxycarbonyl group; pyridylcarbonyl group; thienylcarbonyl group; and furanylcarbonyl group.

20. A pharmaceutical composition as defined in claim 15, wherein the 5-fluorouracil compound having the formula (2-a) or a compound having the formula (2-b) is one selected from the group consisting of 5-fluorouracil, 1-(2-tetrahydrofuranyl)-5-fluorouracil, 1-hexyl-carbamoyl-5-fluorouracil, 1-ethoxymethyl-5-fluorouracil, 5-fluorouridine, 5'-deoxy-5-fluorouridine, 2'-deoxy-5-fluoro-3-(3,4-methylenedioxybenzoyl)uridine, 2'-deoxy-5-fluoro-3,40 ,5'-bis-O-(4-methyoxyphenoxycarbonyl)-3-(n-propoxybenzoyl)uridine, ethyl($\pm$)-6-t-butoxy-5-fluoro-2,4-dioxohexahydropyrimidine-$\gamma$-5-carboxylate, 1-phthalidyl-5-fluorouracil, 2'-deoxy-5-fluorouridine, ethyl 5-fluoro-6-(e)-(2-furfurylidene-aminoxy)-1,2,3,4,5,6-hexahydro-2,4-dioxopyrimidine-5-carboxylate and ethyl 5-fluoro-6-(z)-(2-furfurylidene-aminoxy)-1,2,3,4,5,6-hexahydro-2,4-dioxopyrimidine-5-carboxylate.

21. A pharmaceutical composition as defined in claim 20, wherein the 5-fluorouracil compound is one selected from the group consisting of 5-fluorouracil, 1-(2-tetrahydro-furanyl)-5-fluorouracil, 1-phthalidyl-5-fluorouracil, 5'-deoxy-5-fluorouracil, 5-fluorouridine, 2'-deoxy-5-fluorouridine and 1-n-hexylcarbamoyl-5-fluorouracil.

22. A pharmaceutical composition as defined in claim 1, wherein the anti-cancer compound is a 2'-deoxy-5-fluoro-uridine compound having the formula (3).

23. A pharmaceutical composition as defined in claim 22, wherein $R^e$, $R^f$ and $R^g$ in the 2'-deoxy-5-fluorouridine compound are each acyl group selected from the group consisting of substituted or unsubstituted $C_{1-20}$ alkanoyl group, substituted or unsubstituted aryl-carbonyl group, 5- or 6-membered unsaturated hetero ring-carbonyl group having nitrogen, sulfur or oxygen atom as the hetero atom, carbonic acid ester residue, substituted or unsubstituted cycloalkyl carbonyl group, lower alkenyl carbonyl group and lower alkynyl carbonyl group.

24. A pharmaceutical composition as defined in claim 22, wherein the 2'-deoxy-5-fluorouridine compound is 3'-O-benzyl-2'-deoxy-5-fluorouridine, 3-benzoyl-3'-O-benzyl-2'-deoxy-5-fluorouridine, 5'-O-acetyl-3'-O-benzyl-2'-deoxy-5-fluorouridine or 2'-deoxy-3'-O-(4-chlorobenzyl)-5-fluorouridine.

25. A pharmaceutical composition as defined in claim 22, wherein the pyridine compound has the formula

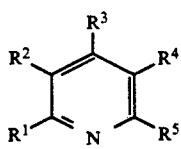

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring,
$R^2$ is a hydrogen atom,
$R^3$ is a hydrogen atom, a hydroxy group, $C_{1-20}$ alkanoyloxy group or a benzoyloxy group which may optionally be substituted with a $C_{1-6}$ alkyl group or a $C_{1-6}$ alkoxy group on the phenyl ring,
$R^4$ is a hydrogen atom, a halogen atom, a $C_{1-6}$ alkyl group, a cyano group or a nitro group, $R^5$ is a hydrogen atom, a hydroxyl group or a halogen-substituted benzoyloxy group,
when at least one of $R^1$, $R^3$ and $R^5$ is (are) hydroxy, the structure of 1-position on the pyridine ring can be $$\diagdown N \diagup$$
$$\underset{H}{|}$$

due to keto-enol tautomerism, the hydrogen attached to nitrogen being optionally substituted with a tetrahydrofuranyl group or a $C_{1-6}$ alkoxy-$C_{1-6}$ alkyl group, provided that one of $R^3$ and $R^5$ represents a hydrogen atom and that when each of $R^1$ and $R^3$ represents a hydroxy group, $R^4$ is not a hydrogen atom.

26. A pharmaceutical composition as defined in claim 22, wherein the pyridine compound has the formula wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring,
$R^2$ is a hydrogen atom,
$R^3$ is a hydrogen atom,
$R^4$ is a hydrogen atom, a halogen atom, a cyano group or a nitro group,
$R^5$ is a hydroxyl group or a halogen-substituted benzoyloxy group,
when at least one of $R^1$ and $R^5$ is (are) hydroxy, the structure of 1-position on the pyridine ring can be $$\diagdown N \diagup$$
$$\underset{H}{|}$$

due to keto-enol tautomerism.

27. A pharmaceutical composition as defined in claim 22, wherein the pyridine compound is selected from the group consisting of
2,4-dihydroxy-5-chloropyridine,
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo- 1-methoxymethylpyridine,
6-benzoyloxy-3-cyano-2-hydroxypyridine, 3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

28. A pharmaceutical composition as defined in claim 1, which is administered in the form of a single preparation comprising the anti-cancer compound and the pyridine compound.

29. A pharmaceutical composition as defined in claim 1, which is administered in the form of separate preparations, one comprising the anti-cancer compound and the other comprising the pyridine compound.

30. A pharmaceutical composition as defined in claim 1, which contains about 0.5 to 1.5 moles of the pyridine compound per mole of the anti-cancer compound.

31. A pharmaceutical composition as defined in claim 1, wherein the anti-cancer compound is one selected from the group consisting of 5-fluorouracil, 1-hexyl-carbamoyl-5-fluorouracil, 1-ethoxymethyl-5-fluorouracil, 5-fluorouridine, 5'-deoxy-5-fluorouridine, 2'-deoxy-5-fluoro-3-(3,4-methylenedioxybenzoyl)uridine, 2'-deoxy-5-fluoro-3',5'-bis-O-(4-methyoxyphenoxycarbonyl)-3-(n-propoxybenzoyl)uridine,ethyl($\pm$)-6-t-butoxy-5-fluoro-2,4-dioxohexahydropyrimidine-$\gamma$-5-carboxylate, 1-phthalidyl-5-fluorouracil, 2'-deoxy-5-fluorouridine, ethyl 5-fluoro-6-(e)-(2-furfurylidene-aminoxy)-1,2,3,4,5,6-hexahydro-2,4-dioxopyrimidine-5-carboxylate, ethyl 5-fluoro-6-(z)-(2-furfurylidene-aminoxy)-1,2,3,4,5,6-hexahydro-2,4-dioxopyrimidine-5-carboxylate, 3'-O-benzyl-2'-deoxy-5-fluorouridine, 3-benzoyl-3'-O-benzyl-2'-deoxy-5-fluorouridine,5'-O-acetyl-3'-O-benzyl-2'-deoxy-5-fluorouridine and 2'-deoxy-3'-O-(4-chlorobenzyl)-5-fluorouridine; and said pyridine compound is a compound selected from the group consisting of 4-acetoxy-5-chloro-2-pyridone, 4-benzoyloxy-5-chloro-2-pyridone, 5-chloro-4-(2-furoyloxy)-2-pyridone, 2-acetoxy-5-chloro-4-hydroxypyridine,2-benzoyloxy-5-chloro-4-hydroxypyridine, 5-chloro-4-hydroxy-1-(2-tetrahydrofuranyl)-2-pyridone, 4-benzoyloxy-3-chloro-1-(2-tetrahydrofuranyl)-2-pyridone, 4-benzoyloxy-2-pyridone, 5-chloro-2,4-diacetoxypyridine, 6-benzoyloxy-3-cyano-2-hydroxypyridine, 3-cyano-2-hydroxy-6-(2-thenoyloxy)-pyridine and 6-benzoyloxy-3-chloro-2-hydroxypyridine.

32. A pharmaceutical composition as defined in claim 31, wherein the anti-cancer compound is 1-(2-tetrahydrofuranyl)-5-fluorouracil.

33. A pharmaceutical composition as defined in claim 31, wherein the anti-cancer compound is 1-ethoxymethyl-5-fluorouracil.

34. A pharmaceutical composition as defined in claim 1, wherein the anti-cancer compound is selected from the group consisting of
5-fluorouracil,
1-(2-tetrahydrofuryl)-5-fluorouracil,
1-n-hexylcarbamoyl-5-fluorouridine,
5'-deoxy-5-fluorouridine,
2'-deoxy-5-fluorouridine,
1-ethoxymethyl-5-fluorouracil,
2'-deoxy-5-fluoro-3-(3,4-methylenedioxy-benzoyl)uridine,
5-fluorouridine,
2'-deoxy-5-fluoro-3'5'-bis-O-(4-methoxy-phenoxycarbonyl)-3-(n-propoxybenzoyl)uridine,
2'-deoxy-3'-O-benzyl-5-fluorouridine,
5'-O-acetyl-3'-benzyl-2'-deoxy-5-fluorouridine,
2'-deoxy-3'-O-benzyl-3-benzoyl-5-fluorouridine and
2'-deoxy-3'-O-(4-chlorobenzyl)-5-fluorouridine; and
the pyridine compound is selected from the group consisting of
2,4-dihydroxy-5-chloropyridine
2,6-dihydroxy-3-chloropyridine,
2,4-dihydroxy-5-bromopyridine,
2,4-dihydroxy-5-methylpyridine,
2,4-dihydroxy-3-cyanopyridine,
2,6-dihydroxy-3-nitropyridine,
2,6-dihydroxypyridine,
2,4-dihydroxy-5-carboxypyridine,
2,4-dihydroxy-5-ethoxycarbonylpyridine,
2,4-dihydroxy-3,5-dichloropyridine,
2,4-dihydroxy-3,5-dibromopyridine,
2,4-dihydroxy-3-chloropyridine,
2,4-dihydroxy-3-bromopyridine,
2,4-dihydroxy-3-methylpyridine,
2,4-dihydroxy-3-aminopyridine,
2,6-dihydroxy-3-carbamoylpyridine,
2,4,6-trihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

35. A pharmaceutical composition as defined in claim 34, wherein the anti-cancer compound is 1-(2-tetrahydrofuranyl)-5-fluorouracil.

36. A pharmaceutical composition as defined in claim 34, wherein the anti-cancer compound is 1-ethoxymethyl-5-fluorouracil.

37. A pharmaceutical composition as defined in claim 1, wherein the anti-cancer compound is 1-(2-tetrahydrofuryl)- 5-fluorouracil and the pyridine compound is 2,6-dihydroxy-3-cyanopyridine.

38. A method of potentiating the anti-cancer activity of an anti-cancer compound which comprises administering to a cancer patient an anti-cancer effective amount of an anti-cancer compound as defined in claim 1 in a single preparation together with about 0.1 to about 10 moles of a pyridine compound as defined in claim 1 per mole of the anti-cancer compound.

39. A method as defined in claim 38, wherein the pyridine compound and the anti-cancer compound are defined as in claim 2.

40. A method as defined in claim 38, wherein the anti-cancer compound is one selected from the group consisting of 5-fluorouracil, 1-(2-tetrahydrofuranyl)-5-fluorouracil, 1-hexylcarbamoyl-5-fluorouracil, 1-ethoxymethyl-5-fluorouracil, 5-fluorouridine, 5'-deoxy-5-fluorouridine, 2'-deoxy-5-fluoro-3-(3,4-methylenedioxybenzoyl)uridine,2'-deoxy-5-fluoro-3',5'-bis-O-(4-methoxyphenoxycarbonyl)-3-(n-propoxybenzoyl)uridine, ethyl(±)-6-t-butoxy-5-fluoro-2,4-dioxohexahydropyrimidine-γ-5-carboxylate, 1-phthalidyl-5-fluorouracil, 2'-deoxy-5-fluorouridine, ethyl 5-fluoro-6-(e)-(2-furfurylidene-aminoxy)-1,2,3,4,5,6-hexahydro-2,4-dioxopyrimidine-5-carboxylate, ethyl 5-fluoro-6-(z)-(2-furfurylidene-aminoxy)-1,2,3,4,5,6-hexahydro-2,4-dioxopyrimidine-5-carboxylate, 3'-O-benzyl-2'deoxy-5-fluorouridine, 3-benzoyl-3'-O-benzyl-2'-deoxy-5-fluorouridine, 5'-O-acetyl-3'-O-benzyl-2'-deoxy-5-fluorouridine and 2'-deoxy-3'-O-( 4-chlorobenzyl)-5-fluorouridine; and said pyridine derivative is a compound selected from the group consisting of 4-acetoxy-5-chloro-2-pyridone, 4-benzoyloxy-5-chloro-2-pyridone, 5-chloro-4-(2-furoyloxy)-2-pyridone, 2-acetoxy-5-chloro-4-hydroxypyridine, 2-benzoyloxy-5-chloro-4-hydroxypyridine, 5-chloro-4-hydroxy-1-(2-tetrahydrofuranyl)-2-pyridone, 4-benzoyloxy-3-chloro-1-(2-tetrahydrofuranyl)-2-pyridone, 4-benzoyloxy-2-pyridone, 5-chloro-2,4-diacetoxypyridine, 6-benzoyloxy-3-cyano-2-hydroxypyridine, 3-cyano-6-(2-furoyloxy)-2-hydroxypyridine, 3-cyano-2-hydroxy-6-(2-thenoyloxy)-pyridine and 6-benzoyloxy-3-chloro-2-hydroxypyridine.

41. A method as defined in claim 40, wherein the anti-cancer compound is 1-(2-tetrahydrofuranyl)-5-fluorouracil.

42. A method as defined in claim 40, wherein the anti-cancer compound is 1-ethoxymethyl-5-fluorouracil.

43. A method as defined in claim 38, wherein the anti-cancer compound is selected from the group consisting of
5-fluorouracil,
1-(2-tetrahydrofuryl)-5-fluorouracil,
1-n-hexylcarbamoyl-5-fluorouridine,
5'-deoxy-5-fluorouridine,
2'-deoxy-5-fluorouridine,
1-ethoxymethyl-5-fluorouracil,
2'-deoxy-5-fluoro-3-(3,4-methylenedioxy-benzoyl)uridine,
5-fluorouridine,
2'-deoxy-5-fluoro-3',5'-bis-O-(4-methoxy-phenoxycarbonyl)- 3-(n-propoxybenzoyl)uridine,
2'-deoxy-3'-O-benzyl-5-fluorouridine,
5'-O-acetyl-3'-benzyl-2'-deoxy-5-fluoro-uridine,
2'-deoxy-3'-O-benzyl-3-benzoyl-5-fluoro-uridine and
2'-deoxy-3'-O-(4-chlorobenzyl)-5-fluoro-uridine; and the pyridine derivative is selected from the group consisting of
2,4-dihydroxy-5-chloropyridine
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
2,4-dihydroxy-5-carboxypyridine,
2,4-dihydroxy-5-ethoxycarbonylpyridine,
2,4-dihydroxy-3,5-dichloropyridine,
2,4-dihydroxy-3,5-dibromopyridine,
2,4-dihydroxy-3-chloropyridine,
2,4-dihydroxy-3-bromopyridine,
2,4-dihydroxy-3-methylpyridine,
2,4-dihydroxy-3-aminopyridine,
2,6-dihydroxy-3-carbamoylpyridine,
2,4,6-trihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

44. A method as defined in claim 41, wherein the anti-cancer compound is 1-(2-tetrahydrofuranyl)-5-fluorouracil.

45. A method as defined in claim 41, wherein the anti-cancer compound is 1-ethoxymethyl-5-fluorouracil.

46. A method as defined in claim 38, wherein the anti-cancer compound is 1-(2-tetrahydrofuryl)-5-fluorouracil and the pyridine compound is 2,6-dihydroxy-3-cyanopyridine.

47. A method as defined in claim 38, wherein the pyridine compound has the formula

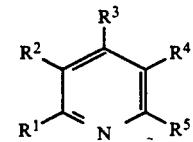

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring,
$R^2$ is a hydrogen atom,
$R^3$ is a hydrogen atom, a hydroxy group, $C_{1-20}$ alkanoyloxy group or a benzoyloxy group which may optionally be substituted with a $C_{1-6}$ alkyl group or a $C_{1-6}$ alkoxy group on the phenyl ring,
$R^4$ is a hydrogen atom, a halogen atom, a $C_{1-6}$ alkyl group, a cyano group or a nitro group,
$R^5$ is a hydrogen atom, a hydroxyl group or a halogen-substituted benzoyloxy group,
when at least one of $R^1$, $R^3$ and $R^5$ is (are) hydroxy, the structure of 1-position on the pyridine ring can be

due to keto-enol tautomerism, the hydrogen attached to nitrogen being optionally substituted with a tetrahydrofuranyl group of a $C_{1-6}$ alkoxy-$C_{1-6}$ alkyl group, provided that one of $R^3$ and $R^5$ represents a hydrogen atom and that when each of $R^1$ and $R^3$ represents a hydroxy group, $R^4$ is not a hydrogen atom.

48. A method as defined in claim 38, wherein the pyridine compound has the formula

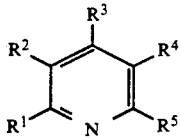

wherein R¹ is a hydroxy group, a furoyloxy group or a benzoyloxy group which may optionally have 1 to 3 substituents selected from the group consisting of a C$_{1-6}$ alkoxy group and a halogen atom on the phenyl ring, R² is a hydrogen atom, R³ is a hydrogen atom, R⁴ is a hydrogen atom, a halogen atom, a cyano group or a nitro group, R⁵ is a hydroxyl group or a halogen-substituted benzoyloxy group, when at least one of R¹ and R⁵ is hydroxy, the structure of 1-position on the pyridine ring can be

due to keto-enol tautomerism.

49. A method as defined in claim 38, wherein the pyridine compound is selected from the group consisting of
2,4-dihydroxy-5-chloropyridine,
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

50. A method of potentiating the anti-cancer activity of an anti-cancer compound which comprises administering to a cancer patient a preparation containing an anti-cancer effective amount of an anti-cancer compound as defined in claim 1 and in a separate preparation about 0.1 to about 10 moles of a pyridine compound as defined in claim 1 per mole of the anti-cancer compound.

51. A method as defined in claim 50, wherein the anti-cancer compound and the pyridine compound are as defined in claim 2.

52. A method as defined in claim 50, wherein the anti-cancer compound is one selected from the group consisting of 5-fluorouracil, 1-hexyl-carbamoyl-5-fluorouracil, 1-ethoxymethyl-5-fluorouracil, 5-fluorouridine, 5'-deoxy-5-fluorouridine, 2'-deoxy-5-fluoro-3-(3,4-methylenedioxybenzoyl)uridine, 2'-deoxy-5-fluoro-3',5'-bis-O-(4-methoxyphenoxycarbonyl)-3-(n-propoxybenzoyl)uridine, ethyl(±)-6-t-butoxy-5-fluoro-2,4-dioxohexahydropyrimidine-γ-5-carboxylate, 1-phthalidyl-5-fluorouracil, 2'-deoxy-5-fluorouridine, ethyl 5-fluoro-6-(e)-(2-furfurylidene-aminoxy)-1,2,3,4,5,6-hexahydro-2,4-dioxopyrimidine-5-carboxylate, ethyl 5-fluoro-6-(z)-(2-furfurylidene-aminoxy)-1,2,3,4,5,6-hexahydro-2,4-dioxopyrimidine-5-carboxylate, 3'-O-benzyl-2'-deoxy-5-fluorouridine, 3-benzoyl-3'-O-benzyl-2'-deoxy-5-fluorouridine, 5'-O-acetyl-3'-O-benzyl-2'-deoxy-5-fluorouridine and 2'-deoxy-3'-O-(4-chlorobenzyl)-5-fluorouridine; and the pyridine derivative is a compound selected from the group consisting of 4-acetoxy-5-chloro-2-pyridone, 4-benzoyloxy-5-chloro-2-pyridone, 5-chloro-4-(2-furoyloxy)-2-pyridone, 2-acetoxy-5-chloro-4-hydroxypyridine, 2-benzoyloxy-5-chloro-4-hydroxypyridine, 5-chloro-4-hydroxy-1-(2-tetrahydrofuranyl)-2-pyridone, 4-benzoyloxy-3-chloro-1-(2-tetrahydrofuranyl)-2-pyridone, 4-benzoyloxy-2-pyridone, 5-chloro-2,4-diacetoxypyridine, 6-benzoyloxy-3-cyano-2-hydroxypyridine, 3-cyano-6-(2-furoyloxy)-2-hydroxypyridine, 3-cyano-2-hydroxy-6-(2-furoyloxy)-2-hydroxypyridine, 3-cyano-2-hydroxy-6-(2-thenoyloxy)-pyridine and 6-benzoyloxy-3-chloro-2-hydroxypyridine.

53. A method as defined in claim 52, wherein the anti-cancer compound is 1-(2-tetrahydrofuranyl)-5-fluorouracil.

54. A method as defined in claim 52, wherein the anti-cancer compound is 1-ethoxymethyl-5-fluorouracil.

55. A method as defined in claim 50, wherein the anti-cancer compound is selected from the group consisting of
5-fluorouracil,
1-(2-tetrahydrofuryl)-5-fluorouracil,
1-n-hexylcarbamoyl-5-fluorouridine,
5'-deoxy-5-fluorouridine,
2'-deoxy-5-fluorouridine,
1-ethoxymethyl-5-fluorouracil,
2'-deoxy-5-fluoro-3-(3,4-methylenedioxy-benzoyl)uridine,
5-fluorouridine,
2'-deoxy-5-fluoro-3'5'-bis-O-(4-methoxy-phenoxycarbonyl)- 3-(n-propoxybenzoyl)uridine,
2'-deoxy-3'-O-benzyl-5-fluorouridine,
5'-O-acetyl-3'-benzyl-2'-deoxy-5-fluoro-uridine,
2'-deoxy-3'-O-benzyl-3-benzoyl-5-fluoro-uridine and
2'-deoxy-3'-O-(4-chlorobenzyl)-5-fluoro-uridine; and the pyridine compound is selected from the group consisting of
2,4-dihydroxy-5-chloropyridine
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
2,4-dihydroxy-5-carboxypyridine,
2,4-dihydroxy-5-ethoxycarbonylpyridine,
2,4-dihydroxy-3,5-dichloropyridine,
2,4-dihydroxy-3,5-dibromopyridine,
2,4-dihydroxy-3-chloropyridine,
2,4-dihydroxy-3-bromopyridine, 2,4-dihydroxy-3-methylpyridine,
2,4-dihydroxy-3-aminopyridine,
2,6-dihydroxy-3-carbamoylpyridine,
2,4,6-trihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and
6-benzoyloxy-2-(4-bromobenzoyloxy)-3-cyanopyridine.

56. A method as defined in claim 55, wherein the anti-cancer compound is 1-(2-tetrahydrofuranyl)-5-fluorouracil.

57. A method as defined in claim 55, wherein the anti-cancer compound is 1-ethoxymethyl-5-fluorouracil.

58. A method as defined in claim 50, wherein the anti-cancer compound is 1-(2-tetrahydrofuryl)-5-fluorouracil and the pyridine compound is 2,6-dihydroxy-3-cyanopyridine.

59. A method as defined in claim 50, wherein the pyridine compound has the formula

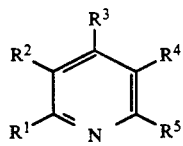

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring, $R^2$ is a hydrogen atom, $R^3$ is a hydrogen atom, a hydroxy group, $C_{1-20}$ alkanoyloxy group or a benzoyloxy group which may optionally be substituted with a $C_{1-6}$ alkyl group or a $C_{1-6}$ alkoxy group on the phenyl ring, $R^4$ is a hydrogen atom, a halogen atom, a $C_{1-6}$ alkyl group, a cyano group or a nitro group, $R^5$ is a hydrogen atom, a hydroxyl group or a halogen-substituted benzoyloxy group, when at least one of $R^1$, $R^3$ and $R^5$ is (are) hydroxy, the structure of 1-position on the pyridine ring can be

due to keto-enol tautomerism, the hydrogen attached to nitrogen being optionally substituted with a tetrahydrofuranyl group of a $C_{1-6}$ alkoxy-$C_{1-6}$ alkyl group, provided that one of $R^3$ and $R^5$ represents a hydrogen atom and that when each of $R^1$ and $R^3$ represents a hydroxy group, $R^4$ is not a hydrogen atom.

60. A method as defined in claim 50, wherein the pyridine compound has the formula

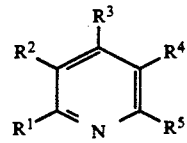

wherein $R^1$ is a hydroxy group, a furoyloxy group or a benzoyloxy group which may optionally have 1 to 3 substituents selected from the group consisting of a $C_{1-6}$ alkoxy group and a halogen atom on the phenyl ring, $R^2$ is a hydrogen atom, $R^3$ is a hydrogen atom, $R^4$ is a hydrogen atom, a halogen atom, a cyano group or a nitro group, $R^5$ is a hydroxyl group or a halogen-substituted benzoyloxy group, when at least one of $R^1$ and $R^5$ is (are) hydroxy, the structure of 1-position on the pyridine ring can be

due to keto-enol tautomerism.

61. A method as defined in claim 50, wherein the pyridine compound is selected from the group consisting of 2,4-dihydroxy-5-chloropyridine,
2,6-dihydroxy-3-chloropyridine,
2,4-dihydroxy-5-bromopyridine,
2,4-dihydroxy-5-methylpyridine,
2,6-dihydroxy-3-cyanopyridine,
2,6-dihydroxy-3-nitropyridine,
2,6-dihydroxypyridine,
5-chloro-4-octadecanoyloxy-2-pyridone,
2,4-dibenzoyloxypyridine,
6-benzoyloxy-2-pyridone,
2-benzoyloxy-5-chloro-4-hydroxypyridine,
5-chloro-4-(2-methylbenzoyloxy)-2-pyridone,
4-benzoyloxy-5-chloro-2-pyridone,
2,4-bis(4-ethoxybenzoyloxy)pyridine,
5-chloro-1,2-dihydro-4-hydroxy-2-oxo-1-(2-tetrahydrofuranyl)pyridine,
5-chloro-1,2-dihydro-4-hydroxy-2-oxo-1-methoxymethylpyridine,
6-benzoyloxy-3-cyano-2-hydroxypyridine,
3-cyano-6-(3,4,5-trimethoxybenzoyl)-2-hydroxypyridine,
3-cyano-6-(2-furoyloxy)-2-hydroxypyridine,
3-cyano-6-(3,4-dichlorobenzoyloxy)-2-hydroxypyridine and 6-benzoyloxy-2-(4-bromobenzoyloxy)-3-cyanopyridine.

* * * * *